US 6,358,995 B1

(12) United States Patent
Tagami et al.

(10) Patent No.: US 6,358,995 B1
(45) Date of Patent: Mar. 19, 2002

(54) CARBOXYLIC ACID DERIVATIVES HAVING FUSED RINGS

(75) Inventors: Katsuya Tagami, Tsuchiura; Hiroyuki Yoshimura, Tsukuba; Mitsuo Nagai, Tsukuba; Shigeki Hibi, Tsukuba; Kouichi Kikuchi, Tsuchiura; Takashi Sato, Tsukuba; Makoto Okita, Tsukuba; Yasushi Okamoto, Tsukuba-gun; Yumiko Nagasaka, Tsukuba; Naoki Kobayashi, Tsukuba; Takayuki Hida, Tsukuba; Kenji Tai, Tsukuba; Naoki Tokuhara, Tsukuba; Seiichi Kobayashi, Tsuchiura, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/621,889

(22) Filed: Jul. 21, 2000

Related U.S. Application Data

(62) Division of application No. 09/125,522, filed as application No. PCT/JP97/00852 on Mar. 18, 1997, now Pat. No. 6,121,309.

(30) Foreign Application Priority Data

Mar. 18, 1996 (JP) .............................. 8-88792
Aug. 9, 1996 (JP) ............................. 8-210836
Dec. 25, 1996 (JP) ............................. 8-345515

(51) Int. Cl.[7] ....................... A61K 31/40; A61K 31/38; A61K 31/235; C07D 405/00; C07D 311/04
(52) U.S. Cl. ....................... 514/422; 514/428; 514/444; 514/456; 514/544; 548/525; 548/527; 548/562; 549/59; 549/60; 549/406; 549/407; 562/490
(58) Field of Search ................. 548/562, 525, 548/527; 514/428, 422, 444, 456, 544; 549/59, 60, 406, 407; 562/490

(56) References Cited

U.S. PATENT DOCUMENTS

| 3,974,172 A | 8/1976 | Sahm et al. |
| 4,129,568 A | 12/1978 | Howe |
| 4,135,910 A | 1/1979 | Howe |
| 4,139,366 A | 2/1979 | Howe |
| 4,166,732 A | 9/1979 | Howe |
| 4,233,440 A | 11/1980 | Dorlars et al. |
| 5,278,318 A | 1/1994 | Chandraratna |
| 5,428,052 A | 6/1995 | Shroot et al. |
| 5,776,954 A | 7/1998 | De Laszio et al. |
| 6,271,253 B1 * | 8/2001 | Carter et al. ................ 514/432 |

FOREIGN PATENT DOCUMENTS

| EP | 0337176 A2 | 10/1989 |
| EP | 0747347 A1 | 12/1996 |
| EP | 0838 453 A1 | 4/1998 |
| JP | 49-83725 A | 8/1997 |
| JP | 49-112926 A | 10/1997 |
| JP | 61-85360 A | 4/1998 |
| JP | 6-501948 A | 3/1999 |
| JP | 6-502178 A | 3/1999 |
| WO | WO-A92/12154 | 7/1992 |
| WO | WO94/14777 | 7/1994 |
| WO | WO95/04036 | 2/1995 |
| WO | WO97/09297 | 3/1997 |
| WO | WO 97/02244 A | 1/1999 |

OTHER PUBLICATIONS

Khim. Geterotskl. Soedin., (9), (1986), Krasovitskii, B.M. et al., p. 1261–4.

Chemical Abstracts, 100, Abstract No. 87266 & SU, 1051083, A1 (1984).

(List continued on next page.)

Primary Examiner—Deborah C. Lambkin
(74) Attorney, Agent, or Firm—Nixon & Vanderhye

(57) ABSTRACT

The present invention provides a medicament exhibiting excellent retinoic acid receptor agonism.

A Carboxylic acid derivative having a fused ring which is represented by the following formula or a pharmacologically acceptable salt thereof:

{wherein the symbol ==== represents a single bond or a double bond; X, Y, Z, P, Q, U, V and W are each a group represented by the formula: —O— or —S—, or a group represented by the formula:

[wherein $R^k$ (k: 1 to 8) is hydrogen, halogeno, optionally substituted lower alkyl or the like, with either of $R^7$ and $R^8$ being a group represented by the formula:

(wherein A and B are each independently an optionally substituted aromatic hydrocarbon ring or an optionally substituted unsaturated heterocycle; and D is optionally protected carboxyl)]}.

7 Claims, No Drawings

OTHER PUBLICATIONS

Liebigs Ann. Chem., (11), (1983), Boberg Friedrich et al., p. 2029–33.

J. Heterocycl. Chem., 19(4), (1982), Howe Robert K. et al., p. 721–6.

Chemical Abstracts, 89, Abstract No. 129303 & Bull. Chem. Soc. Jpn., 51(5), (1978), p. 1473–6.

J. Inst. Chem. (India), 49(6), (1977), Banerjee M. et al., p. 291–3.

Chemical Abstract 100 (1984), 34355t.

Chemical Abstract 107, (1987) 23273h.

Pestic. Sci., 6(5), (1975), Geissler Art E. et al., p. 441–50.

* cited by examiner

CARBOXYLIC ACID DERIVATIVES HAVING FUSED RINGS

This is a division of application Ser. No. 09/125,522, filed Aug. 20, 1998, now U.S. Pat. No. 6,121,309, which is a 35 U.S.C. §371 of PCT/jp97/00852 filed Mar. 18, 1997, the entire content of which is hereby incorporated by reference in this application.

BACKGROUND OF THE INVENTION

1. Field of the Invention

The present invention relates to a carboxylic acid derivative having a fused ring and a pharmacologically acceptable salt thereof. More specifically, it relates to a novel carboxylic acid derivative having a fused ring which exhibit agonism for retinoic acid receptors and a pharmacologically acceptable salt thereof.

2. Prior Art

Retinoic acid is a substance essential to the growth and life support of human being and other mammals. It has been known that retinoic acid acts as a morphogenetic factor in ontogenesis and functions variously in the differentiation and proliferation of cells of adults. For example, it has been known that the acid participates in cornification, formation of hair, functions of sebaceous gland and so on with respect to the epidermis, in metabolism of bone and cartilage with respect to the connective tissue, in regulation of immune functions with respect to the immune system, in differentiation of nerve cells with respect to the nervous system, in differentiation and proliferation of blood cells with respect to the hemic system, and in the lipid metabolism, the mineral metabolism and the basal metabolism and so on. These various physiological actions of retinoic acid are exhibited by various control mechanisms through retinoid receptor family present in the cell nucleus, for example, by regulating the expression of transcription activators, by regulating the expression of enzymes such as collagenase, tissue plasminogen activator or tyrosine kinase, or by regulating the production of cytokines such as IL-6.

The connections of the above physiological actions of retinoic acid with various diseases have recently been elucidated gradually, and in particular, differentiation-inducing therapy with all-trans retinoic acid has attracted attention as a new therapeutic method for some cancers such as acute promyelocytic leukemia.

With respect to retinoic acid, however, there have appeared problematic tolerance due to the induction of P450 which is a hepatic metabolic enzyme, adverse effects due to accumulation, and other problems. Under these circumstances there have been expected research and development of novel retinoid-related compounds which can be substituted for retionic acid as preventive and therapeutic drugs for various diseases.

DISCLOSURE OF INVENTION

SUMMARY OF THE INVENTION

Under the above circumstances, the inventors of the present invention have found that the desired objects can be attained by carboxylic acid derivatives having fused rings which will be described, and the present invention has been accomplished on the basis of this finding.

Namely, the present invention relates to a carboxylic acid derivative having a fused ring which is represented by the formula (A), or a pharmacologically acceptable salt thereof:

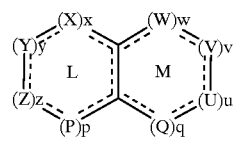

(A)

{wherein the rings L and M are fused with each other; the symbol ═══ represents a single bond or a double bond; X represents a group represented by the formula: —O— or —S—, or a group represented by the formula:

(wherein $R^1$ represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl), and x is an integer of 0 or 1;

Y represents a group represented by the formula: —O— or —S—, or a group represented by the formula:

(wherein $R^2$ represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl), and y is an integer of 0 or 1;

Z represents a group represented by the formula: —O— or —S—, or a group represented by the formula:

(wherein $R^3$ represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl), and z is an integer of 0 or 1;

P represents a group represented by the formula: —O— or —S—, or a group represented by the formula:

(wherein R⁴ represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl), and p is an integer of 0 or 1;

Q represents a group represented by the formula: —O— or —S—, or a group represented by the formula:

(wherein R⁵ represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl), and q is an integer of 0 or 1;

U represents a group represented by the formula: —O— or —S—, or a group represented by the formula:

(wherein R⁶ represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl), and w is an integer of 0 or 1;

V represents a group represented by the formula: —O— or —S—, or a group represented by the formula:

[wherein R⁷ represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl, optionally substituted alkynyl or a group represented by the formula:

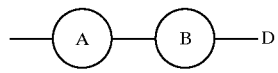

(wherein A and B each independently represent an optionally substituted aromatic hydrocarbon ring or an optionally substituted unsaturated heterocycle, and D represents optionally protected carboxyl)], and v is an integer of 0 or 1; and W represents a group represented by the formula: —O— or —S—, or a group represented by the formula:

[wherein R⁸ represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl, optionally substituted alkynyl or a group represented by the general formula:

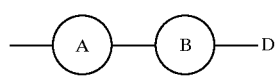

(wherein A and B each independently represent an optionally substituted aromatic hydrocarbon ring or an optionally substituted unsaturated heterocycle, and D represents optionally protected carboxyl)], and w is an integer of 0 or 1;

with the provisos that the symbol === in the formula:

employed in the above definition of X, Y, Z, P, Q, U, V and W represents a single bond or a double bond, that two of R¹, R², R³, R⁴, R⁵, R⁶, R⁷ and R⁸ adjacent to each other together with the carbon atoms to which they are bonded respectively may form a ring which may contain a heteroatom or be substituted, that x, y, z and p must satisfy the relationship: $4 \geq x+y+z+p \geq 3$, and u, v, w and q must satisfy the relationship: $4 \geq u+v+w+q \geq 3$, that either of V and W is a group of the formula:

(wherein $R^k$ refers to $R^7$ or $R^8$), wherein $R^7$ or $R^8$ is a group represented by the formula:

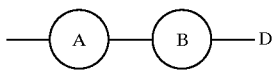

(wherein A and B each independently represent an optionally substituted aromatic hydrocarbon ring or an optionally substituted unsaturated heterocycle, and D represents optionally protected carboxyl), and that the compounds represented by the formula (A) wherein the ring L is completely saturated are excepted{.

Further, the present invention provides a medicament composition comprising a pharmacologically effective amount of the above carboxylic acid derivative having a fused ring or a pharmacologically acceptable salt thereof or a hydrate of the salt and a pharmacologically acceptable carrier.

Furthermore, the present invention provides a retinoic acid receptor agonist which is the above carboxylic acid derivative having a fused ring or a pharmacologically acceptable salt thereof or a hydrate of the salt.

The present invention also relates to a preventive and therapeutic agent for diseases against which retinoic acid receptor agonism is efficacious.

Additionally, the present invention provides a method for the prevention and treatment of diseases against which the retinoic acid receptor agonism is efficacious by administering a pharmacologically effective amount of the above carboxylic acid derivative having a fused ring or a pharmacologically acceptable salt thereof or a hydrate of the salt to a patient with such diseases, and use of the above carboxylic acid derivative having a fused ring or a pharmacologically acceptable salt thereof or a hydrate of the salt in preparing a remedy for diseases against which the retionic acid receptor agonism is efficacious.

DETAILED DESCRIPTION OF THE INVENTION

In the above definition of the formula (A), the term "halogens" used in the definition of $R^1$, $R_2$, $R^3$, $R^4$, $R^5$, $R^6$, $R^7$ and $R^8$ refers to fluorine, chlorine, bromine or iodine.

The term "lower alkyl" used in the definition of $R^1$, $R^2$, $R^3$, $R^4$, $R^5$, $R^6$, $R^7$ and $R^8$ refers to a linear or branched alkyl group having 1 to 6 carbon atoms. Examples thereof include methyl, ethyl, n-propyl, isopropyl, n-butyl, isobutyl, sec-butyl, tert-butyl, n-pentyl, 1,2-dimethylpropyl, 1,1-dimethylpropyl, 2,2-dimethylpropyl, 2-ethylpropyl, n-hexyl, 1,2-dimethylbutyl, 2,3-dimethylbutyl, 1,3-dimethylbutyl, 2,2-dimethylbutyl, 3,3-dimethylbutyl, 1,1-diethylpropyl, 2,2-diethylpropyl, 1,2-diethylpropyl, 1-ethyl-2-methylpropyl, 1-methyl-2-ethylpropyl and 1,1-diethylethyl. These alkyl groups may be substituted with one to three halogen atoms such as fluorine, chlorine, bromine or iodine atoms. That is, the above linear or branched lower alkyl group includes also trifluoromethyl, dibromoethyl and so on.

The term "cycloalkyl" used in the definition of $R^1$, $R^2$, $R^3$, $R^4$, $R^5$, $R^6$, $R^7$ and $R^8$ refers to one having 3 to 8 carbon atoms, and examples thereof include cyclopropyl, cyclobutyl, cyclopentyl, cyclohexyl, cycloheptyl and cyclooctyl.

The term "lower alkoxy" used in the definition of $R^1$, $R^2$, $R^3$, $R^4$, $R^5$, $R^6$, $R^7$ and $R^8$ refers to a linear or branched alkoxy group having 1 to 6 carbon atoms. Examples thereof include methoxy, ethoxy, n-propoxy, isopropoxy, n-butoxy, sec-butoxy, tert-butoxy, n-pentyloxy, 1,2-dimethylpropyloxy, 1,1-dimethylpropyloxy, 2,2-dimethylpropyloxy, 2-ethylpropyloxy, n-hexyloxy, 1,2-dimethylbutyloxy, 2,3-dimethylbutyloxy, 1,3-dimethylbutyloxy, 1-ethyl-2-methylpropyloxy and 1-methyl-2-ethylpropyloxy. Further, these alkoxy groups may be substituted with one to three halogen atoms such as fluorine, chlorine, bromine or iodine atoms. That is, the above lower alkoxy group includes also trifluoromethoxy, dibromoethoxy and so on.

As defined above, $R^1$, $R^2$, $R^3$, $R^4$, $R^5$, $R^6$, $R^7$ and $R^8$ may be optionally substituted aryl, and the term "aryl" used in this case refers to phenyl, 1-naphthyl, 2-naphthyl, anthracenyl or the like.

As defined above, A and B may be each an optionally substituted aromatic hydrocarbon ring, and the term "aromatic hydrocarbon ring" used in this case refers to benzene ring, naphthalene ring, anthracene ring or the like.

The term "optionally substituted heteroaryl" used in the definition of $R^1$, $R^2$, $R^3$, $R^4$, $R^5$, $R^6$, $R^7$ and $R^8$ refers to a group derived from a monocyclic or fused ring containing one to four sulfur, oxygen or nitrogen atoms. Examples thereof include thienyl, furyl, benzothienyl, benzofuranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, isoquinolinyl, quinolyl, phthalazinyl, quinoxalinyl, naphthyridinyl, quinazolinyl, acridinyl and furazanyl.

As defined above, A and B may be each an optionally substituted heterocycle, and the term "heterocycle" used in this case refers to a monocyclic or fused ring containing one to four sulfur, oxygen and/or nitrogen atoms. Examples thereof include thiophene ring, furan ring, benzothiophene ring, benzofuran ring, isobenzo- furan ring, pyrrole ring, imidazole ring, pyrazole ring, isothiazole ring, isoxazole ring, isoindole ring, indole ring, isoquinoline ring, quinoline ring, phthalazine ring, quinoxaline ring, naphthyridine ring, quinazoline ring, acridine ring and furazan ring.

As defined above, $R^1$, $R^2$, $R^3$, $R$ , $R^5$, $R^6$, $R^7$ and $R^8$may be each optionally substituted arylalkyl, and the term "aryl" used in this case refers to the same one defined above. Further, the term "alkyl" used in this case refers to the same one defined above with respect to the lower alkyl.

The term "optionally substituted heteroarylalkyl" used in the definition of $R^1$, $R^2$, $R^3$, $R^4$, $R^5$, $R^6$, $R^7$ and $R^8$ refers to a group obtained by bonding the above heteroaryl group to any carbon atom of the above alkyl group.

The substituent constituting the above optionally substituted aryl, heteroaryl, arylalkyl or heteroarylalkyl group includes linear and branched lower alkyl groups such as methyl, ethyl, n-propyl and isopropyl; linear and branched lower alkoxy groups such as methoxy, ethoxy, n-propoxy and isopropoxy; halogeno groups such as fluorine, chlorine, bromine and iodine; optionally substituted aryl groups; optionally substituted heteroaryl groups; optionally substituted arylalkyl groups; optionally substituted heteroarylalkyl groups; halogeno groups; hydroxy; hydroxyalkyl groups; alkoxyalkyl groups; and so on.

As described above, D is optionally protected carboxyl, and examples of the protecting group for this carboxyl group include lower alkyl groups such as methyl, ethyl and t-butyl; optionally substituted phenylated lower alkyl groups such as p-methoxybenzyl, p-nitrobenzyl, 3,4-dimethoxybenzyl, diphenylmethyl, trityl and phenethyl; halogenated lower alkyl groups such as 2,2,2-trichloroethyl and 2-iodoethyl; lower alkanoyloxy lower alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy lower alkyl groups such as palmitoyloxyethyl, heptadecanoyloxymethyl and 1-palmitoyloxyethyl; lower alkoxycarbonyloxy lower alkyl groups such as methoxycarbonyloxymethyl, 1-butoxycarbonyloxyethyl and 1-(isopropoxycarbonyloxy) ethyl; carboxylated lower alkyl groups such as carboxymethyl and 2-carboxyethyl; heteroaryl groups such as 3-phthalidyl; optionally substituted benzoyloxy lower alkyl groups such as 4-glycyloxybenzoyloxymethyl; (substituted dioxolene) lower alkyl groups such as (5-methyl-2-oxo-1, 3-dioxolen-4-yl)methyl; cycloalkylated lower alkanoyloxy lower alkyl groups such as 1-cyclohexylacetyloxyethyl; cycloalkyloxycarbonyloxy lower alkyl groups such as 1-cyclohexyloxycarbonyloxyethyl; and optionally substituted amino groups. That is, the term "optionally protected carboxyl" refers to carboxyl or a group which can be cleaved either by chemical means or in vivo to give a carboxylic acid.

Examples of the pharmacologically acceptable salt according to the present invention include inorganic salts such as hydrochlorides, hydrobromides, sulfates and phosphates; organic acid salts such as acetates, maleates, tartrates, methanesulfonates, benzenesulfonates and toluenesulfonates; and amino acid salts such as aspartates and glutamates.

When the compounds according to the present invention are present as optical isomers, the present invention includes also such optical isomers.

The compounds according to the present invention can readily be prepared by conventional processes or combinations of two or more of them. An example of the preparation process will now be described.

Preparation Process 1

Compounds represented by the formula (A) wherein A is a pyrrole ring can be prepared by the following process.

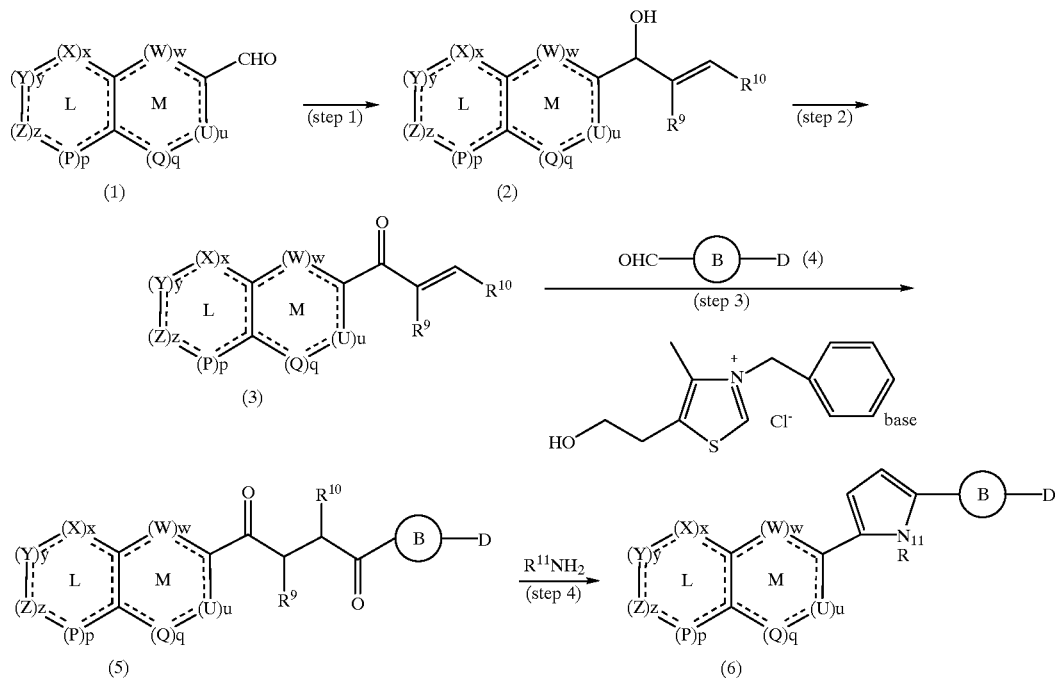

In this step, an allyl alcohol (2) is prepared by reacting an aldehyde (1) with an organometallic reagent in a conventional manner.

The organometallic reagent includes Grignard reagents, organolithium reagents, organozinc reagents, organocopper complexes and soon. Although any solvent inert to the reaction may be used in this step, the use of an etheric solvent such as ether or tetrahydrofuran is preferable. The reaction temperature may range from −78° C. to the boiling point of the solvent, preferably from about −78° C. to 20° C. (Step 2)

In this step, the allyl alcohol (2) prepared in the step (1) is oxidized into a vinyl ketone (3) in a conventional manner.

Although the oxidation may be conducted by any conventional process, the use of a suitable oxidizing agent is preferable. Examples of the oxidizing agent include activated manganese dioxide, pyridinium chlorochromate, pyridinium dichromate, Dess-Martin reagent and Swern oxidation reagent. Although any organic solvent inert to the reaction may be used for the oxidation, the use of dichloromethane, chloroform or acetone is preferable. The reaction temperature may range from about −78° C. to the boiling point of the solvent, preferably from about −78° C. to 20° C.
(Step 3)

In this step, a diketone represented by the formula (5) is prepared from the vinyl ketone (3) prepared in the step (2) and an aldehyde (4) according to the process of Stetter et al. described in Org. Synth. 65, 26.

In this step, better results can be attained by using a thiazolium salt catalyst. In such a case, it is preferable to use triethylamine, sodium acetate or the like as the base. Further, the solvent to be used in the above reaction may be methanol, ethanol, N,N-dimethylformamide or the like. The reaction temperature is preferably about 60° C. to the boiling point of the solvent.

(Step 4) In this step, the diketone (5) prepared in the step 3 is converted into a pyrrole represented by the formula (6) through a conventional treatment.

The objective compound (6) can be prepared by, for example, reacting the diketone (5) with an ammonium salt such as ammonium acetate or a primary amine. In this case, an alcoholic solvent such as methanol or ethanol or acetic acid may be used as the solvent. The reaction temperature is preferably about 70° C. to the boiling point of the solvent.

(Step 5)

In this step, the pyrrole (6) prepared in the step 4 is conventionally hydrolyzed into a final objective compound represented by the formula (7). In this step, better results can be attained by using a base, particularly an aqueous solution of lithium hydroxide, sodium hydroxide, potassium hydroxide or the like. Preferable examples of the solvent to be used in this hydrolysis include alcohols such as methanol and ethanol and ethers such as tetrahydrofuran. The reaction temperature is preferably about 20° C. to the boiling point of the solvent.

Next, another process is described with respect to the preparation of the diketone (5) used in the above Preparation process 1.

Preparation Process 1'

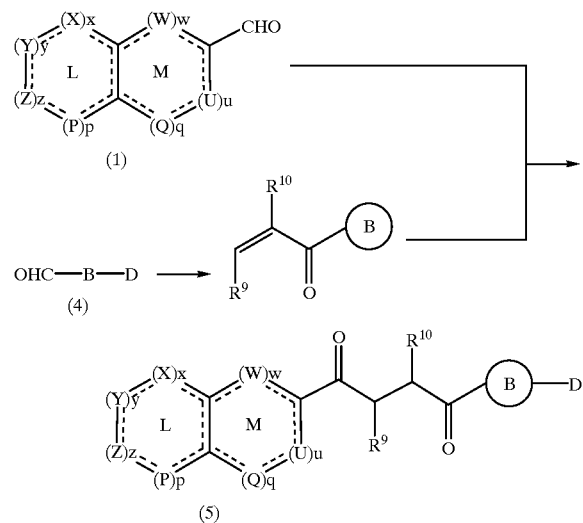

The diketone (5) can be prepared also by reacting the vinyl ketone (8) prepared in a similar manner to that of Preparation process 1 with the aldehyde (1) in the presence of a thiazolium salt catalyst according to the process of Stetter et al. In this process, better results can be attained by using as the base triethylamine, sodium acetate or the like. The solvent to be used in this process includes alcohols such as methanol and ethanol, N,N-dimethylformamide and so on. The reaction temperature is preferably about 60° C. to the boiling point of the solvent.

Pharmacological Experimental Examples will now be described to illustrate the effects of the present invention.

Pharmacological Experimental Example 1
Receptor Binding Assay Using Nuclear Extract Fraction of Cells Hearing RAR Genes Transferred Thereinto Human RAR $\alpha$, $\beta$ and $\gamma$ genes were transferred into BHK (Baby Hamster Kidney) cells to prepare cells constantly expressing RAR $\alpha$, $\beta$ and $\gamma$ proteins. An experimental system for measuring the specific binding of all-trans retinoic acid for RARs was constructed by the use of a nuclear extract fraction of the cells, and the abilities of each compound to bind RARs were determined by measuring the inhibition against the specific binding. Further, the selectivity of each compound among RARs was determined by comparing the abilities of the compound to bind RARs with each other.

(1) Experimental Method
a) Preparation of Nuclear Extract Fraction

The above BHK cells ($5\times10^8$) into which RAR genes had been transferred were suspended in 15 ml of solution A (sodium phosphate (pH7.4): 5 mM, monothioglycerol:10 mM, glycerol: 10% (v/v), phenylmethylsulfonyl fluoride (PMSF): 1 mM, aprotinin: 10 $\mu$g/ml, and leupeptin: 25 $\mu$g/ml). The resulting suspension was homogenized and centrifuged to remove the resulting supernatant. The resulting sediment was suspended in 15 ml of solution B (Tris-HCl (pH8.5): 10 mM, monothioglycerol: 10 mM, glycerol: 10% (v/v), PMSF: 1 mM, aprotinin: 10 $\mu$g/ml, leupeptin: 25 $\mu$g/ml, and KCl: 0.4 M). The resulting suspension was allowed to stand at 4° C. for one hour, and subjected to ultracentrifugation under the conditions of 100,000×g, 4° C. and one hour. The resulting supernatant was stored as the nuclear extract fraction in a frozen state at −80° C. until the use (METHODS IN ENZYMOLOGY, 189, 248).

b) Receptor Binding Assay

180 $\mu$l of the above fraction and 10 $\mu$l of a dilution of all-trans retinoic acid or a test compound were added to each well of a 96-well plate made of polypropylene, followed by the addition of 10 $\mu$l of 10 nM $^3$H-all-trans retinoic acid. The resulting plate was allowed to stand at 4° C. for 16 hours. A solution containing 3% of charcoal and 0.3% of dextran was added to the resulting reaction mixture. The resulting mixture was centrifuged to remove free $^3$H-all-trans retinoic acid. The radioactivity of the resulting supernatant was determined by the use of a scintillation counter. The specific binding for each RAR was determined by assuming the radioactivity found when 500 times as much all-trans retionic acid was added to be the non-specific binding and subtracting it from the radioactivity determined above. The compounds which will be described below inhibited the binding of $^3$H-all-trans retinoic acid dependently on the concentration.

(2) Experimental Results

The concentration at which the binding of $^3$H-all-trans acid for each receptor is inhibited by 50%, i.e., IC50 was calculated from the specific binding for the RAR, and the activities are given in Table 1, which were calculated from the IC50 value of all-trans retinoic acid to be 1.

TABLE 1

Results of receptor binding assay

| | Receptor binding assay Relative IC50 | | |
|---|---|---|---|
| Ex. No. | RAR-$\alpha$ | RAR-$\beta$ | RAR-$\gamma$ |
| All-trans retinoic acid | 1 | 1 | 1 |

TABLE 1-continued

Results of receptor binding assay

| Ex. No. | Receptor binding assay Relative IC50 | | |
|---|---|---|---|
| | RAR-α | RAR-β | RAR-γ |
| 1 | 24 | — | — |
| 4 | 119 | — | 649 |
| 6 | 15 | — | — |
| 7 | N.T. | N.T. | N.T. |
| 13 | 1.4 | 479 | — |
| 14 | 1.4 | 980 | — |
| 15 | 3.3 | — | — |
| 16 | <1.0 | 408 | 467 |
| 17 | <0.76 | 485 | 931 |
| 20 | 0.8 | 697 | — |
| 23 | 1.5 | 980 | 943 |
| 25 | 0.8 | 490 | 943 |
| 27 | 2.4 | — | — |
| 42 | 5.4 | 980 | — |
| 46 | 1.3 | 246 | 456 |
| 47 | <1.0 | 49 | 353 |
| 50 | 14.5 | — | — |
| 53 | 1.5 | — | — |
| 55 | 1.3 | 740 | — |
| 60 | 4.4 | — | — |
| 75 | 3.2 | 960 | — |
| 77 | 7.3 | — | — |
| 90 | 6.7 | — | — |
| 110 | 2.1 | 960 | — |
| 113 | N.T. | N.T. | N.T. |
| 127 | 9.7 | — | — |
| 129 | 69 | — | — |
| 133 | 27 | — | — |
| 147 | 1.7 | — | — |

N.T.: Not tested
—; >1000

Pharmacological Experimental Example 2
Measurement of the Activities of Accelerating Transcription Through RARs Human RAR Expression Vectors and secretory alkaline phosphatase (PLAP) gene vectors (PLAP vectors) containing in a state integrated into the upstream a competent sequence whose expression is inhibited through binding with RAR depending on a ligand were temporarily transferred into COS-1 (African green monkey kidney cells), and the PLAP which had been produced depending on a ligand and secreted into a culture medium was analyzed by the chemiluminescence method to determine the transcription-accelerating activity of each compound. Further, the selectivity of each compound among RARs was determined by comparing the transcription accelerating activities of the compound for the receptors with each other.

(1) Experimental Method

On a 60-mm culture dish were scattered $2.5 \times 10^4$ COS-1 cells. Four days after, human RAR α, β and γ expression vectors and PLAP vectors were transferred into the cells each in an amount of 4 μg by the lipofection method. Another day after, the resulting cells were recovered, and put on a 96-well culture plate in an amount of $2 \times 10^4$ per unit well. Four hours after, the cells were put on a medium containing charcoal-treated fetal bovine serum, followed by the addition of a dilution of all-trans retinoic acid or a test compound. After the lapse of 36 hours, the supernatant was recovered and the resulting samples were treated at 65° C. for 10 minutes to eliminate the non-specific activity. 15 μl of each sample was mixed with 60 μl of a 28 mM sodium carbonate buffer(pH10), followed by the addition of 75 μl of Smilight (trade name, a product of Sumitomo Metal Industries, Ltd., substrate for chemiluminescence). The resulting mixture was reacted at 37° C. for 30 minutes and the intensity of luminescence was determined. The compounds which will be described below induced the transcription activities of RARs dependently on the concentration.

(2) Experimental Results

With the transcription activity induced by 1 μM all-trans retinoic acid being assumed to be 100%, the concentration at which 30% of the activity is exhibited, i.e., ED30 was calculated for each compound. The relative activities of the compounds for each receptor are given in Table 2, which were calculated by assuming the ED30 value of all-trans retinoic acid to be 1.

TABLE 2

Transcription accelerating activity

| Ex. No. | Transcription accelerating activity Relative ED30 | | |
|---|---|---|---|
| | RAR-α | RAR-β | RAR-γ |
| All-trans retinoic acid | 1 | 1 | 1 |
| 1 | 1.6 | 150 | 1704 |
| 4 | 49 | — | — |
| 6 | 0.9 | 110 | 240 |
| 7 | 0.9 | 36 | 190 |
| 13 | 0.4 | 13 | 48 |
| 14 | 1.0 | 160 | 1400 |
| 15 | 3.1 | 940 | 2100 |
| 16 | 1.0 | 74 | 410 |
| 17 | 0.26 | 24 | 120 |
| 20 | 0.66 | 59 | 300 |
| 23 | 0.40 | 67 | 330 |
| 25 | 0.65 | 62 | 63 |
| 27 | 0.63 | 170 | 1000 |
| 42 | 0.33 | 91 | 790 |
| 46 | 0.63 | 14 | 240 |
| 47 | 0.80 | 2.4 | 41 |
| 50 | 0.38 | 280 | 710 |
| 53 | 0.17 | 26 | 430 |
| 55 | 0.20 | 31 | 120 |
| 60 | 0.72 | 110 | 750 |
| 75 | 0.80 | 150 | 2000 |
| 77 | 0.35 | 65 | 130 |
| 90 | 3.1 | 450 | 1400 |
| 110 | 0.47 | 210 | 790 |
| 113 | 0.80 | 24 | 150 |
| 127 | 1.8 | 240 | 3600 |
| 129 | 4.4 | 1050 | 2400 |
| 133 | 3.2 | 250 | 780 |
| 147 | N.T. | N.T | N.T |

N.T.: Not tested
—; >4000

The above Pharmacological Experimental Examples have revealed that the carboxylic acid derivatives represented by the formula (A) or pharmacologically acceptable salts thereof exhibit retinoic acid receptor agonism. Accordingly, the derivatives according to the present invention are useful as preventive and therapeutic agents for diseases against which the retinoic acid receptor agonism is efficacious. That is, the derivatives are usable as preventive and therapeutic agents for various cornification anomalies and skin diseases such as xeroderma pigmentosum, psoriasis, arthropathia psoriatica, acne or leukoplakia; various alopeciae such as alopecia areata, seborrheic alopecia or cachectic alopecia; various osteoporoses and osteopeniae such as postmenopausal osteoporosis, senile osteoporosis, steroidal osteoporosis, idiopathic osteoporosis, diabetic osteopenia, rheumatoid osteopenia or renal osteomalacia; diseases of bone and joint such as ectopic hyperostosis, osteoarthritis or shoulder periarthritis; autoimmune diseases such as chronic rheumatoid arthritis, multiple sclerosis, systemic lupus erythematosus, Behcet's disease, mycosis fungoides, systemic scleroderma, sudden thrombo-cytopenic purpura, myasthenia gravis, dermatomyositis or nodular arteriosclerosis; various leukemiae such as acute promyelocytic leukemia, acute myelocytic leukemia or chronic leukemia; rejections of graft in organ transplantation; graft versus host diseases (GVHD) in born marrow transplantation or stem cell transplantation; nephropathies such as nephrotic syndrome; glomerulonephritis; malignant lymphomas such as mycosis fungoides; squamous cell carcinomas such as squamous cell carcinoma of head and neck; solid carcinomas such as bladder cancer, pulmonary cancer, esophageal carcinoma, head and neck carcinoma, large bowel cancer, prostatic cancer or pancreatic cancer; inflammations and allergic diseases such as atopic dermatitis or asthma; immune deficiencies and intractable infections such as immunodeficiency diseases, infections with cytomegalovirus due to lowered immune function or of fetus or opportunistic infection; hyperthyroidism; hypercalcemia; various fibroses such as pulmonary fibrosis, hepatic fibrosis or hepatic cirrhosis; atherosclerosis and restenosis after reconstructive operation of blood circulation; other nonmalignant hyperplastic diseases such as endometrial hyperplasia, benign prostatic hypertrophy, proliferative vitreoretinopathy and dysplasia; diseases related to metabolism and transport of lipid such as hyperlipidemia; diabetes; wounds; dry eye syndrome; or solar skin injury; and as apoptosis induction accelerators.

The compounds of the present invention are lowly toxic and highly safe, being useful also in this respect.

When the compounds of the present invention are to be administered for the above diseases, the route of administration may suitably be selected. Specifically, they may be orally administered as preventive or therapeutic agents in the form of tablets, powders, granules, capsules, syrups or the like, or may be parenterally administered in the form of suppositories, injections, external preparations or drops.

Although the dosage of the compound remarkably depends on the kind of diseases, the extent of symptom, the interval from sideration to the first administration, the age, sex and sensitivity of patient or the like, the compound may be administered generally in a dosage of about 0.03 to 1000 mg, preferably 0.1 to 500 mg, still preferably of 0.1 to 100 mg per adult a day in several portions.

When the compound is to be administered as an injection, the dosage of the compound is generally about 1 to 3000 $\mu$g/kg, preferably about 3 to 1000 $\mu$g/kg.

The compounds of the present invention may be formulated into pharmaceutical preparations by the use of conventional preparation carriers according to conventional processes.

Specifically, a solid pharmaceutical preparation for oral administration according to the present invention can be formulated by adding a filler, binder, disintegrator, lubricant, colorant, corrigent, antioxidant and so on to a principal agent, and shaping the obtained mixture into tablets, coated tablets, granules, powders, capsules or the like according to conventional processes.

Examples of the filler include lactose, corn starch, sucrose, glucose, sorbitol, crystalline cellulose and silicon dioxide.

Examples of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin, and those of the lubricant include magnesium stearate, talc, polyethylene glycol, silica and hardened vegetable oils.

The colorant includes those authorized as pharmaceutical additives. The corrigent includes cocoa powder, menthol, aromatic powder, mentha oil, borneol, powdered cinnamic bark and so on. The antioxidant includes those authorized as pharmaceutical additives, for example, ascorbic acid and $\alpha$-tocopherol. Of course, the tablets and granules may be coated with sugar, gelatin or the like at need.

An injection according to the present invention can be formulated by a conventional process which comprises adding a pH regulator, buffer, suspending agent, solubilizing agent, stabilizer, tonicity agent, antioxidant and/or preservative to a principal agent at need and, if necessary, freeze-drying the resulting mixture. Such an injection may be administered intravenously, subcutaneously or intramuscularly.

Examples of the suspending agent include methylcellulose, polysorbate 80, hydroxyethylcellulose, acacia, tragacanth powder, carboxymethylcellulose sodium and polyoxyethylene sorbitan monolaurate.

The solubilizing agent includes polyoxyethylene hardened castor oil, polysorbate 80, nicotinamide, polyoxyethylene sorbitan monolaurate and so on.

Examples of the stabilizer include sodium sulfite, sodium metasulfite and ether. Examples of the preservative include methyl p-hydroxybezoate, ethyl p-hydroxybenzoate, sorbic acid, phenol, cresol and chlorocresol.

EXAMPLES

Examples will now be given to facilitate the understanding of the present invention, though it is needless to say that the present invention is not limited by them. The spectral data of nuclear magnetic resonance spectroscopy given below are those determined by the use of Varian UNITY 400 (400 MHz) spectrometer.

Prior to Examples illustrating the preparation of compounds according to the present invention, the preparation of starting compounds will be described as Preparative Examples. Although the preparation of some compounds according to the present invention is described as Preparative Examples for the sake of convenience, it is needless to say that such measures do not limit the present invention at all.

Preparative Example 1

5,8-Dimethyl-2-naphthaldehyde

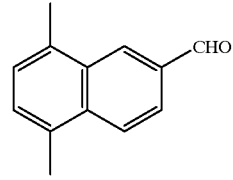

25 g of 5,8-dimethyltetralone was dissolved in 200 ml of methanol under nitrogen atmosphere, and 3.0 g of sodium borohydride was added to the resulting solution at 0° C. The resulting mixture was stirred at 0° C. for 30 minutes, and then a saturated aqueous solution of ammonium chloride and water were added to the resulting mixture in this order. The resulting precipitate was collected by filtration, washed with water and dried to give 23.7 g of an alcohol.

Under nitrogen atmosphere, 23.7 g of the alcohol was dissolved in 60 ml of N,N-dimethylformamide, and 25 ml of phosphorus oxychloride was added dropwise into the resulting solution at 0° C. After the completion of the addition, the reaction mixture was stirred under heating at 100° C. for 2 hours and cooled to room temperature by allowing to stand. Ice-water and 9 g of sodium acetate were added to the resulting mixture, and the resulting mixture was extracted with hexane (200 ml×4). The organic layers were combined, washed with brine, dried over anhydrous magnesium sulfate, and filtered. The resulting filtrate was concentrated to give 21.3 g of a crude aldehyde.

Under nitrogen atmosphere, 20.9 g of this crude aldehyde was dissolved in 300 ml of dioxane, followed by the addition of 50.9 g of dichlorodicyanobenzo-quinone. The resulting mixture was heated under reflux for 1.5 hours and cooled to room temperature by allowing to stand. Then, 500 ml of toluene was added to the resulting mixture to thereby form a precipitate. The resulting precipitate-containing mixture was filtered and the filter cake was washed with toluene several times. The filtrate was concentrated and the resulting crude product was purified by silica gel column chromatography to give 10.3 g of the title compound as colorless crystals.

$^1$H-NMR (CDCl$_3$, 400 MHz) δ; 2.69(s, 3H), 2.76(s, 3H), 7.31(d, 1H, J=7.2 Hz), 7.37(d, 1H, J=7.2 Hz), 7.99(dd, 1H, J=1.6, 8.8 Hz), 8.11(d, 1H, J=8.4 Hz), 8.51(d, 1H, J=1.6 Hz), 10.2(s, 1H).

Preparative Example 2

5,7-Dimethyl-2-naphthaldehyde

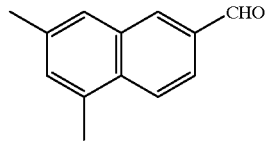

The title compound was obtained as an oil in a similar manner to that of Preparative Example 1 except that 5,7-dimethyl-1-tetralone was used as the starting compound.

$^1$H-NMR (CDCl$_3$, 400 MHz) δ; 2.50(s, 3H), 2.68(s, 3H), 7.32(s, 1H), 7.62(s, 1H), 7.91(dd, 1H, J=1.6, 8.4 Hz), 8.03(d, 1H, J=8.4), 8.23(d, 1H, J=1.6 Hz), 10.14(s, 1H).

Preparative Example 3

2-Cyano-5,6,7,8-tetramethylnaphthalene

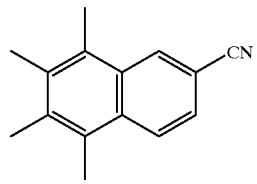

Under nitrogen atmosphere, 4.6 ml of diisopropylamine was dissolved in 30 ml of tetrahydrofuran, and a 1.6 M solution of n-butyllithium in hexane was added dropwise into the resulting solution at −20° C. Thus, LDA was obtained. A solution (10 ml) of 3.7 g of β-cyanopropionaldehyde dimethyl acetal in tetrahydrofuran was added dropwise into the LDA at −7° C., and the resulting mixture was stirred at the same temperature for one hour. Then, a solution (10 ml) of 4.7 g of 2,3,4,5-tetramethylbenzaldehyde in tetra-hydrofuran was added dropwise into the resulting mixture at −78° C., and the temperature of the reaction mixture was slowly raised to −20° C. The resulting mixture was quenched with a saturated aqueous solution of ammonium chloride and extracted with ethyl acetate (50 ml×3). The organic layers were combined, washed with brine, dried over anhydrous magnesium sulfate, and filtered. The resulting filtrate was concentrated to give a crude product. This crude product was purified by silica gel column chromatography to give 8.8 g of a benzyl alcohol as an oil.

The benzyl alcohol (1.0 g) was dissolved in 10 ml of methanol and the solution was added dropwise into 50 ml of a 20% aqueous solution of sulfuric acid under reflux over 10 minutes. The resulting mixture was further heated under reflux for one hour and then the reaction was ceased. The resulting reaction mixture was cooled to room temperature by allowing to stand, and extracted with ethyl acetate (50 ml×2). The organic layers were combined, washed with water, a saturated aqueous solution of sodium bicarbonate and brine successively, dried over anhydrous magnesium sulfate, and filtered. The filtrate was concentrated to give 0.65 g of the title compound as crude crystals.

$^1$H-NMR (CDCl$_3$, 400 MHz) δ; 2.45(s, 3H), 2.46(s, 3H), 2.62(s, 3H), 2.63(s, 3H), 7.56(dd, 1H, J=1.6, 8.8 Hz), 8.09(d, 1H, J=8.8 Hz), 8.42(d, 1H, J=1.6H).

Preparative Example 4

5,6,7,8-Tetramethyl-2-naphthaldehyde

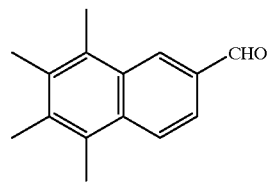

Under nitrogen atmosphere, 0.8 g of 2-cyano-5,6,7,8-tetramethylnaphthalene was dissolved in 30 ml of tetrahydrofuran, and 5.7 ml of a 1.0M solution of diisobutylaluminum hydride in hexane was added to the resulting solution at 0° C. The resulting mixture was stirred at room temperature for 2.5 hours, quenched with methanol and a saturated aqueous solution of ammonium chloride successively, and extracted with ethyl acetate (50 ml×2). The organic layers were combined, washed with brine, dried over anhydrous magnesium sulfate, and filtered. The resulting filtrate was concentrated and the resulting crude product was purified by silica gel column chromatography to give 0.68 g of the title compound as an oil.

$^1$H-NMR (CDCl$_3$, 400 MHz) δ; 2.46(s, 3H), 2.47(s, 3H), 2.65(s, 3H), 2.72(s, 3H), 7.90(dd, 1H, J=1.6, 8.8 Hz), 8.14(d, 1H, J=8.8 Hz), 8.55(d, 1H, J=1.6 Hz), 10.16(s, 1H).

Preparative Example 5

2-Cyano-7-methoxynaphthalene

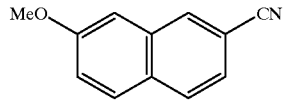

The title compound was prepared from m-anisaldehyde in a similar manner to that of Preparative Example 3.

$^1$H-NMR (CDCl$_3$, 400 MHz) δ; 3.94(s, 3H), 7.15(d, 1H, J=2.8 Hz), 7.28(dd, 1H, J=2.4, 9.2 Hz), 7.47(dd, 1H, J=1.6, 8.4 Hz), 7.78(d, 1H, J=9.2 Hz), 7.83(d, 1H, J=8.4 Hz), 8.11(s, 1H).

Preparative Example 6

7-Cyano-2-methoxy-1-naphthaldehyde

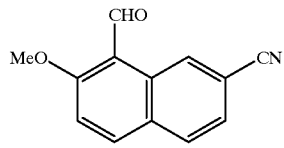

Under nitrogen atmosphere, 3.7 g of 2-cyano-7-methoxynaphthalene was dissolved in 40 ml of dichloromethane, and 6.6 ml of titanium tetrachloride and 4.6 ml of dichloromethyl methyl ether were added dropwise into the resulting solution at 0° in this order. The resulting mixture was stirred at room temperature for 30 minutes and cooled to 0° C. again. Water was added to the resulting mixture to cease the reaction, and the resulting mixture was extracted with dichloromethane (100 ml×2) The organic layers were combined, washed with water, a saturated aqueous solution of sodium bicarbonate and brine successively, dried over anhydrous magnesium sulfate, and filtered. The filtrate was concentrated and the resulting crude crystal was washed with ether and dried to give 3.3 g of the title compound as colorless crystals.

$^1$H-NMR (CDCl$_3$, 400 MHz) δ; 4.10(S, 3H), 7.48(d, 1H, J=8.8 Hz), 7.57(dd, 1H, J=1.2, 8.4 Hz), 7.86(d, 1H, J=8.4 Hz), 8.11(d, 1H, J=8.8 Hz), 9.74(s, 1H), 10.87(s, 1H).

Preparative Example 7

2-Cyano-7-methoxy-8-methylnaphthalene

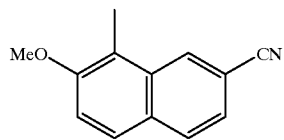

Under nitrogen atmosphere, 1.5 g of 7-cyano-2-methoxy-1-naphthaldehyde was suspended in 100 ml of ethanol, and 0.14 g of sodium borohydride was added to the resulting suspension at 0° C. The resulting mixture was stirred at room temperature for 2 hours and cooled to 0° C. again. The reaction was ceased by the addition of water and dilute hydrochloric acid, and the resulting mixture was extracted with ethyl acetate (100 ml×2). The organic layers were combined, washed with water, a saturated aqueous solution of sodium bicarbonate and brine successively, dried over anhydrous magnesium sulfate, and filtered. The filtrate was concentrated to give 1.5 g of an alcohol.

Under nitrogen atmosphere, 1.5 g of the alcohol was reacted with 7.5 ml of pyridine and 7.5 ml of acetic anhydride at room temperature for 12 hours, followed by the addition of water. The resulting mixture was extracted with ethyl acetate (100 ml×2). The organic layers were combined, washed with 2N hydrochloric acid, water, a saturated aqueous solution of sodium bicarbonate and brine successively, dried over anhydrous magnesium sulfate, and filtered. The filtrate was concentrated to give 1.9 g of an acetoxy compound as a colorless solid.

Then, 1.9 g of the acetoxy compound and 0.4 g of 10% palladium/carbon (containing 50% of water) were suspended in 200 ml of ethanol, and the resulting suspension was subjected to catalytic hydrogenation under normal pressure at ordinary temperature for 2 hours. The resulting reaction mixture was filtered through Celite, and the filtrate was concentrated. The resulting crude product was purified by silica gel column chromatography to give 1.1 g of the title compound as a colorless solid.

$^1$H-NMR (CDCl$_3$, 400 MHz) δ; 2.55(s, 3H), 3.97(s, 3H), 7.40(d, 1H, J=8.8 Hz), 7.45(dd, 1H, J=1.6, 8.4 Hz), 7.76.(d, 1H, J=8.8 Hz), 7.84(d, 1H, J=8.4 Hz), 8.34(m, 1H).

Preparative Example 8

7-Methoxy-8-methyl-2-naphthaldehyde

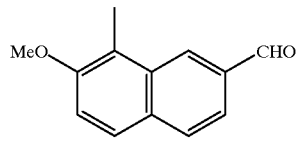

The title compound was obtained as a colorless solid by the use of 2-cyano-7-methoxy-8-methylnaphthalene in a similar manner to that of Preparative Example 4.

$^1$H-NMR (CDCl$_3$, 400 MHz) δ; 2.64(s, 3H), 3.98(s, 3H), 7.41(d, 1H, J=8.8 Hz), 7.78(d, 1H, J=9.2 Hz), 7.81(dd, 1H, J=1.2, 8.4 Hz), 7.87(d, 1H, J=8.4 Hz), 8.46(s, 1H), 10.17(s, 1H).

Preparative Example 9

2-Cyano-7-methoxy-8-ethylnaphthalene

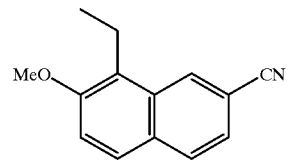

Under nitrogen atmosphere, 2.0 g of 7-cyano-2-methoxy-1-naphthaldehyde was suspended in 60 ml of tetrahydrofuran, and 4.7 ml of a 3.0M solution of methylmagnesium bromide in ether was added dropwise into the resulting suspension at −78° C. The resulting mixture was stirred at −78° for 2 hours, and then the reaction was ceased by the addition of a saturated aqueous solution of ammonium chloride. Water was added to the resulting mixture, and the resulting mixture was extracted with ethyl acetate (100 ml×2). The organic layers were combined, washed with brine, dried over anhydrous magnesium sulfate, and filtered. The filtrate was concentrated to give 2.2 g of an alcohol.

Under nitrogen atmosphere, 2.2 g of the alcohol was reacted with 10 ml of pyridine and 10 ml of acetic anhydride at room temperature for 12 hours, followed by the addition of water. The resulting mixture was extracted with ethyl acetate (100 ml×2). The organic layers were combined, washed with 2N hydrochloric acid, water, a saturated aqueous solution of sodium bicarbonate and brine successively, dried over anhydrous magnesium sulfate, and filtered. The filtrate was concentrated to give 2.2 g of an acetoxy compound as a colorless solid.

Then, 2.2 g of the acetoxy compound and 0.4 g of 10% palladium/carbon (containing 50% of water) were suspended in 200 ml of ethanol, and the resulting suspension was subjected to catalytic hydrogenation under normal pressure at ordinary temperature for 6.5 hours. The resulting reaction mixture was filtered through Celite, and the filtrate was concentrated. The resulting crude product was purified by silica gel column chromatography to give 0.86 g. of the title compound as a colorless solid.

$^1$H-NMR (CDCl$_3$, 400 MHz) δ; 1.23(t, 3H, J=7.6 Hz), 3.08(q, 2H, J=7.6 Hz), 3.98(s, 3H), 7.41(d, 1H, J=9.2 Hz), 7.44(dd, 1H, J=1.6, 8.4 Hz), 7.76(d, 1H, J=9.2 Hz), 7.84(d, 1H, J=8.4 Hz), 8.35(s, 1H).

Preparative Example 10

7-Methoxy-8-ethyl-2-naphthaldehyde

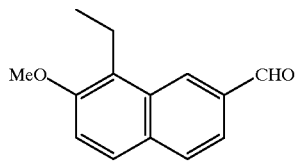

The title compound was obtained as a colorless solid by the use of 2-cyano-7-methoxy-8-ethylnaphthalene in a similar manner to that of Preparative Example 4.

$^1$H-NMR (CDCl$_3$, 400 MHz) δ; 1.27(t, 3H, J=7.6 Hz), 3.18(q, 2H, J=7.6 Hz), 3.98(s, 3H), 7.41(d, 1H, J=8.8 Hz), 7.78(d, 1H, J=9.2 Hz), 7.80(dd, 1H, J=1.2, 8.4 Hz), 7.88(d, 1H, J=8.4 Hz), 8.47(s, 1H), 10.18(s, 1H).

Preparative Example 11

2-Cyano-8-methylnaphthalene

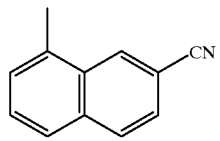

Under nitrogen atmosphere, 0.60 g of 2-cyano-7-methoxy-8-methylnaphthalene was dissolved in 10 ml of dichloromethane, and 6 ml of a 1.0M solution of boron tribromide in dichloromethane was added to the resulting solution at 0° C. The resulting mixture was stirred at room temperature for 24 hours, and cooled to 0° C. again. The reaction was ceased by the addition of water, and the resulting mixture was extracted with ethyl acetate (50 ml×2). The organic layers were combined, washed with a saturated aqueous solution of sodium bicarbonate and brine successively, dried over anhydrous magnesium sulfate, and filtered. The filtrate was concentrated, and the resulting crude product was purified by silica gel column chromatography to give 0.95 g of a triflate as a colorless solid.

Under nitrogen atmosphere, 0.85 g of the triflate, 35 mg of triphenylphosphine and 12 mg of palladium acetate were dissolved in 20 ml of anhydrous N,N-dimethylformamide, and 1.1 ml of triethylamine and 0.21 ml of formic acid were added dropwise into the resulting solution in this order. The obtained mixture was stirred under heating at 70° C. for 6 hours and cooled to room temperature by allowing to stand. The reaction was ceased by the addition of a saturated aqueous solution of ammonium chloride, followed by the addition of water. The resulting mixture was extracted with ethyl acetate (50 ml×2). The organic layers were combined, washed with brine, dried over anhydrous magnesium sulfate, and filtered. The filtrate was concentrated, and the crude product thus obtained was purified by silica gel column chromatography to give 0.95 g of another triflate as a colorless solid.

Under nitrogen atmosphere, 0.85 g of the triflate, 35 mg of triphenylphosphine and 12 mg of palladium acetate were dissolved in 20 ml of anhydrous N,N-dimethylformamide, followed by the addition of water. The resulting mixture was extracted with ethyl acetate (50 ml×2). The organic layers were combined, washed with brine, dried over anhydrous magnesium sulfate, and filtered. The filtrate was concentrated, and the resulting crude product was purified by silica gel column chromatography to give 0.42 g of the title compound as a colorless solid.

$^1$H-NMR (CDCl$_3$, 400 MHz) δ; 2.72(s, 3H), 7.44(d, 1H, J=6.8 Hz), 7.53(dd, 1H, J=7.2, 8.0 Hz), 7.62(dd, 1H, J=1.6, 8.4 Hz), 7.74(d, 1H, J=8.0 Hz), 7.91(d, 1H, J=8.4 Hz), 8.40(s, 1H).

Preparative Example 12

8-Methyl-2-naphthaldehyde

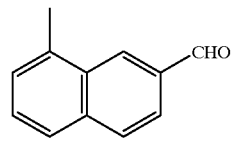

The title compound was obtained as a colorless solid by the use of 2-cyano-8-methylnaphthalene in a similar manner to that of Preparative Example 4.

$^1$H-NMR (CDCl$_3$, 400 MHz) δ; 2.79(s, 3H), 7.42(d, 1H, J=7.2 Hz), 7.53(dd, 1H, J=7.2, 8.0 Hz), 7.76(d, 1H, J=8.0 Hz), 7.93–7.97(m, 2H), 8.51(s, 1H), 10.19(s, 1H).

Preparative Example 13

2-Cyano-8-ethylnaphthalene

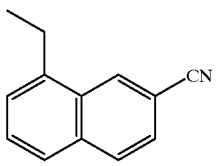

The title compound was obtained as an oil by the use of 2-cyano-7-methoxy-8-ethylnaphthalene in a similar manner to that of Preparative Example 11.

$^1$H-NMR (CDCl$_3$, 400 MHz) δ; 1.39(t, 3H, J=7.6 Hz), 3.12(q, 2H, J=7.6 Hz), 7.46(d, 1H, J=7.2 Hz), 7.56(dd, 1H, J=7.2, 8.0 Hz), 7.60(dd, 1H, J=1.6, 8.4 Hz), 7.74(d, 1H, J=8.0 Hz), 7.92(d, 1H, J=8.4 Hz), 8.45(s, 1H).

Preparative Example 14

8-Ethyl-2-naphthaldehyde

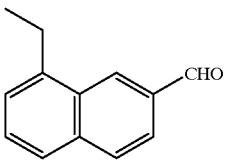

The title compound was prepared from 2-cyano-8-ethylnaphthalene in a similar manner to that of Preparative Example 4.

$^1$H-NMR (CDCl$_3$, 400 MHz) δ; 1.36(t, 3H, J=7.2 Hz), 3.14(q, 2H, J=7.2 Hz), 7.38(d, 1H, J=6.8 Hz), 7.50(dd, 1H, J=6.8, 8.4 Hz), 7.70(d, 1H, J=8.4 Hz), 7.88(d, 2H, J=1.2 Hz), 8.50(s, 1H), 10.12(s, 1H).

Preparative Example 15

7'-Cyano-2'-methoxy-1'-acetonaphthone

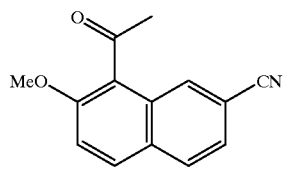

Under nitrogen atmosphere, 1.2 ml of oxalyl chloride was dissolved in 25 ml of dichloromethane, and a solution (5 ml) of 1.4 ml of dimethyl sulfoxide in di-chloromethane was added dropwise into the resulting solution at −78° C. Then, a solution (10 ml) of 1.99 g of the alcohol prepared in Preparative Example 7 in dichloromethane was added dropwise into the mixture prepared above at −78° C. The resultling mixture was stirred for 5 minutes, followed by the addition of 6.1 ml of triethylamine. The temperature of the resulting reaction mixture was raised to 0° C., and the reaction was ceased by the addition of water. The resulting mixture was extracted with ethyl acetate (150 ml×2), and the organic layers were combined, washed with brine, dried over anhydrous magnesium sulfate, and filtered. The filtrate was concentrated, and the crude crystal thus obtained was washed with hexane and dried to give 1.88 g of the title compound as a colorless solid.

$^1$H-NMR (CDCl$_3$, 400 MHz) δ; 2.67(s, 3H), 4.02(s, 3H), 7.44(d, 1H, J=9.2 Hz), 7.49(dd, 1H, J=2.0, 8.4 Hz), 7.87(d, 1H, J=8.4 Hz), 7.95(d, 1H, J=9.2 Hz), 8.22(m, 1H).

Preparative Example 16

2-Cyano-8-isopropenyl-7-methoxynaphthalene

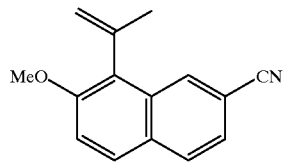

Under nitrogen atmosphere, 0.62 g of potassium t-butoxide was suspended in 10 ml of toluene, and 2.26 g of trimethylphosphonium iodide was added to the resulting suspension at room temperature. The resulting mixture was stirred under heating at 100° C. for one hour to give a yellow suspension. Then, 0.84 g of 7'-cyano-2'-methoxy-1'-acetonaphthone was added to the yellow suspension, and the resulting mixture was further stirred at 10° C. for 30 minutes, cooled to room temperature by allowing to stand, diluted with ethyl acetate, and filtered through Celite. The filtrate was washed with brine, dried over anhydrous magnesium sulfate, and filtered. The filtrate was concentrated, and the resulting crude product was purified by silica gel column chromatography to give 0.78 g of the title compound as an oil.

$^1$H-NMR (CDCl$_3$, 400 MHz) δ; 2.11(s, 3H), 3.98(s, 3H), 4.96(m,1 H) 5.58(m,1 H) 7.44(d,1H, J=8.8 Hz), 7.45(dd, 1H, J=1.6, 8.4 Hz), 7.83(d, 1H, J=9.2 Hz), 7.84(d, 1H, J=8.4 Hz), 8.37(m, 1H).

Preparative Example 17

2-Cyano-8-isopropenylnaphthalene

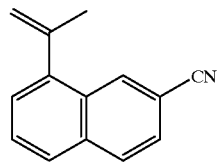

The title compound was obtained as an oil by the use of 2-cyano-8-isopropenyl-7-methoxynaphthalene in a similar manner to that of Preparative Example 11.

$^1$H-NMR (CDCl$_3$, 400 MHz) δ; 2.21(s, 3H), 5.06(m, 1H), 5.50(m, 1H), 7.43(d, 1H, J=7.2 Hz), 7.59(t, 1H, J=8.0 Hz), 7.59(dd, 1H, J=1.6, 8.4 Hz), 7.79(d, 1H, J=8.0 Hz), 7.91(d, 1H, J=8.4 Hz), 8.48(m, 1H).

Preparative Example 18

8-Isopropenyl-2-naphthaldehyde

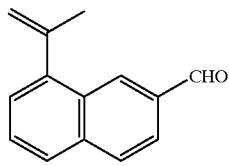

The title compound was obtained as an oil by the use of 2-cyano-8-isopropenylnaphthalene in a similar manner to that of Preparative Example 4.

$^1$H-NMR (CDCl$_3$, 400 MHz) δ; 2.25(s, 3H), 5.10(m, 1H), 5.51(m, 1H), 7.43(dd, 1H, J=1.2, 7.2 Hz) 7.60(dd, 1H, J=7.2, 8.0 Hz), 7.81(d, 1H, J=8.0 Hz), 7.94(m, 2H), 8.58(m, 1H), 10.15(m, 1H).

Preparative Example 19

2-Cyano-8-isopropylnaphthalene

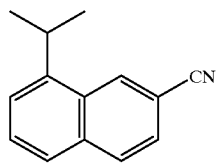

2-Cyano-8-isopropenylnaphthalene (0.23 g) and 10% palladium/carbon (containing 50% of water) (50 mg) were suspended in 20 ml of ethanol and the resulting suspension was subjected to catalytic hydrogenation at ordinary temperature under normal pressure for one hour. The reaction mixture was filtered through Celite, and the filtrate was concentrated to give a crude product. This crude product was purified by silica gel column chromatography to give 0.20 g of the title compound as an oil.

$^1$H-NMR (CDCl$_3$, 400 MHz) δ; 1.41(d, 6H, 6.8 Hz), 3.71(quint., 1H, J=6.8 Hz), 7.53(d, 1H, J=7.2 Hz), 7.60(d, 1H, J=8.4 Hz), 7.61(dd, 1H, J=7.2, 8.4 Hz), 7.74(d, 1H, J=8.4 Hz), 7.92(d, 1H, J=8.4 Hz), 8.53(s, 1H).

Preparative Example 20

8-Isopropyl-2-naphthaldehyde

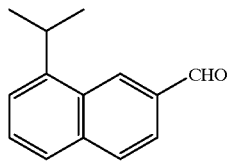

The title compound was obtained as an oil by the use of 2-cyano-8-isopropylnaphthalene in a similar manner to that of Preparative Example 4.

$^1$H-NMR (CDCl$_3$, 400 MHz) δ; 1.44(d, 6H, J=6.8 Hz), 3.86(quint., 1H, J=6.8 Hz), 7.53(d, 1H, J=7.2 Hz), 7.61(dd, 1H, J=7.2, 8.0 Hz), 7.76(d, 1H, J=8.4 Hz), 7.95(m, 2H), 8.65(s, 1H), 10.19(s, 1H).

Preparative Example 21

7-Cyano-2-methoxy-1-naphthol

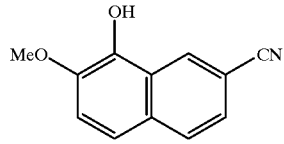

The title compound was obtained as a colorless solid by the use of 3-methoxy-2-methoxymethoxybenzaldehyde in a similar manner to that of Preparative Example 3.

$^1$H-NMR (CDCl$_3$, 400 MHz) δ; 4.03(s, 3H), 7.39(d, 1H, J=8.8 Hz), 7.44(d, 2H, J=8.8 Hz), 7.80(d, 1H, J=8.8 Hz), 8.55(m, 1H).

Preparative Example 22

2-Cyano-7-methoxy-8-trifluoromethanesulfonyloxynaphthalene

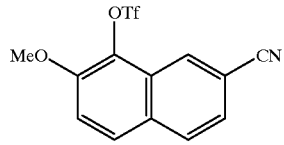

Under nitrogen atmosphere, 2.9 g of the naphthol was dissolved in 150 ml of dichloromethane, and 10.7 g of N,N-dimethylaminopyridine and 4.8 ml of trifluoromethanesulfonic anhydride were added to the resulting solution at 0° C. in this order. The resulting mixture was stirred at 0° C. for one hour, and the reaction was ceased by the addition of water. 6N Hydrochloric acid was added to the resulting mixture, followed by the extraction with ethyl acetate (500 ml×2). The organic layers were combined, washed with water, a saturated aqueous solution of sodium bicarbonate, and brine successively, dried over anhydrous magnesium sulfate, and filtered. The filtrate was concentrated, and the resulting crude product was purified by silica gel column chromatography to give 4.3 g of the title compound as a colorless solid.

$^1$H-NMR (CDCl$_3$, 400 MHz) δ; 4.08(s, 3H), 7.54(d, 1H, J=9.2 Hz), 7.58(dd, 1H, J1.6, 8.8 Hz), 7.93(d, 1H, J=8.8 Hz), 7.94(d, 1H, J=8.8 Hz), 8.30(s, 1H).

Preparative Example 23

2-Cyano-7-methoxy-8-phenylnaphthalene

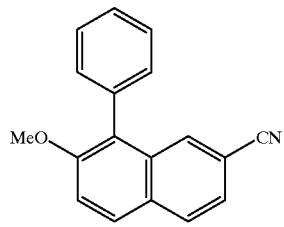

Under nitrogen atmosphere, 1.2 g of 2-cyano-7-methoxy-8-trifluoromethanesulfonyloxynaphthalene, 0.66 g of phenylboronic acid, 0.12 g of tetrakis triphenylphosphine palladium and 1.5 ml of triethyl- amine were suspended in 20 ml of anhydrous N, N-dimethylformamide. The resulting suspension was stirred under heating at 100° C. for 1.5 hours and cooled to room temperature by allowing to stand. A saturated aqueous solution of ammonium chloride was added to the resulting reaction mixture, followed by the extraction with ethyl acetate (50 ml×2). The organic layers were combined, washed with brine, died over anhydrous magnesium sulfate, and filtered. The filtrate was concentrated, and the resulting crude product was purified by silica gel column chromatography to give 0.95 g of the title compound.

$^1$H-NMR (CDCl$_3$, 400 MHz) δ; 3.87(s, 3H), 7.30–7.33(m, 2H), 7.43–7.55(m, 5H), 7.88(m, 1H), 7.89(d, 1H, J=8.4 Hz), 7.93(d, 1H, J=8.8 Hz).

Preparative Example 24

2-Cyano-8-phenylnaphthalene

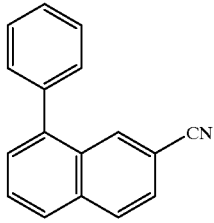

The title compound was obtained as a colorless solid by the use of 2-cyano-7-methoxy-8-phenylnaphthalene in a similar manner to that of Preparative Example 11.

$^1$H-NMR (CDCl$_3$, 400 MHz) δ; 7.43–7.56(m, 6H), 7.62 (dd, 1H, J=1.6, 8.4 Hz), 7.69(dd, 1H, J=7.2, 8.0 Hz), 7.90(d, $_1$H, J=8.4 Hz), 7.98(d, 1H, J=8.4 Hz), 8.29(m, 1H).

Preparative Example 25

8-Phenyl-2-naphthaldehyde

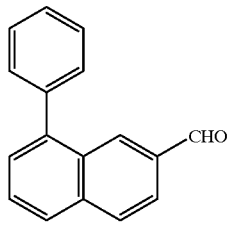

The title compound was obtained as a pale yellow oil by the use of 2-cyano-8-phenylnaphthalene in a similar manner to that of Preparative Example 4.

$^1$H-NMR (CDCl$_3$, 400 MHz) δ; 7.48–7.57(m, 6H), 7.69 (dd, 1H, J=7.2, 8.0 Hz), 7.92(d, 1H, J=8.4 Hz), 7.98(dd, 1H, J=1.2, 8.4 Hz), 8.00(d, 1H, J=8.4 Hz), 8.39(m, 1H), 10.02(s, 1H).

Preparative Example 26

Methyl 4-acryloylbenzoate

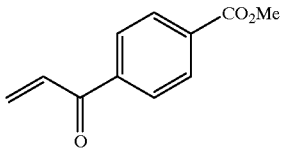

A 1.0 M solution (100 ml) of vinylmagnesium bromide in tetrahydrofuran was added dropwise into a solution of 13.6 g of methyl terephthalaldehydate in 150 ml of tetrahydrofuran at −78° C. The resulting mixture was stirred at the same temperature for 30 minutes, quenched with a saturated aqueous solution of ammonium chloride, and extracted with ethyl acetate (200 ml×2). The organic layers were combined, washed with brine, dried over anhydrous magnesium sulfate, and filtered. The filtrate was concentrated, and the resulting crude product was purified by silica gel column chromatography to give 11.6 g of an allyl alcohol.

Then, 11.6 g of the allyl alcohol was dissolved in 600 ml of dichloromethane, followed by the addition thereto of 3 g of molecular sieve (3A) and 27 g of pyridinium bichromate. The resulting mixture was stirred at room temperature for 4 hours, and filtered through Celite. The filtrate was concentrated, and the resulting crude product was purified by silica gel column chromatography to give 5.5 g of the title compound as colorless crystals.

$^1$H-NMR (CDCl$_3$, 400 MHz) δ; 3.96(s, 3H), 6.00(d, 1H, J=10.4 Hz), 6.46(d, 1H, J=17.2 Hz), 7.14(dd, 1H, J=10.4, 17.2 Hz), 7.98(d, 2H, J=8.4 Hz), 8.14(d, 2H, J=8.4 Hz).

Preparative Example 27

4,7-Dimethylbenzofuran-2-carbaldehyde

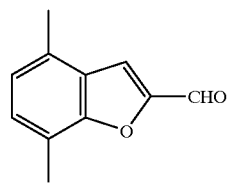

To 100 ml of a solution of 10 g of 2,5-dimethylphenol in N,N-dimethylformamide were added 22.6 g of anhydrous potassium carbonate and 14.8 ml of bromoacetaldehyde diethyl acetal. The resulting mixture was stirred under heating at 150° C. for 2.5 hours, cooled to room temperature by allowing to stand, and extracted with ethyl acetate. The organic layer was washed with brine, dried over anhydrous magnesium sulfate, and the solvent was evaporated. The resulting residue was purified by silica gel column chromatography to give 18 g of an ether as a colorless oil.

This ether was dissolved in 100 ml of toluene, followed by the addition of 50 g of polyphosphoric acid. The resulting mixture was stirred under heating at 90° C. under nitrogen atmosphere for one hour, cooled to room temperature by allowing to stand, and poured into ice-water. The resulting mixture was extracted with ethylacetate. The organic layer was washed with brine, dried over anhydrous magnesium sulfate, and the solvent was evaporated. The resulting residue was purified by silica gel column chromatography to give 3.5 g of 4,7-dimethylbenzofuran as a yellow oil.

Under nitrogen atmosphere at −35° C., 18.4 ml of n-butyllithium (1.56M hexane solution) was added to 50 ml of a solution of 3.5 g of 4,7-dimethylbenzofuran in anhydrous tetrahydrofuran, and the resulting mixture was stirred for 15 minutes, followed by the dropwise addition thereto of 5.6 ml of N,N-dimethylformamide. The temperature of the resulting mixture was raised to room temperature, followed by the addition of ethyl acetate. The organic layer was washed with brine, dried over anhydrous magnesium sulfate, and the solvent was evaporated. The resulting crude crystal was washed with n-hexane to give 2.3 g of the title compound as a pale-yellow solid.

$^1$H-NMR (CDCl$_3$, 400 MHz) δ; 2.53(s, 6H), 7.02(d, 1H, J=6.8 Hz), 7.20(d, 1H, J=6.8 Hz), 7.59(s, 1H), 9.85(s, 1H).

Preparative Example 28

4,7-Dimethylbenzofuran-2-carbaldehyde

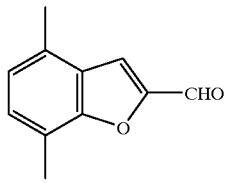

To 200 ml of a solution of 17.4 g of 3,6-dimethylsalicylaldehyde in N,N-dimethyformamide were added 32 g of anhydrous potassium carbonate and 17.8 ml of bromoacetaldehyde diethyl acetal. The resulting mixture was stirred at 150° C. for 2.5 hours, cooled to room temperature by allowing to stand, and extracted with ethyl acetate. The organic layer was washed with brine, dried over anhydrous magnesium sulfate, and the solvent was evaporated. The resulting residue was purified by silica gel column chromatography to give 23.4 g of an ether. This ether was dissolved in 120 ml of acetic acid. The resulting solution was refluxed under nitrogen stream for 8 hours, cooled to room temperature by allowing to stand, and poured into a saturated aqueous solution of sodium bicarbonate. The resulting mixture was extracted with ethyl acetate. The organic layer was washed with brine, dried over anhydrous magnesium sulfate, and the solvent was evaporated. The resulting crude product was washed with hexane to give 7.8 g of the title compound as a pale yellow solid.

Preparative Example 29

5-Fluoro-4,7-dimethylbenzofuran-2-carbaldehyde

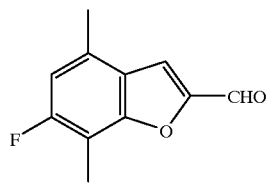

(A) 5-Fluoro-2-methoxy-4-methylbenzaldehyde

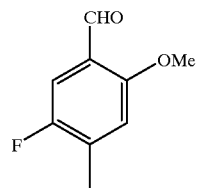

10 g of 4-fluoro-3-methylanisol was dissolved in 80 ml of dichloromethane, and 10 ml of titanium tetrachloride and 7.5 ml of dichloromethyl methyl ether were added to the solution successively at 0° C. The resulting mixture was stirred at the same temperature for 30 minutes. The reaction mixture was poured into ice-water, followed by the addition of 300 ml of ethyl acetate. The organic phase was washed with brine, dried over anhydrous magnesium sulfate. After the desiccant was filtered off, the resulting mixture was evaporated to give a solid. n-Hexane was added to this solid, and the resulting mixture was filtered. The filter cake was washed with n-hexane to give 5.8 g of the title compound as white crystals.

$^1$H-NMR (CDCl$_3$, 400 MHz) δ; 2.33(s, 3H), 3.88(s, 3H), 6.79(d, 1H, J=5.6 Hz), 7.44(d, 1H, J=9.6 Hz), 10.36(s, 1H).

(B) 4-Fluoro-2,5-dimethylanisole

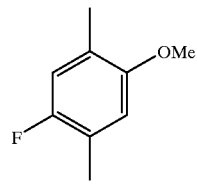

17.5 g of 5-fluoro-2-methoxy-4-methylbenzaldehyde was dissolved in 100 ml of methanol, 4.7 g of sodium borohydride was added to the suspension at 0° C. and the resulting mixture was stirred for 30 minutes. Acetone was added to the reaction mixture to decompose excess reagent. The resulting reaction mixture was evaporated and extracted with 150 ml of ethyl acetate. The organic layer was washed with brine, dried over anhydrous magnesium sulfate. After the desiccant was filtered off, the resulting mixture was evaporated to give white crystals. These crystals were dissolved in 50 ml of pyridine, followed by the addition of 19.6 ml of acetic anhydride. The resulting mixture was stirred at room temperature for 4 hours and poured into chilled dilute hydrochloric acid. The resulting mixture was stirred for 30 minutes, followed by the addition of ethyl acetate. The organic layer was separated, washed with water, a saturated aqueous solution of sodium bicarbonate and brine, dried over anhydrous magnesium sulfate. After the desiccant was filtered off, the resulting mixture was evaporated to give a solid. This solid was dissolved in 100 ml of ethyl acetate, followed by the addition of 3 g of 10% palladium/carbon (containing 50% of water). The resulting mixture was subjected to catalytic hydrogenation at ordinary temperature under normal pressure for 3 hours, and the resulting reaction mixture was filtered through Celite. The filtrate was concentrated, and the resulting crude product was purified by silica gel column chromatography to give 9.7 g of the title compound as a colorless oil.

$^1$H-NMR (CDCl$_3$, 400 MHz) δ; 2.16(s, 3H), 2.22(s, 3H), 3.77(s, 3H), 6.59(d, 1H, J=6.4 Hz), 6.78(d, 1H, J=10.0 Hz).

(C) 4-Fluoro-2,5-dimethylphenol

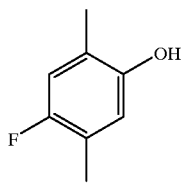

9.7 g of 4-fluoro-2,5-dimethylanisol was dissolved in 100 ml of dichloromethane and 76 ml of boron tribromide (1.0M dichloromethane solution) was added to the solution at 0° C. The resulting mixture was brought to room temperature, stirred for one hour, and poured into ice-water. 300 ml of ethyl acetate was added to the resultling mixture. The organic layer was washed with water, a saturated aqueous solution of sodium bicarbonate and brine successively, dried over magnesium sulfate. After the desiccant was filtered off, the resulting mixture was evaporated. The resulting crude product was purified by silica gel column chromatography to give 8.5 g of the title compound as a pale brown oil.

$^1$H-NMR (CDCl$_3$, 400 MHz) δ; 2.18(s, 6H), 4.41(s, 1H), 6.56(d, 1H, J=6.8 Hz), 6.76(d, 1H, J=10.0 Hz)

(D) 5-Fluoro-4,7-dimethylbenzofuran-2-carbaldehyde

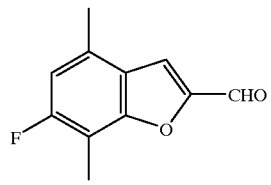

The title compound was prepared by the use of 4-fluoro-2,5-dimethylphenol as the starting compound in a similar manner to that of Preparative Example 27.

$^1$H-NMR (CDCl$_3$, 400 MHz) δ; 2.42(s, 6H), 2.53(s, 3H), 7.04(d, 1H, J=10.0 Hz), 7.58(s, 1H), 9.86(s, 1H).

Preparative Example 30

4,7-Diethyl-5-fluorobenzofuran-2-carbaldehyde

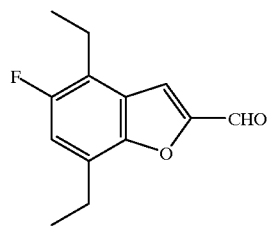

(A) 3-Ethenyl-4-fluoroanisole

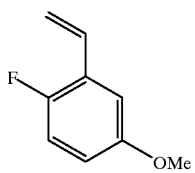

39.4 g of methyltriphenylphosphonium iodide and 10.9 g of potassium t-butoxide were suspended in 150 ml of tetrahydrofuran. The resulting suspension was stirred at 0° C. under nitrogen stream for 30 minutes, followed by the dropwise addition thereto of a solution of 10 g of 2-fluoro-5-methoxybenzaldehyde in 20 ml of tetrahydrofuran. The resulting mixture was further stirred for one hour, quenched by the addition of water and extracted with ethyl acetate. The formed organic layer was washed with water and brine successively, dried over anhydrous magnesium sulfate, and evaporated. The resulting residue was subjected to silica gel column chromatography (developer: 5% ethyl acetate/n-hexane) to give 9.1 g of the title compound as a colorless oil.

$^1$H-NMR (CDCl$_3$, 400 MHz) δ;
3.80(s, 3H), 5.37(dd, 1H, J=1.2, 11.2 Hz), 5.81(dd, 1H, J=1.2, 17.6 Hz), 6.75(ddd, 1H, J=3.6, 3.6, 8.8 Hz), 6.84(dd, 1H, J=11.2, 17.6 Hz), 6.93–6.99(m, 2H).

(B) 3-Ethyl-4-fluoroanisole

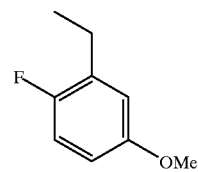

To a solution of 9 g of 3-ethenyl-4-fluoroanisole in 200 ml of ethanol was added 0.9 g of palladium/carbon. The resulting mixture was stirred under hydrogen atmosphere overnight, and filtered through Celite. The filtrate was evaporated, and the resulting residue was subjected to silica gel column chromatography (developer: 50% ethyl acetate/n-hexane) to give 7.0 g of the title compound as a colorless oil.

$^1$H-NMR (CDCl$_3$, 400 MHz) δ; 1.22(t, 3H, J=7.6 Hz), 2.64(q, 2H, J=7.6 Hz), 3.77(s, 3H), 6.65(ddd, 1H, J=3.2, 3.2, 8.8 Hz), 6.72(d, 1H, J=3.6, 6.0 Hz), 6.92(t, 1H, J=8.8 Hz).

(C) 4-Ethyl-5-fluoro-2-methoxybenzaldehyde

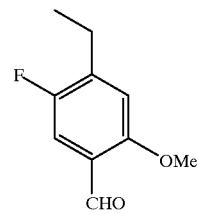

The title compound was obtained as a colorless solid by the use of 3-ethyl-4-fluoroanisole in a similar manner to that of Example 29 (A).

$^1$H-NMR (CDCl$_3$, 400 MHz) δ; 1.26(t, 3H, J=7.6 Hz), 2.70(q, 2H, J=7.6 Hz), 3.92(s, 3H), 6.80(d, 1H, J=5.5 Hz), 7.45(d, 1H, J=9.3 Hz), 10.36(d, 1H, J=3.1 Hz).

(D) 2,5-Diethyl-4-fluoroanisole

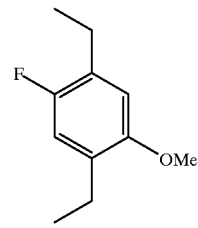

The title compound was obtained as a colorless oil by the use of 4-ethyl-5-fluoro-2-methoxybenzaldehyde in a similar manner to that of the above steps (A) and (B).

$^1$H-NMR (CDCl$_3$, 400 MHz) δ; 1.17(t, 3H, J=7.5 Hz), 1.22(t, 3H, J=7.5 Hz), 2.57(q, 2H, J=7.5 Hz), 2.62(q, 2H, J=7.5 Hz), 3.80(s, 3H), 6.63(d, 1H, J=6.4 Hz), 6.80(d, 1H, J=10.4 Hz).

2,5-Diethyl-4-fluorophenol

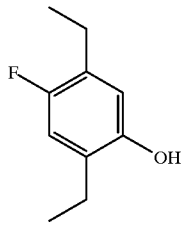

The title compound was obtained as a colorless oil by the use of 2,5-diethyl-4-fluoroanisole in a similar manner to that of Preparative Example 29 (C).

$^1$H-NMR (CDCl$_3$, 400 MHz) δ; 1.19(t, 3H, J=7.6 Hz), 1.21(t, 3H, J=7.6 Hz), 2.54–2.61(m, 4H), 4.48(s, 1H), 6.58 (d, 1H, J=6.6 Hz), 7.78(d, 1H, J=10.4 Hz).

(E) 4,7-Diethyl-5-fluorobenzofuran-2-carbaldehyde

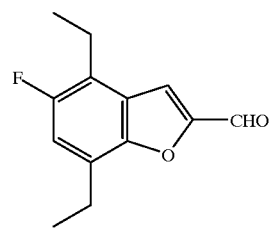

The title compound was prepared from 3-ethyl-4-fluoroanisole in a similar manner to that of Preparative Example 27.

$^1$H-NMR (CDCl$_3$, 400 MHz) δ; 1.28(t, 3H, J=7.6 Hz), 1.34(t, 3H, J=7.6 Hz), 2.87(dq, 2H, J=1.2, 7.6 Hz), 2.94(q, 2H, J=7.6 Hz), 7.06(d, 1H, J=10.8 Hz), 7.60(s, 1H), 9.86(s, 1H).

Preparative Example 31

5-Chloro-3-fluoro-4,7-dimethylbenzofuran

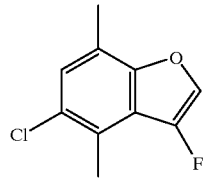

A mixture prepared by adding dropwise 0.9 ml of bromine into 20 ml of a solution of 2 g of 5-chloro-4,7-dimethylbenzofuran in hexane was stirred for 3 hours and poured into a saturated aqueous solution of sodium bicarbonate. The resulting mixture was extracted with ethyl acetate, and the organic layer was washed with a saturated aqueous solution of sodium bicarbonate and brine, dried over anhydrous magnesium sulfate, and filtered. The filtrate was concentrated to give 4 g of 2, 4-dibromo-5-chloro-2,4-dihydro-4,7-dimethylbenzofuran as a crude product.

The dibromide prepared above was dissolved in 30 ml of a benzene/acetonitrile (9:1) mixture, and 3 g of silver fluoride was added to the resulting solution at 0° C. The resulting mixture was stirred at room temperature under nitrogen atmosphere for 20 hours, and filtered through Celite. The filtrate was concentrated, followed by the addition of water to the resulting crude product. The resulting mixture was extracted with ethyl acetate, and the organic layer was washed with water and brine, dried over anhydrous magnesium sulfate, and filtered. The filtrate was concentrated to give 2.5 g of 5-chloro-2,4-difluoro-2,4-dihydro-4,7-dimethylbenzofuran as a crude product.

The difluoride prepared above was dissolved in 12 ml of a 1M solution of potassium t-butoxide in t-butanol, followed by the addition of 4 g of 18-crown-6. The resulting mixture was stirred at room temperature under nitrogen atmosphere for 12 hours, quenched by the addition of water, and extracted with ethyl acetate. The organic layer was washed with water and brine, dried over anhydrous magnesium sulfate, and filtered. The filtrate was concentrated, and the resulting crude product was purified by silica gel column chromatography to give 1.3 g of the title compound as a pale yellow oil.

$^1$H-NMR (CDCl$_3$, 400 MHz) δ; 2.41(s, 3H), 2.57(s, 3H), 7.12(s, 1H), 7.58(d, 1H, J=4.8 Hz).

Preparative Example 32

4,7-Difluorobenzofuran-2-carbaldehyde

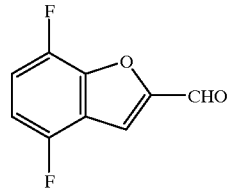

(A) 2,5-Difluorophenol allyl ether

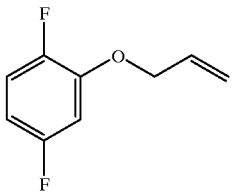

10 g of 2,5-difluorophenol was dissolved in 120 ml of dimethylformamide, and 21 g of potassium carbonate and 8.57 ml of allyl bromide were added to the resulting solution in this order at room temperature. The resulting mixture was stirred at 80° C. for one hour, followed by the addition of water. The resulting mixture was extracted with ethyl acetate, and the organic layer was washed with brine, dried over anhydrous magnesium sulfate, and evaporated. The resulting residue was subjected to silica gel chromatography (developer: 5% ethyl acetate/n-hexane) to give 13 g of the title compound as a colorless oil.

$^1$H-NMR (CDCl$_3$, 400 MHz) δ; 4.58(d, 2H, J=5.2 Hz), 5.33(dd, 1H, J=2.4, 8.4 Hz), 5.44(dd, 1H, d, J=2.4, 17.2 Hz), 5.98–6.10(m, 1H), 6.55–6.60(m, 1H), 6.70(ddd, 1H, J=3.2, 6.8, 10.0 Hz), 7.01(ddd, 1H, J=5.2, 8.8, 10.0 Hz).

(B) 2-Allyl-3,6-difluorophenol

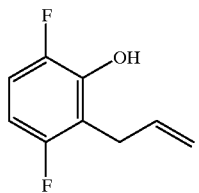

13 g of 2,5-difluorophenol allyl ether was dissolved in 90 ml of N,N-dimethylaniline. The resulting solution was stirred at 170° C. under nitrogen stream for 5 hours and poured into a 10% aqueous solution of hydrogen chloride. The resulting mixture was extracted with ethyl acetate. The organic layer was washed with brine, dried over anhydrous magnesium sulfate, and evaporated. The resutling residue was subjected to silica gel chromatography (developer: 7% ethyl acetate/n-hexane) to give 7.8 g of the title compound as a colorless oil.

$^1$H-NMR (CDCl$_3$, 400 MHz) δ; 3.44(dd, 2H, J=1.2, 6.0 Hz), 5.05–5.09(m, 1H), 5.26–5.28(m, 1H), 5.90–5.99(m, 1H), 6.56(dt, 1H, J=4.4, 9.2 Hz), 6.91(dt, 1H, J=5.2, 9.2 Hz).

(C) 4,7-Difluoro-2,3-dihydro-2-hydroxymethylbenzofuran

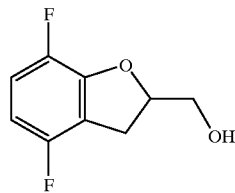

7 g of 2-allyl-3,6-difluorophenol was dissolved in 100 ml of dichloromethane, and 3-chloroperoxybenzoic acid was added to the resulting solution at 0° C. under nitrogen stream. The resulting mixture was stirred at room temperature for 2 hours, followed by the addition of water. The resulting mixture was extracted with dichloromethane, and the organic layer was washed with a saturated aqueous solution of sodium bicarbonate and brine, dried over anhydrous magnesium sulfate, and evaporated to give 7.2 g of an epoxide as a crude product.

Potassium hydroxide was added to a solution of 7.2 g of the above epoxide in a mixture of 30 ml of dimethyl sulfoxide with 10 ml of water at room temperature. The resulting mixture was stirred for 4 hours, followed by the addition of ethyl acetate. The organic layer was washed with brine, dried over anhydrous magnesium sulfate and evaporated. The resulting residue was subjected to silica gel chromatography (developer: 20% ethyl acetate/n-hexane) to give 1.2 g of the title compound as a colorless oil.

$^1$H-NMR (CDCl$_3$, 400 MHz) δ; 3.25(dd, 1H, J=6.7, 16 Hz), 3.33(dd, 1H, J=8.0, 16.0 Hz), 3.75–3.83(m, 1H), 3.90–3.97(m, 1H), 5.04–5.13(m, 1H), 6.49(ddd, 1H, J=2.8, 10.0, 11.2 Hz), 6.87(dt, 1H, J=4.4, 10.0 Hz).

(D) 2-Acetoxymethyl-4,7-difluoro-2,3-dihydrobenzofuran

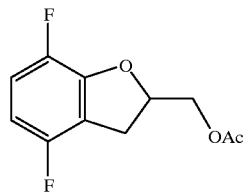

Under nitrogen stream at 0° C., 0.73 ml of acetic anhydride was added to a solution of 1.2 g of 4,7-difluoro-2,3-dihydro-2-hydroxymethylbenzofuran in 6 ml of pyridine. The resulting mixture was stirred at room temperature for 17 hours and poured into a 10% aqueous solution of hydrogen chloride, and the resulting mixture was extracted with ethyl acetate. The organic layer was washed with brine, dried over anhydrous magnesium sulfate and evaporated. The resulting residue was subjected to silica gel chromatography (developer: 5% ethyl acetate/n-hexane) to give 750 mg of the title compound as a colorless oil.

$^1$H-NMR (CDCl$_3$, 400 MHz) δ; 2.17(s, 3H), 3.08(dd, 1H, J=7.2, 15.6 Hz), 3.39(dd, 1H, J=10.0, 15.6 Hz), 4.28(dd, 1H, J=6.4, 12 Hz), 4.36(dd, 1H, J=3.6, 12 Hz), 5.13–5.20(m, 1H), 6.51(ddd, 1H, J=2.8, 10.0, 10.8 Hz), 6.89(dt, 1H, J=4.4, 10.0 Hz).

(E) 2-Acetoxymethyl-4,7-difluorobenzofuran

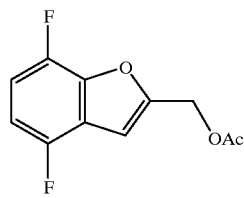

750 mg of 2-acetoxymethyl-4,7-difluoro-2,3-dihydrobenzofuran was dissolved in 15 ml of carbon tetrachloride and 582 mg of N-bromosuccinimide and 10 mg of azodiisopropylnitrile were added successively to the solution at room temperature. The resulting mixture was heated under reflux for one hour and filtered through a glass filter. The filtrate was concentrated to give an oil. Ethyl acetate was added to the oil. The organic layer was washed with brine, dried over anhydrous magnesium sulfate and evaporated.

This bromide was dissolved in 6 ml of tert-butyl alcohol, and 3.3 ml of a 1.0 M solution of potassium tert-butoxide in tert-butyl alcohol was added to the resulting solution at room temperature under nitrogen stream. The resulting mixture was stirred at room temperature for 2 hours, followed by the addition of ethyl acetate. The organic layer was washed with brine, dried over anhydrous magnesium sulfate and evaporated. The resulting residue was subjected to silica gel chromatography (developer: 10% ethyl acetate/n-hexane) to give 252 mg of the title compound as a colorless oil.

$^1$H-NMR (CDCl$_3$, 400 MHz) δ; 2.14(s, 3H), 5.20(s, 2H), 6.84(dt, 1H, J=3.2, 8.8 Hz), 6.89(d, 1H, J=2.4 Hz), 6.98(ddd, 1H, J=4.0, 8.8 Hz).

35

(F) 4,7-Difluoro-2-hydroxymethylbenzofuran

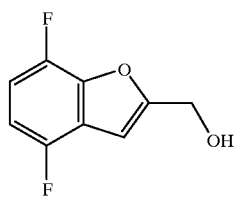

252 mg of 2-acetoxymethyl-4,7-difluorobenzofuran was dissolved in 5 ml of methanol and 455 mg of potassium carbonate was added to the solution at room temperature. The resulting mixture was stirred at the same temperature for 2 hours, followed by the addition of ethyl acetate thereto. The organic layer was washed with brine, dried over anhydrous magnesium sulfate, and evaporated. The resulting residue was subjected to silica gel chromatography (developer: 5% ethyl acetate/n-hexane) to give 161 mg of the title compound as a colorless oil.

$^1$H-NMR (CDCl$_3$, 400 MHz) δ; 4.80(d, 2H, J=4.0 Hz), 6.80(d, 1H, J=2.8 Hz), 6.83(dt, 1H, J=2.8, 8.4 Hz), 6.95(ddd, 1H, J=4.0, 8.4, 10.0 Hz).

(G) 4,7-Difluorobenzofuran-2-carbaldehyde

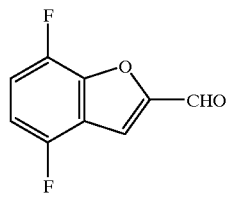

At a temperature of −78° C., 0.26 ml of oxalyl chloride was added to a mixture of 0.42 ml of dimethyl sulfoxide with 7 ml of dichloromethane, and the resulting solution was stirred at the same temperature for 3 minutes. At the same temperature, 272 mg of 4,7-difluoro-2-hydroxybenzofuran was added to the resulting mixture, and the resulting mixture was stirred for 40 minutes. After the addition of 1.2 ml of triethylamine to the reaction mixture, the temperature of the resulting mixture was raised to room temperature. The resulting mixture was further stirred at room temperature for 30 minutes, followed by the addition of water. The resulting mixture was extracted with ethyl acetate, and the organic layer was washed with brine, dried over anhydrous magnesium sulfate, and evaporated. The resulting residue was subjected to silica gel chromatography (developer: 5% ethyl acetate/n-hexane) to give 169 mg of the title compound as a colorless solid.

$^1$H-NMR (CDCl$_3$, 400 MHz) δ; 6.96(dt, 1H, J=2.8, 8.8 Hz), 7.21(ddd, 1H, J=4.0, 8.8, 9.6 Hz), 7.66(d, 1H, J=2.4 Hz), 9.92(s, 1H).

36

Example 1

4-{2-[5-(5,8-Dimethylnaphthalen-2-yl)pyrrolyl]}benzoic acid

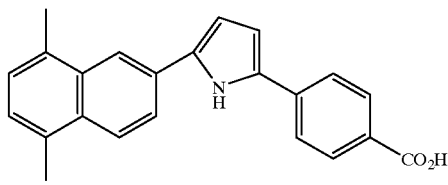

(A) 2-Acryloyl-5,8-dimethylnaphthalene

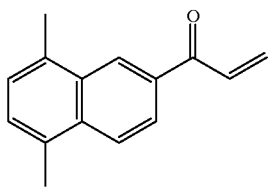

At a temperature of −78° C., of 3.7 g of 5,8-dimethyl-2-naphthaldehyde was dissolved in 80 ml of ether and 30 ml of a 1.0 M solution of vinylmagnesium bromide in tetrahydrofuran was added to the solution. The temperature of the resulting mixture was slowly raised to −30° C. The resulting mixture was quenched with a saturated aqueous solution of ammonium chloride and extracted with ethyl acetate (100 ml×2). The organic layers were combined, washed with brine, dried over anhydrous magnesium sulfate, and filtered. The filtrate was concentrated to give 5.0 g of an allyl alcohol as a crude product.

This crude product was dissolved in 30 ml of dichloromethane, followed by the addition of 30 g of activated manganese dioxide. The resulting mixture was stirred at room temperature for 40 hours, and filtered through Celite. The filtrate was concentrated, and the resulting crude product was purified by silica gel column chromatography to give 1.8 g of the title compound with the recovery of 1.2 g of the starting compound.

$^1$H-NMR (CDCl$_3$, 400 MHz) δ; 2.68(s, 3H), 2.74(s, 3H), 6.00(dd, 1H, J=1.6, 10.4 Hz), 6.50(dd, 1H, J=1.6, 17.2 Hz), 7.27–7.39(m, 3H), 8.06–8.10(m, 2H), 8.64(s, 1H).

(B) Methyl 4-[4-(5,8-dimethylnaphthalen-2-yl)-4-oxobutanoyl]benzoate

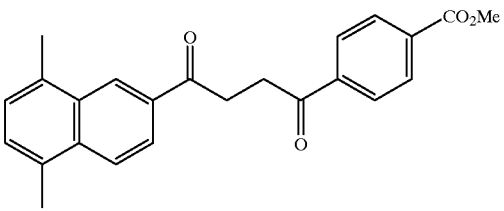

(Process 1)

A mixture comprising 1.8 g of 2-acryloyl-5,8-dimethylnaphthalene, 1.4 g of methyl tere-phthalaldehydate, 0.23 g of sodium acetate, 0.23 g of 3-benzyl-5-(2-hydroxymethyl)-4-methylthiazolium chloride and 100 ml of ethanol was heated under reflux for 10 hours. The resulting crystals were collected by filtration, washed with ethanol, and dried to give 1.26 g of the title compound as colorless crystals.

(Process 2)

A mixture comprising 1.0 g of 5,8-dimethyl-2-naphthaldehyde, 1.2 g of methyl 4-acryloylbenzoate, 0.28 g of 3-benzyl-5-(2-hydroxymethyl)-4-methylthiazolium chloride, 0.88 ml of triethylamine and 20 ml of N,N-dimethylformamide was stirred under heating at 70° C. for 3 hours, and cooled to room temperature by allowing to stand. Water was added to the resulting mixture, followed by the extraction with ethyl acetate (20 ml×3). The organic layers were combined, washed with brine, dried over anhydrous magnesium sulfate, and filtered. The filtrate was concentrated, and the resulting crude crystals were washed with a n-hexane/ethyl acetate mixture to give 0.82 g of the title compound as colorless crystals.

$^1$H-NMR (CDCl$_3$, 400 MHz) δ; 2.68(s, H), 2.75(s, 3H), 3.54(t, 2H, J=6.4 Hz), 3.66(t, 2H, J=6.4 Hz), 3.96(s, 3H), 7.28(d, 1H, J=7.2 Hz), 7.33(d, 1H, J=7.2 Hz), 8.06–8.18(m, 6H), 8.75(d, 1H, J=1.6 Hz).

(C) Methyl 4-{2-[5-(5,8-dimethylnaphthalen-2-yl)pyrrolyl]}benzoate

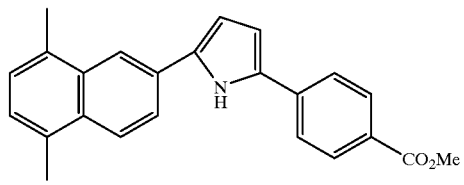

A mixture comprising 0.5 g of methyl 4-[4-(5,8-dimethynaphthalen-2-yl)-4-oxobutanoyl]benzoate, 2.0 g of ammonium acetate and 20 ml of methanol was heated under reflux for 5 hours, and cooled to room temperature by allowing to stand. The resulting yellow crystals were collected by filtration, washed with methanol, and dried to give 0.47 g of a methyl ester as yellow crystals.

$^1$H-NMR (CDCl$_3$, 400 MHz) δ; 2.67(s, 3H), 2.73(s, 3H), 3.93(s, 3H), 6.76(m, 2H), 7.18(d, 1H, J=7.1 Hz), 7.23(d, 1H, J=7.1 Hz), 7.63(d, 2H, J=8.6 Hz), 7.74(dd, 1H, J=1.6 , 9.2 Hz), 8.03–8.09(m, 4H), 8.84(s, 1H)

(D) 4-{2-[5-(5,8-Dimethylnaphthalen-2-yl)pyrrolyl]}benzoic acid

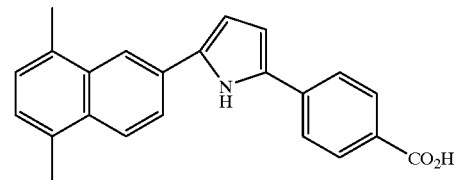

A mixture comprising 0.68 g of the methyl ester, 40 ml of ethanol and 4 ml of a 5N aqueous solution of sodium hydroxide was refluxed for one hour to give a pale yellow suspension. Water was added to the suspension to conduct dissolution. About 3.5 ml of 6N hydrochloric acid and 40 ml of water were added to the resulting solution. The resulting crystalline precipitates were collected by filtration, washed with water, and dried to give 0.52 g of the title compound as yellow crystals.

$^1$H-NMR (CDCl$_3$, 400 MHz) δ; 2.59(s, 3H), 2.69(s, 3H), 6.81(m, 2H), 7.16(d, 1H, J=7.11 Hz), 7.22(d, 1H, J=7.1 Hz), 7.87–8.00(m, 6H), 8.36(s, 1H), 11.6(s, 1H).

Example 2

4-{2-[5-(5,7-Dimethylnaphthalen-2-yl)pyrrolyl]}benzoic acid

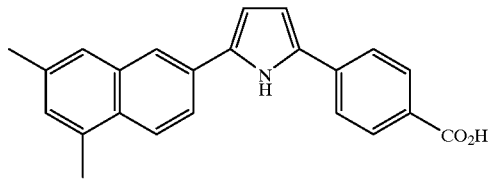

(A) 2-Acryloyl-5,7-dimethylnaphthalene

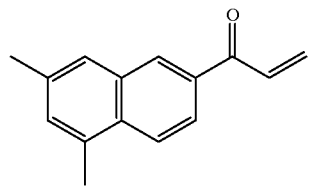

The title compound was prepared in a similar manner to that of Example 1 (A).

$^1$H-NMR (CDCl$_3$, 400 MHz) δ; 2.50(s, 3H), 2.68(s, 3H), 5.97(dd, 1H, J=1.6, 10.8 Hz), 6.49(dd, 1H, J=1.6, 17.2 Hz), 7.29(s, 1H), 7.32(dd, 1H, J=10.8, 17.2 Hz), 7.59(s, 1H), 8.00(m, 2H), 8.37(s, 1H).

(B) Methyl 4-[4-(5,7-dimethylnaphthalen-2-yl)-4-oxobutanoyl]benzoate

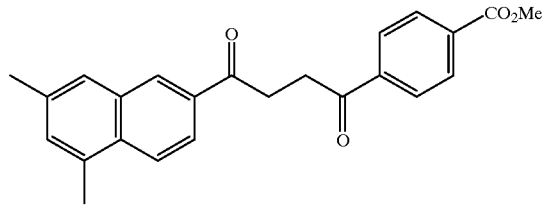

The title compound was prepared in a similar manner to that of Process 1of Example 1 (B).

$^1$H-NMR (CDCl$_3$, 400 MHz) δ; 2.51(s, 3H), 2.6(s, 3H), 3.53(t, 2H, J=6.1 Hz), 3.63(t, 2H, J=6.1 Hz) 3.96(s, 3H) 7.30(s, 1H), 7.61(s, 1H), 8.01(d, 1H, J=8.8 Hz), 8.03(dd, 1H, J=1.6, 8.8 Hz), 8.12(d, 2H, J=8.8 Hz), 8.15(d, 2H, J=8.8 Hz), 8.48(s, 1H).

(C) Methyl 4-{2-[5-(5,7-dimethylnaphthalen-2-yl)pyrrolyl]}benzoate

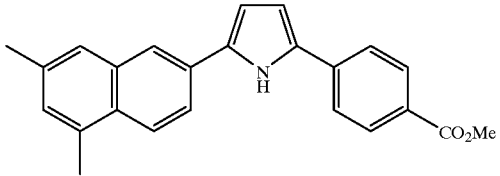

The title compound was prepared in a similar manner to that of Example 1 (C).

$^1$H-NMR (CDCl$_3$, 400 MHz) δ; 2.48(s, 3H), 2.67(s, 3H), 3.93(s, 3H), 6.72–6.78(m, 2H), 7.14(s, 1H), 7.49(s, 1H), 7.62(d, 2H, J=8.4 Hz), 7.67(dd, 1H, J=1.6, 8.8 Hz), 7.85(d, 1H, J=1.6 Hz), 7.97(d, 1H, J=8.8 Hz), 8.07(d, 2H, J=8.4 Hz), 8.82(s, 1H).

(D) 4-{2-[5-(5,7-Dimethylnaphthalen-2-yl)pyrrolyl]}benzoic acid

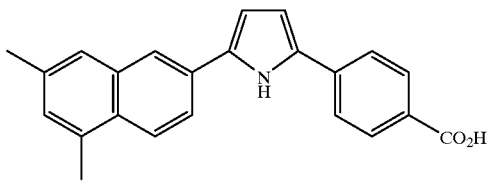

The title compound was prepared in a similar manner to that of Example 1 (D).

$^1$H-NMR (DMSO-$d_6$, 400 MHz) δ; 2.42(s, 3H), 2.60(s, 3H), 6.79(m, 2H), 7.13(s, 1H), 7.48(s, 1H), 7.84–7.94(m, 6H), 8.21(s, 1H), 11.5(s, 1H).

Example 3

4-{2-[5-(5,6,7,8-Tetramethylnaphthalen-2-yl)pyrrolyl]}benzoic acid

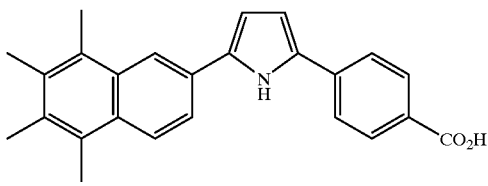

(A) 2-Acryloyl-5,6,7,8-tetramethylnaphthalene

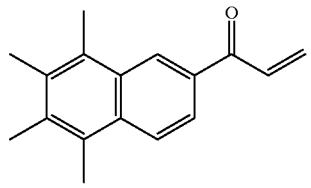

The title compound was prepared in a similar manner to that of Example 1 (A).

$^1$H-NMR (CDCl$_3$, 400 MHz) δ; 2.45(s, 3H), 2.46(s, 3H), 2.65(s, 3H), 2.70(s, 3H), 5.97(dd, 1H, J=2.0, 10.8 Hz), 6.50(dd, 1H, J=1.6, 17.2 Hz), 7.36(dd, 1H, J=10.8, 17.2 Hz), 7.98(dd, 1H, J=1.6, 8.8 Hz), 8.11(d, 1H, J=8.8 Hz), 8.71(d, 1H, J=1.6 Hz).

(B) Methyl 4-[4-(5,6,7,8-tetramethylnaphthalen-2-yl)-4-oxobutanoyl]benzoate

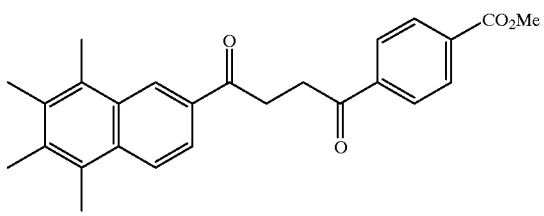

The title compound was prepared in a similar manner to that of Process 1 of Example 1 (B).

$^1$H-NMR (CDCl$_3$, 400 MHz) δ; 2.45(s, 6H), 2.64(s, 3H), 2.71(s, 3H), 3.52(t, 2H, J=6.2 Hz), 3.65(t, 2H, J=6.2 Hz), 3.96(s, 3H), 7.92–8.20(m, 6H), 8.80(s, 1H)

(C) Methyl 4-{2-[5-(5,6,7,8-tetramethylnaphthalen-2-yl)pyrrolyl]}benzoate

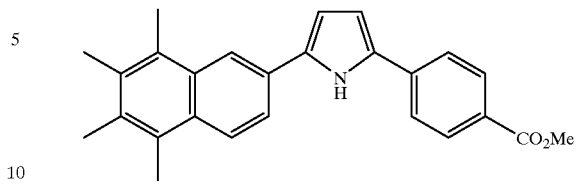

The title compound was prepared in a similar manner to that of Example 1 (C).

$^1$H-NMR (CDCl$_3$, 400 MHz) δ; 2.44(s, 3H), 2.45(s, 3H), 2.64(s, 3H), 2.70(s, 3H), 3.93(s, 3H), 6.73(dd, 1H, J=2.4, 3.2 Hz), 6.77(dd, 1H, J=2.4, 3.2 Hz), 7.61–7.67(m, 3H), 8.04–8.14(m, 4H), 8.82(brs, 1H).

(D) 4-{2-[5-(5,6,7,8-Tetramethylnaphthalen-2-yl)pyrrolyl]}benzoic acid

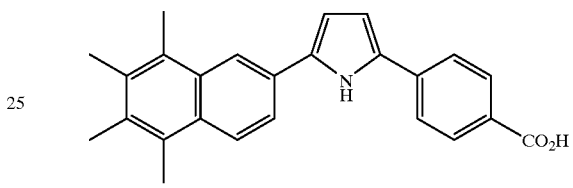

The title compound was prepared in a similar manner to that of Example 1 (D).

$^1$H-NMR (DMSO-$d_6$, 400 MHz) δ; 2.37(s, 3H), 2.38(s, 3H), 2.56(s, 3H), 2.67(s, 3H), 6.79(m, 2H), 7.83(dd, 1H, J=1.2, 8.8 Hz), 7.89(d, 2H, J=8.0 Hz), 7.93(d, 2H, J=8.0 Hz), 8.39(d, 1H, J=1.2 Hz), 11.6(s, 1H)

Example 4

4-{2-[5-(7-Methoxy-8-methylnaphthalen-2-yl)pyrrolyl]}benzoic acid

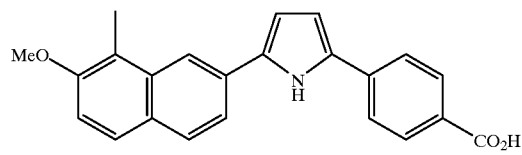

(A) Methyl 4-[4-(7-methoxy-8-methylnaphthalen-2-yl)-4-oxobutanoyl]benzoate

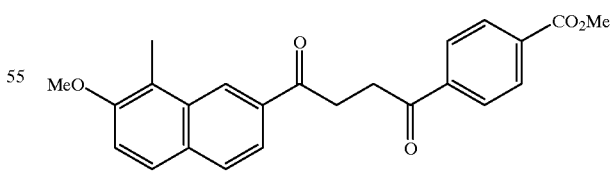

The title compound was prepared in a similar manner to that of Process 2 of Example 1 (B).

$^1$H-NMR (CDCl$_3$, 400 MHz) δ; 2.64(s, 3H), 3.53(t, 2H, J=6.0 Hz), 3.65(t, 2H, J=6.0 Hz), 3.96(s, 3H), 3.98(s, 3H), 7.38(d, 1H, J=9.2 Hz), 7.76(d, 1H, J=9.2 Hz), 7.85(d, 1H, J=8.8 Hz), 7.93(dd, 1H, J=1.6, 8.8 Hz), 8.12(d, 2H, J=8.8 Hz), 8.15(d, 2H, J8.8 Hz), 8.71(m, 1H).

(B) Methyl 4-{2-[5-(7-methoxy-8-methylnaphthalen-2-yl)pyrrolyl]}benzoate

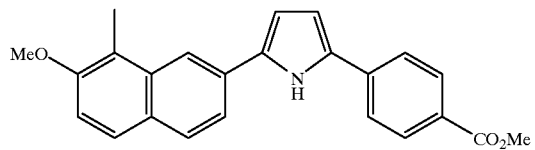

The title compound was prepared in a similar manner to that of Example 1 (C).

¹H-NMR (CDCl₃, 400 MHz) δ; 2.62(s, 3H), 3.94(s, 3H), 3.97(s, 3H), 6.73–6.78(m, 2H), 7.24(d, 1H, J=8.8 Hz), 7.56(dd, 1H, J=2.0, 8.4 Hz), 7.63(d, 2H, J=8.4 Hz), 7.70(d, 1H, J=8.8 Hz), 7.81(d, 1H, J=8.4 Hz), 8.02(s, 1H), 8.07(d, 2H, J=8.4 Hz), 8.83(brs, 1H).

(C) 4-{2-[5-(7-Methoxy-8-methylnaphthalen-2-yl)pyrrolyl]}benzoic acid

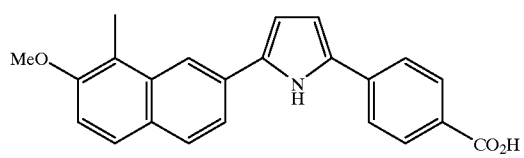

The title compound was prepared in a similar manner to that of Example 1 (D).

¹H-NMR (DMSO-d₆, 400 MHz) δ; 2.56(s, 3H), 3.90(s, 3H), 6.81(d, 2H, J=2.2 Hz), 7.33(d, 1H, J=8.9 Hz), 7.72–7.77(m, 2H), 7.82(d, 1H, J=8.4 Hz), 7.90(d, 2H, J=8.8 Hz), 7.93(d, 2H, J=8.8 Hz), 8.30(s, 1H), 11.6(s, 1H).

Example 5

4-{2-[5-(7-Methoxy-8-ethylnaphthalen-2-yl)pyrrolyl]}benzoic acid

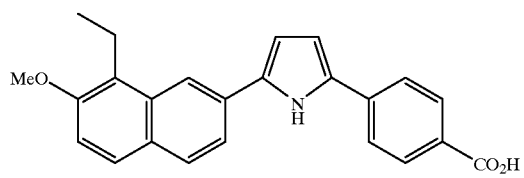

(A) Methyl 4-[4-(7-methoxy-8-ethylnaphthalen-2-yl)-4-oxobutanoyl]benzoate

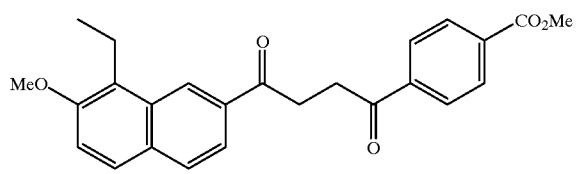

The title compound was prepared in a similar manner to that of Process 2 of Example 1 (B).

¹H-NMR (CDCl₃, 400 MHz) δ; 1.27(t, 3H, J=7.4 Hz), 3.18(q, 2H, J=7.4 Hz), 3.54(t, 2H, J=6.1 Hz), 3.64(t, 2H, J=6.1 Hz), 3.96(s, 3H), 3.98(s, 3H), 7.39(d, 1H, J=9.2 Hz), 7.76(d, 1H, J=9.2 Hz), 7.85(d, 1H, J=8.4 Hz), 7.92(dd, 1H, J=1.6, 8.4 Hz), 8.13(d, 2H, J=8.4 Hz), 8.16(d, 2H, J=8.4 Hz), 8.72(s, 1H).

(B) Methyl 4-{2-[5-(7-methoxy-8-ethylnaphthalen-2-yl)pyrrolyl]}benzoate

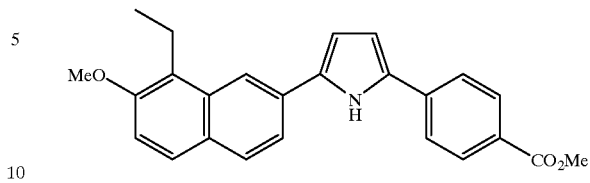

¹H-NMR (CDCl₃, 400 MHz) δ; 1.29(t, 3H, J=7.5 Hz), 3.16(q, 2H, J=7.5 Hz), 3.94(s, 3H), 3.97(s, 3H), 6.73–6.78(m, 2H), 7.24(d, 1H, J=8.8 Hz), 7.54(dd, 1H, J=2.0, 8.4 Hz), 7.63(d, 2H, J=8.0 Hz), 7.70(d, 1H, J=8.8 Hz), 7.82(d, 1H, J=8.4 Hz), 8.04(s, 1H), 8.07(d, 2H, J=8.0 Hz), 8.82(brs, 1H).

(C) 4-{2-[5-(7-Methoxy-8-ethylnaphthalen-2-yl)pyrrolyl]}benzoic acid

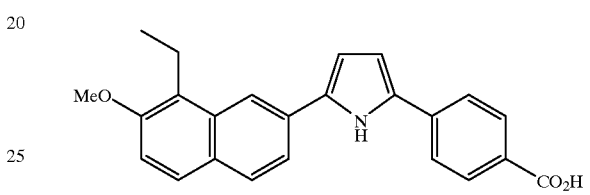

The title compound was prepared in a similar manner to that of Example 1 (D).

¹H-NMR (DMSO-d₆, 400 MHz) δ; 1.18(t, 3H, J=7.6 Hz), 3.14(q, 2H, J=7.6 Hz), 3.91(s, 3H), 6.81(m, 2H), 7.33(d, 1H, J=8.8 Hz), 7.74(d, 2H, J=8.8 Hz), 7.83(d, 1H, J=8.8 Hz), 7.91(d, 2H, J=8.4 Hz), 7.94(d, 2H, J=8.4 Hz) 8.28(s, 1H), 11.6(s, 1H).

Example 6

4-{2-[5-(8-Methylnaphthalen-2-yl)pyrrolyl]}benzoic acid

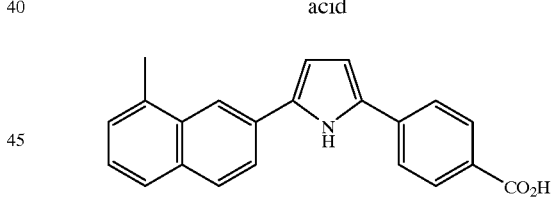

(A) Methyl 4-[4-(8-methylnaphthalen-2-yl)-4-oxobutanoyl]benzoate

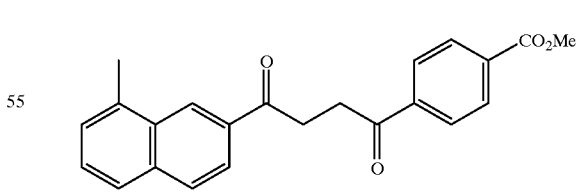

The title compound was prepared in a similar manner to that of Process 2 of Example 1 (B).

¹H-NMR (CDCl₃, 400 MHz) δ; 2.79(s, 3H), 3.54(t, 2H, J=6.4 Hz), 3.66(t, 2H, J=6.4 Hz), 3.96(s, 3H), 7.40(d, 1H, J=8.0 Hz), 7.50(t, 1H, J=8.0 Hz), 7.74(d, 1H, J=8.0 Hz), 7.92(d, 1H, J=8.4 Hz), 8.08(dd, 1H, J=2.0, 8.4 Hz), 8.12(d, 2H, J=8.8 Hz), 8.16(d, 2H, J=8.8 Hz), 8.75(s, 1H).

(B) Methyl 4-{2-[5-(8-methylnaphthalen-2-yl)pyrrolyl]}benzoate

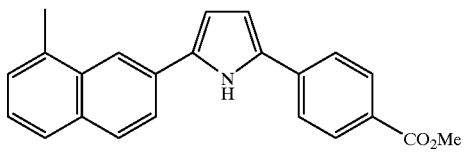

The title compound was prepared in a similar manner to that of Example 1 (D).

$^1$H-NMR (CDCl$_3$, 400 MHz) δ; 2.76(s, 3H), 3.94(s, 3H), 6.74–6.78(m, 2H), 7.34–7.36(m, 2H), 7.64(d, 2H, J=8.4 Hz), 7.68–7.72(m, 2H), 7.88(d, 1H, J=8.4 Hz), 8.06–8.10(m, 3H), 8.84(brs, 1H).

(C) 4-{2-[5-(8-Methylnaphthalen-2-yl)pyrrolyl]}benzoic acid

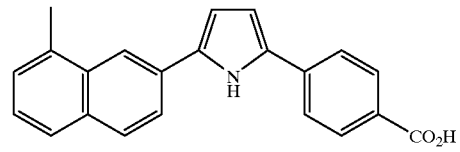

The title compound was prepared in a similar manner to that of Example 1 (D).

$^1$H-NMR (DMSO-d$_6$, 400 MHz) δ; 2.73(s, 3H), 6.83(d, 2H, J=2.0 Hz), 7.30–7.36(m, 2H), 7.70(m, 1H), 7.86–7.96 (m, 6H), 8.37(s, 1H), 11.6(s, 1H).

Example 7

4-{2-[5-(8-Ethylnaphthalen-2-yl)pyrrolyl]}benzoic acid

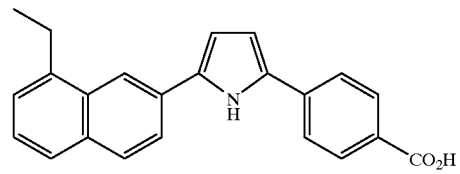

(A) Methyl 4-[4-(8-ethylnaphthalen-2-yl)-4-oxobutanoyl]benzoate

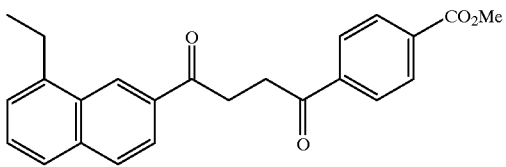

The title compound was prepared in a similar manner to that of Process 2 of Example 1 (B).

$^1$H-NMR (CDCl$_3$, 400 MHz) δ; ; 1.42(t, 3H, J=7.5 Hz), 3.20(q, 2H, J=7.5 Hz), 3.55(t, 2H, J=6.4 Hz), 3.65(t, 2H, J=6.4 Hz), 3.96(s, 3H), 7.42(d, 1H, J=7.6 Hz), 7.53(t, 1H, J=7.6 Hz), 7.74(d, 1H, J=8.0 Hz), 7.92(d, 1H, J=8.8 Hz), 8.07(dd, 1H, J=2.0, 8.8 Hz), 8.13(d, 2H, J=8.4 Hz), 8.16(d, 2H, J=8.4 Hz), 8.81(s, 1H).

(B) Methyl 4-{2-[5-(8-ethylnaphthalen-2-yl)pyrrolyl]}benzoate

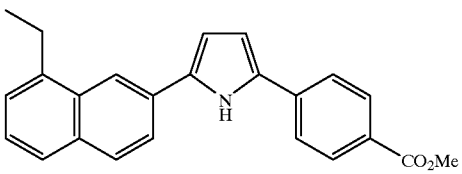

The title compound was prepared in a similar manner to that of Example 1 (C).

$^1$H-NMR (CDCl$_3$, 400 MHz) δ; 1.44(t, 3H, J=7.5 Hz), 3.18(q, 2H, J=7.5 Hz), 3.94(s, 3H), 6.74(dd, 1H, J=2.8, 3.6 Hz), 6.78(dd, 1H, J=2.8, 3.6 Hz), 7.36–7.42(m, 2H), 7.63(d, 2H, J=8.4 Hz), 7.67–7.70(m, 2H), 7.89(d, 1H, J=8.8 Hz), 8.08(d, 2H, J=8.4 Hz), 8.13(s, 1H), 8.82(brs, 1H).

(C) 4-{2-[5-(8-Ethylnaphthalen-2-yl)pyrrolyl]}benzoic acid

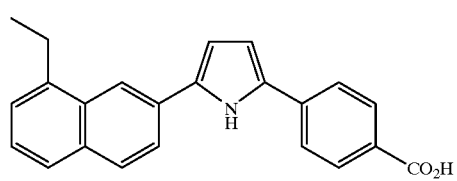

The title compound was prepared in a similar manner to that of Example 1(D).

$^1$H-NMR (DMSO-d$_6$, 400 MHz) δ; 1.35(t, 3H, J=7.5 Hz), 3.18(q, 2H, J=7.5 Hz), 6.82(s, 2H), 7.34–7.37(m, 2H), 7.70(m, 1H), 7.88–7.96(m, 6H), 8.41(s, 1H), 11.6(s, 1H).

Example 8

4-{2-[5-(8-Isopropylnaphthalen-2-yl)pyrrolyl]}benzoic acid

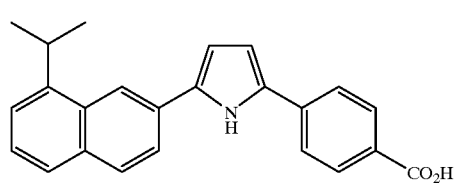

(A) Methyl 4-[4-(8-isopropylnaphthalen-2-yl)-4-oxobutanoyl]benzoate

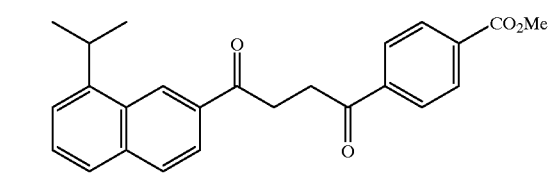

The title compound was prepared in a similar manner to that of Process 2 of Example 1 (B).

$^1$H-NMR (CDCl$_3$, 400 MHz) δ; 1.44(d, 6H, J=7.0 Hz), 3.54(t, 2H, J=6.4 Hz), 3.66(t, 2H, J=6.4 Hz), 3.87(q, 1H, J=7.0 Hz), 3.96(s, 3H), 7.50(d, 1H, J=8.0 Hz), 7.58(t, 1H, J=8.0 Hz), 7.73(d, 1H, J=8.0 Hz), 7.92(d, 1H, J=8.4 Hz), 8.06(dd, 1H, J=1.6, 8.8 Hz), 8.12(d, 2H, J=8.0 Hz), 8.16(d, 2H, J=8.0 Hz), 8.90(s, 1H).

(B) Methyl 4-{2-[5-(8-isopropylnaphthalen-2-yl)pyrrolyl]}benzoate

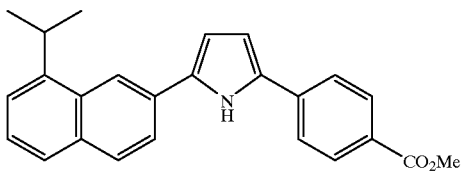

The title compound was prepared in a similar manner to that of Example 1 (C).

$^1$H-NMR (CDCl$_3$, 400 MHz) δ; 1.45(d, 6H, J=7.2 Hz), 3.83(quint., 1H, J=7.2 Hz), 3.94(s, 3H), 6.74(dd, 1H, J=2.4, 4.0 Hz), 6.78(dd, 1H, J=2.4, 4.0 Hz), 7.41–7.46(m, 2H), 7.63(d, 2H, J=8.8 Hz), 7.67–7.70(m, 2H) 7.89(d, 1H, J=8.4 Hz), 8.07(d, 2H, J=8.8 Hz), 8.21(s, 1H), 8.82(brs, 1H)

(C) 4-{2-[5-(8-Isopropylnaphthalen-2-yl)pyrrolyl]}benzoic acid

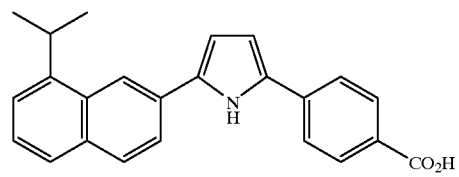

The title compound was prepared in a similar manner to that of Example 1 (D).

$^1$H-NMR (DMSO-d$_6$, 400 MHz) δ; 1.37(d, 6H, J=6.8 Hz), 3.96(quint., 1H, J=6.8 Hz), 6.81(m, 2H), 7.37–7.44(m, 2H), 7.69(d, 1H, J=8.0 Hz), 7.88–7.96(m, 6H), 8.48(s, 1H), 11.6(s, 1H).

Example 9

4-{2-[5-(8-Isopropenylnaphthalen-2-yl)pyrrolyl]}benzoic acid

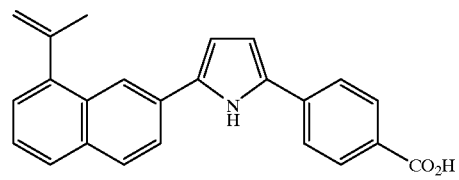

(A) methyl 4-[4-(8-isopropenylnaphthalen-2-yl)-4-oxobutanoyl]benzoate

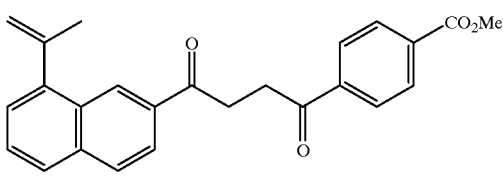

The title compound was prepared in a similar manner to that of Process 2 of Example 1 (B).

$^1$H-NMR (CDCl$_3$, 400 MHz) δ; 2.25(s, 3H), 3.52(t, 2H, J=6.4 Hz), 3.63(t, 2H, J=6.4 Hz), 3.96(s, 3H), 5.10(m, 1H), 5.51(m, 1H), 7.40(dd, 1H, J=1.2, 6.8 Hz), 7.56(t, 1H), J=8.0 Hz), 7.79(d, 1H, J=8.4 Hz), 7.91(d, 1H, J=8.4 Hz), 8.06(dd, 1H, J=2.0, 8.8 Hz), 8.11(d, 2H, J=8.4 Hz), 8.16(d, 2H, J=8.4 Hz), 8.82(s, 1H).

(B) Methyl 4-{2-[5-(8-isopropenylnaphthalen-2-yl)pyrrolyl]}benzoate

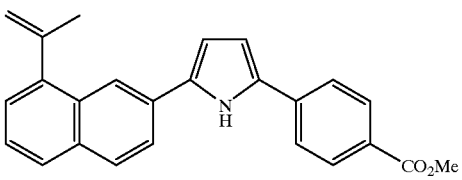

The title compound was prepared in a similar manner to that of Example 1 (C).

$^1$H-NMR (CDCl$_3$, 400 MHz) δ; 2.28(s, 3H), 3.94(s, 3H), 5.13(m, 1H), 5.49(m, 1H), 6.72(dd, 1H, J=2.8, 3.6 Hz), 6.76(dd, 1H, J=2.4, 3.6 Hz), 7.34(dd, 1H, J=1.6, 7.2 Hz), 7.41(dd, 1H, J=7.2, 8.0 Hz), 7.62(d, 2H, J=8.8 Hz), 7.70(dd, 1H, J=2.0, 8.8 Hz), 7.74(d, 1H, J=8.0 Hz), 7.88(d, 1H, J=8.4 Hz), 8.07(d, 2H, J=8.8 Hz), 8.14(s, 1H), 8.79(brs, 1H).

(C) 4-{2-[5-(8-Isopropenylnaphthalen-2-yl)-pyrrolyl]}benzoic acid

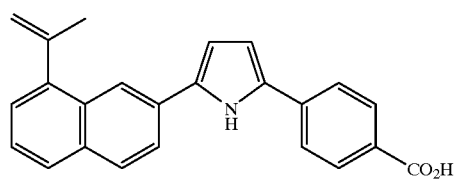

The title compound was prepared in a similar manner to that of Example 1 (D).

$^1$H-NMR (DMSO-d$_6$, 400 MHz) δ; 2.23(s, 3H), 5.07(m, 1H), 5.46(m, 1H), 6.70(m, 1H), 6.81(m, 1H), 7.31(d, 1H, J=7.2 Hz), 7.40(t, 1H, J=8.0 Hz), 7.88–7.95(m, 6H), 8.23(s, 1H), 11.6(s, 1H).

Example 10

4-{2-[5-(8-Phenylnaphthalen-2-yl)pyrrolyl]}benzoic acid

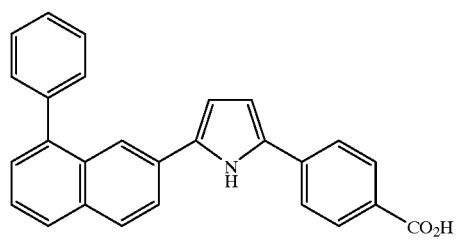

(A) Methyl 4-[4-(8-phenylnaphthalen-2-yl)-4-oxobutanoyl]}benzoate

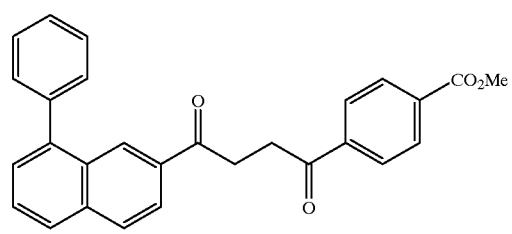

The title compound was prepared in a similar manner to that of Process 2 of Example 1 (B).

¹H-NMR (CDCl₃, 400 MHz) δ;

3.45(m, 4H), 3.95(s, 3H), 7.46–7.54(m, 6H), 7.66(t, 1H, J=8.0 Hz), 7.90(d, 1H, J=8.4 Hz), 7.98(d, 1H, J=8.8 Hz), 8.06–8.10(m, 3H), 8.13(d, 2H, J=8.4 Hz), 8.66(s, 1H).

(B) Methyl 4-{2-[5-(8-phenylnaphthalen-2-pyrrolyl]}benzoate

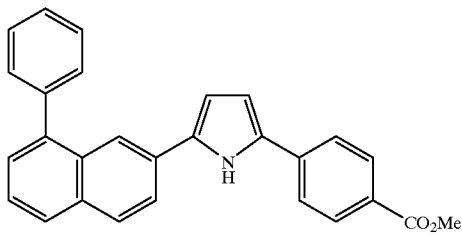

The title compound was prepared in a similar manner to that of Example 1 (C).

¹H-NMR (CDCl₃, 400 MHz) δ; 3.92(s, 3H), 6.64(dd, 1H, J=2.4, 3.6 Hz) 6.71(dd, 1H, J=2.4, 3.6 Hz), 7.44(dd, 1H, J=1.6, 7.2 Hz), 7.48–7.56(m, 8H), 7.72(dd, 1H, J=1.6, 8.4 Hz), 7.84(d, 1H, J=8.4 Hz), 7.94(d, 1H, J=8.4 Hz), 8.00(s, 1H), 8.03(d, 2H, J=8.4 Hz), 8.71(brs, 1H).

(C) 4-{2-[5-(8-Phenylnaphthalen-2-yl)pyrrolyl))benzoic acid

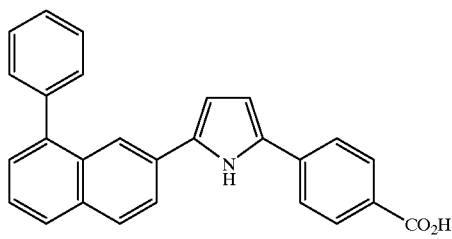

The title compound was prepared in a similar manner to that of Example 1 (D).

¹H-NMR (DMSO-d₆, 400 MHz) δ; 6.48(m, 1H), 6.72(m, 1H), 7.41(dd, 1H, J=1.2, 6.8 Hz), 7.46–7.58(m, 6H), 7.78(d, 2H, J=8.4 Hz), 7.88(d, 2H, J=8.4 Hz), 7.91(d, 1H, J=8.4 Hz), 8.00(dd, 1H, J=1.2, 7.8 Hz), 8.02(d, 1H, J=7.8 Hz), 8.09(s, 1H), 11.6(s, 1H).

Example 11

4-{2-[5-(5,8-Dimethylnaphthalen-2-yl)-1-methylpyrrolyl]}benzoic acid

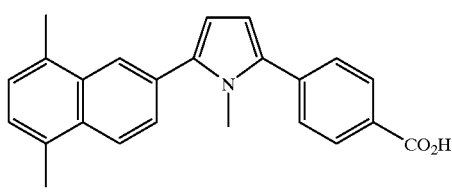

(A) Methyl 4-{2-[5-(5,8-dimethylnaphthalen-2-yl)-1-methylpyrrolyl]}benzoate

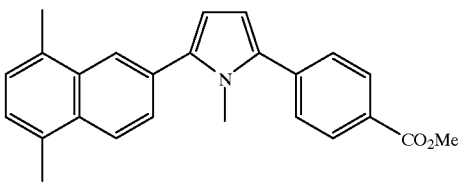

Under nitrogen atmosphere, 240 mg of methyl 4-{2-(5-(5,8-dimethylnaphthalen-2-yl)pyrrolyl]}benzoate was dissolved in 5 ml of N,N-dimethylformamide, followed by the addition thereto of 33 mg of sodium hydride (60%). The resulting mixture was stirred for one hour, and 0.06 ml of methyl iodide was added dropwise into the resulting mixture at 0° C. The resulting mixture was stirred at room temperature for one hour, followed by the addition of a saturated aqueous solution of ammonium chloride. The resulting mixture was extracted with ethyl acetate (30 ml×2). The organic layers were combined, washed with brine, dried over anhydrous magnesium sulfate, and filtered. The filtrate was concentrated to give 300 mg of the title compound as a crude product.

¹H-NMR (CDCl₃, 400 MHz) δ; 2.70(s, 6H), 3.72(s, 3H), 3.94(s, 3H), 6.47(d, 1H, J=3.6 Hz), 6.49(d, 1H, J=3.6 Hz), 7.21–7.26(m, 2H), 7.59(d, 2H, J=8.0 Hz), 7.66(dd, 1H, J=1.6, 8.4 Hz), 8.06–8.12(m, 4H).

(B) 4-{2-[5-(5,8-Dimethylnaphthalen-2-yl)-1-methylpyrrolyl]}benzoic acid

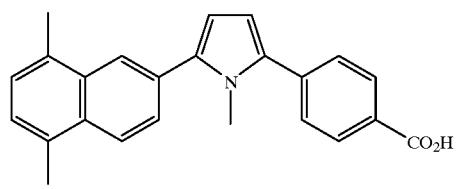

The title compound was prepared in a similar manner to that of Example 1 (D).

¹H-NMR (DMSO-d₆, 400 MHz) δ; 2.62(s, 3H), 2.66(s, 3H), 3.71(s, 3H), 6.48(m, 2H), 7.24(d, 1H, J=6.8 Hz), 7.26(d, 1H, J=6.8 Hz), 7.68(d, 2H, J=8.0 Hz), 7.73(d, 1H, J=7.6 Hz), 7.99(d, 2H, J=8.0 Hz), 8.07(m, 2H).

Example 12

4-{2-[5-(5,8-Dimethylnaphthalen-2-yl)-1-isopropylpyrrolyl]}benzoic acid

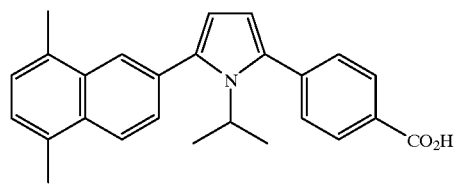

(A) Methyl 4-{2-[5-(5,8-dimethylnaphthalen-2-yl)-1-isopropylpyrrolyl]}benzoate

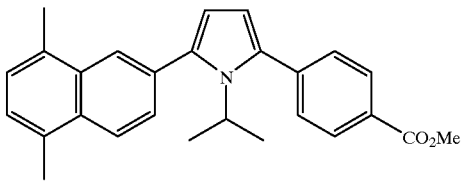

0.23 g of methyl 4-[4-(5,8-dimethylnaphthalen-2-yl)-4-oxobutanoyl]benzoate was dissolved in 4 ml of acetic acid and 4 ml of isopropylamine was added to the solution at room temperature. The resulting mixture was heated under reflux for 2 hours, and cooled to room temperature by allowing to stand. Water was added to the resulting mixture, and the resulting mixture was extracted with ethyl acetate (30 ml×2). The organic layers were combined, washed with a saturated aqueous solution of sodium bicarbonate and brine successively, dried over anhydrous magnesium sulfate, and filtered. The filtrate was concentrated and the resulting crude product was purified by silica gel column chromatography to give 95 mg of the title compound.

$^1$H-NMR (CDCl$_3$, 400 MHz) δ; 1.30(d, 6H, J=7.0 Hz), 2.69(s, 3H), 2.71(s, 3H), 3.96(s, 3H), 4.58(quint., 1H, J=7.0 Hz), 6.29(s, 2H), 7.23–7.28(m, 2H), 7.58(d, 2H, J=8.2 Hz), 7.65(dd, 1H, J=1.6, 8.4 Hz), 8.05(d, 1H, J=8.4 Hz), 8.08–8.11(m, 3H).

(B) 4-{2-[5-(5,8-Dimethylnaphthalen-2-yl)-1-isopropylpyrrolyl]}benzoic acid

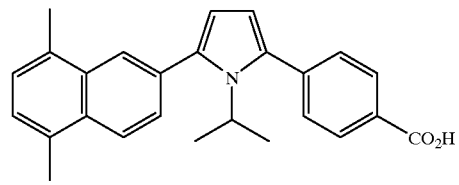

The title compound was prepared in a similar manner to that of Example 1 (D).

$^1$H-NMR (DMSO-d$_6$, 400 MHz) δ; 1.22(d, 6H, J=7.0 Hz), 2.63(s, 6H), 4.50(quint., 1H, J=7.0 Hz), 6.23(s, 2H), 7.27(q, AB type, 2H, J=6.8 Hz), 7.58(d, 2H, J=8.0 Hz), 7.64(dd, 1H, J=1.6, 8.8 Hz), 7.99(m, 3H), 8.06(d, 1H, J=8.8 Hz), 12.9(brs, 1H).

Example 13

4-{2-[5-(4,7-Dimethylbenzofuran-2-yl)pyrrolyl]}benzoic acid

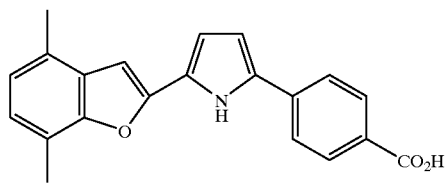

(A) Methyl 4-[4-(4,7-dimethylbenzofuran-2-yl)-4-oxobutanoyl]benzoate

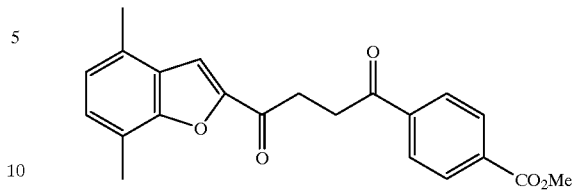

The title compound was prepared in a similar manner to that of Process 2 of Example 1 (B).

$^1$H-NMR (CDCl$_3$, 400 MHz) δ; 2.50(s, 3H), 2.51(s, 3H), 3.45–3.55(m, 4H), 3.94(s, 3H), 7.00(d, 1H, J=6.8 Hz), 7.16(d, 1H, J=6.8 Hz), 7.62(s, 1H), 8.09(d, 2H, J=8.4 Hz), 8.14(d, 2H, J=8.4 Hz).

(B) Methyl 4-{2-[5-(4,7-dimethylbenzofuran-2-yl)pyrrolyl]}benzoate

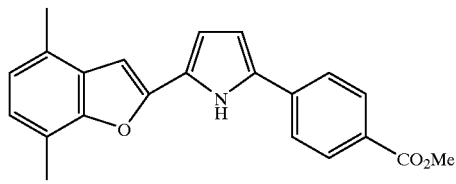

The title compound was prepared in a similar manner to that of Example 1 (C).

$^1$H-NMR (CDCl$_3$, 400 MHz) δ; 2.48(s, 3H), 2.55(s, 3H), 3.93(s, 3H), 6.72–6.77(m, 2H), 6.83(s, 1H), 6.93(d, 1H, J=6.8 Hz), 6.97(d, 1H, J=6.8 Hz), 7.63(d, 2H, J=8.4 Hz), 8.07(d, 2H, J=8.4 Hz), 9.00(brs, 1H).

(C) 4-{2-[5-(4,7-Dimethylbenzofuran-2-yl)pyrrolyl]}benzoic acid

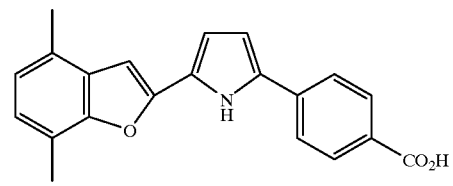

The title compound was prepared in a similar manner to that of Example 1 (D).

$^1$H-NMR (DMSO-d$_6$, 400 MHz) δ; 2.43(s, 3H), 2.46(s, 3H), 6.71(t, 1H, J=2.4 Hz), 6.84(t, 1H, J=2.4 Hz), 6.92(d, 1H, J=7.2 Hz), 6.96(d, 1H, J=7.2 Hz), 7.23(s, 1H), 7.89(d, 2H, J=8.4 Hz), 7.95(d, 2H, J=8.4 Hz), 11.81(brs, 1H), 12.85(brs, 1H).

Example 14

4-{2-[5-(4,7-Dichlorobenzofuran-2-yl)pyrrolyl]}benzoic acid

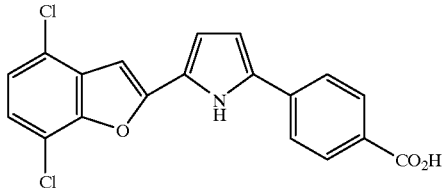

The title compound was prepared in a similar manner to that of Example 1 (D).

$^1$H-NMR (DMSO-$d_6$, 400 MHz) δ; 6.83(t, 1H, J=2.4 Hz), 6.89(t, 1H, J=2.4 Hz), 7.35(d, 1H, J=7.2 Hz), 7.38(d, 1H, J=7.2 Hz), 7.39(s, 1H), 7.91(d, 2H, J=8.4 Hz), 7.97(d, 2H, J=8.4 Hz), 12.02(brs, 1H), 12.86(brs, 1H).

Example 15

4-{2-[5-(7-Chlorobenzofuran-2-yl)pyrrolyl]}benzoic acid

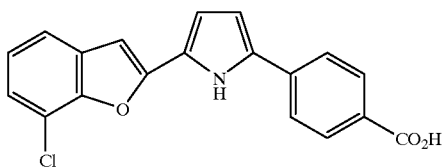

The title compound was prepared in a similar manner to that of Example 1 (D).

$^1$H-NMR (DMSO-$d_6$, 400 MHz) δ; 6.76(t, 1H, J=3.2 Hz), 6.86(t, 1H, J=3.2 Hz), 7.23(t, 1H, J=7.6 Hz), 7.29(s, 1H), 7.33(dd, 1H, J=0.8, 7.6 Hz), 7.61(dd, 1H, J=0.8, 7.6 Hz), 7.90(d, 2H, J=8.4 Hz), 7.95(d, 2H, J=8.4 Hz), 11.96(s, 1H), 12.83(brs, 1H).

Example 16

4-{2-[5-(7-n-Propylbenzofuran-2-yl)pyrrolyl]}benzoic acid

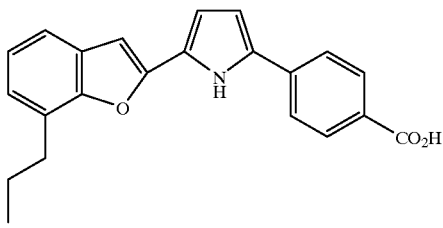

The title compound was prepared in a similar manner to that of Example 1 (D).

$^1$H-NMR (DMSO-$d_6$, 400 MHz) δ; 0.95(t, 3H, J=7.2 Hz), 1.75(sext, 2H, J=7.2 Hz), 2.87(t, 2H, J=7.2 Hz), 6.71(t, 1H, J=3.2 Hz), 6.84(t, 1H, J=3.2 Hz), 7.06(dd, 1H, J=1.2, 7.6 Hz), 7.13(t, 1H, J=7.6 Hz), 7.17(s, 1H), 7.44(dd, 1H, J=1.2, 7.6 Hz), 7.88(d, 2H, J=8.4 Hz), 7.95(d, 2H, J=8.4 Hz), 11.82(s, 1H), 12.80(brs, 1H).

Example 17

4-{2-[5-(4-Methyl-7-ethylbenzofuran-2-yl)pyrrolyl]}benzoic acid

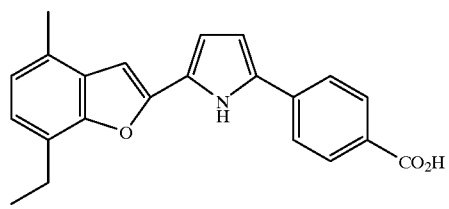

The title compound was prepared in a similar manner to that of Example 1 (D).

$^1$H-NMR (DMSO-$d_6$, 400 MHz) δ; 1.29(t, 3H, J=7.6 Hz), 2.45(s, 3H), 2.88(q, 2H, J=7.6 Hz), 6.70(m, 1H), 6.83(m, 1H), 6.95(d, 1H, J=7.2 Hz), 6.98(d, 1H, J=7.2 Hz), 7.23(s, 1H), 7.89(d, 2H, J=8.8 Hz), 7.94(d, 2H, J=8.8 Hz), 11.80(s, 1H), 12.82(brs, 1H).

Example 18

4-{2-[5-(4-Methyl-7-n-propylbenzofuran-2-yl)pyrrolyl]}benzoic acid

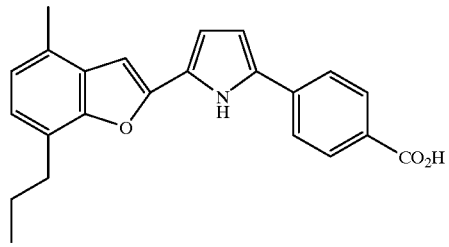

The title compound was prepared in a similar manner to that of Example 1 (D).

$^1$H-NMR (DMSO-$d_6$, 400 MHz) δ; 0.93(t, 3H, J=7.6 Hz), 1.73(sext, 2H, J=7.6 Hz) 2.45(s, 3H), 2.83(t, 2H, J=7.6 Hz), 6.70(m, 1H), 6.83(m, 1H), 6.94(d, 1H, J=7.2 Hz), 6.95(d, 1H, J=7.2 Hz), 7.22(s, 1H), 7.89(d, 2H, J=8.4 Hz), 7.94(d, 2H, J=8.4 Hz), 11.81(s, 1H), 12.83(brs, 1H).

Example 19

4-{2-[5-(4-Chloro-7-methylbenzofuran-2-yl)pyrrolyl]}benzoic acid

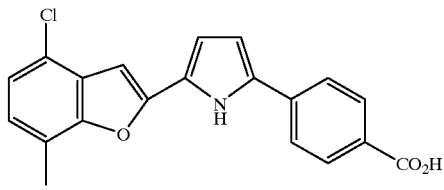

The title compound was prepared in a similar manner to that of Example 1 (D).

$^1$H-NMR (DMSO-$d_6$, 400 MHz) δ; 2.48(s, 3H), 6.78–6.82(m, 1H), 6.85–6.88(m, 1H), 7.09(d, 1H, J=7.6 Hz), 7.21(d, 1H, J=7.6 Hz), 7.29(s, 1H), 7.90(d, 2H, J=8.4 Hz), 7.96(d, 2H, J=8.4 Hz), 11.91(brs, 1H).

Example 20

4-{2-[5-(4-Chloro-7-ethylbenzofuran-2-yl)pyrrolyl]}benzoic acid

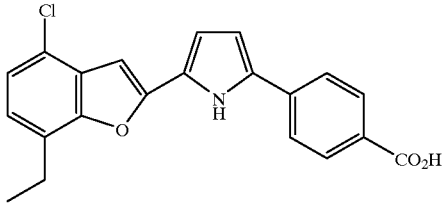

The title compound was prepared in a similar manner to that of Example 1 (D).

$^1$H-NMR (DMSO-$d_6$, 400 MHz) δ; 1.30(t, 3H, J=7.5 Hz), 2.90(q, 2H, J=7.5 Hz), 6.79(dd, 1H, J=2.4, 3.6 Hz), 6.86(dd, 1H, J=2.4, 3.6 Hz), 7.11(d, 1H, J=8.0 Hz), 7.23(d, 1H, J=8.0 Hz), 7.29(s, 1H), 7.89(d, 2H, J=8.8 Hz), 7.95(d, 2H, J=8.4 Hz), 11.90(brs, 1H).

Example 21

4-{2-[5-(4-Chloro-7-n-propylbenzofuran-2-yl)pyrrolyl]}benzoic acid

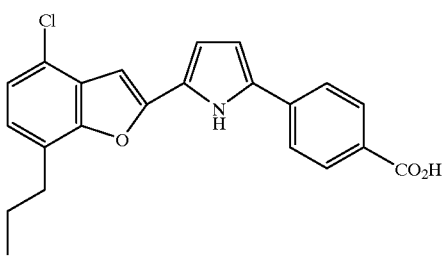

The title compound was prepared in a similar manner to that of Example 1 (D).

$^1$H-NMR (DMSO-$d_6$, 400 MHz) δ; 0.94(t, 3H, J=7.2 Hz), 1.68–1.77(m, 2H), 2.86(t, 2H, J=7.2 Hz), 6.77–6.80(m, 1H), 6.84–6.88(m, 1H), 7.09(d, 1H, J=8.4 Hz), 7.22(d, 1H, J=8.4 Hz), 7.28(s, 1H), 7.89(d, 2H, J=8.8 Hz), 7.95(d, 2H, J=8.8 Hz), 11.90(brs, 1H).

Example 22

4-{2-[5-(5-Chloro-7-methylbenzofuran-2-yl)pyrrolyl]}benzoic acid

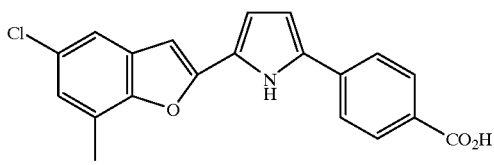

The title compound was prepared in a similar manner to that of Example 1 (D).

$^1$H-NMR (DMSO-$d_6$, 400 MHz) 2.48(s, 3H), 6.74–6.77(m, 1H), 6.83–6.86(m, 1H), 7.10–7.13(m, 1H), 7.17(s, 1H), 7.52–7.54(m, 1H), 7.88(d, 2H, J=8.4 Hz), 7.95(d, 2H, J=8.8 Hz), 11.89(brs, 1H).

Example 23

4-{2-[5-(5-Chloro-7-ethylbenzofuran-2-yl)pyrrolyl]}benzoic acid

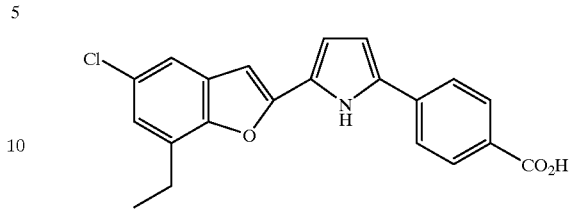

The title compound was prepared in a similar manner to that of Example 1 (D).

$^1$H-NMR (DMSO-$d_6$, 400 MHz) δ; 1.30(t, 3H, J=7.6 Hz), 2.90(q, 2H, J=7.6 Hz), 6.74(dd, 1H, J=1.6, 3.6 Hz), 6.84(dd, 1H, J=1.2, 3.6 Hz), 7.12(s, 1H), 7.17(s, 1H), 7.54(s, 1H), 7.89(d, 2H, J=8.4 Hz), 7.94(d, 2H, J=8.4 Hz), 11.89(s, 1H).

Example 24

4-{2-[5-(5-Chloro-7-n-propylbenzofuran-2-yl)pyrrolyl]}benzoic acid

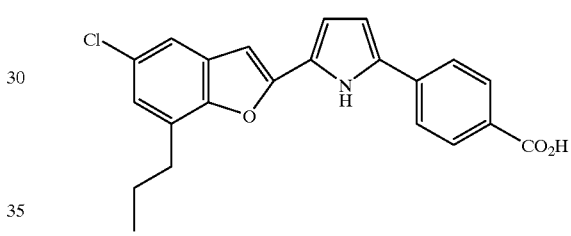

The title compound was prepared in a similar manner to that of Example 1 (D).

$^1$H-NMR (DMSO-$d_6$, 400 MHz) δ; 0.94(t, 3H, J=7.6 Hz), 1.74(sext, 2H, J=7.6 Hz), 2.86(t, 2H, J=7.6 Hz), 6.74(m, 1H), 6.84(m, 1H), 7.10(d, 1H, J=2.4 Hz), 7.18(s, 1H), 7.54(d, 1H, J=2.4 Hz), 7.89(d, 2H, J=8.4 Hz), 7.94(d, 2H, J=8.4 Hz), 11.91(s, 1H).

Example 25

4-{2-[5-(5-Fluoro-7-ethylbenzofuran-2-yl)pyrrolyl]}benzoic acid

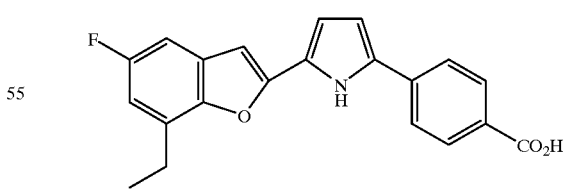

The title compound was prepared in a similar manner to that of Example 1 (D).

$^1$H-NMR (DMSO-$d_6$, 400 MHz) δ; 1.31(t, 3H, J=7.6 Hz), 2.91(q, 2H, J=7.6 Hz), 6.74(t, 1H, J=3.6 Hz), 6.84(t, 1H, J=3.2 Hz), 6.94(dd, 1H, J=2.0, 10.0 Hz), 7.25(dd, 1H, J=2.4, 8.8 Hz), 7.29(s, 1H), 7.94(brs, 4H), 12.04(brs, 1H).

Example 26

4-{2-[5-(5-Fluoro-7-n-propylbenzofuran-2-yl)pyrrolyl]}benzoic acid

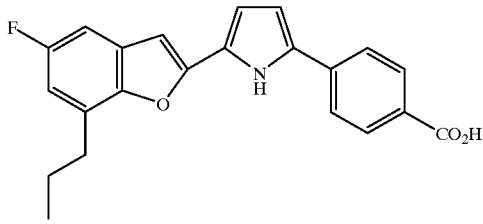

The title compound was prepared in a similar manner to that of Example 1 (D).

$^1$H-NMR (DMSO-$d_6$, 400 MHz) δ; 0.95(t, 3H, J=7.2 Hz), 1.74(q, 2H, J=7.2 Hz), 2.86(t, 2H, J=7.2 Hz), 6.73(dd, 1H, J=2.0, 3.6 Hz), 6.84(dd, 1H, J=2.4, 3.6 Hz), 6.93(dd, 1H, J=2.0, 10.4 Hz), 7.22–7.28(m, 2H), 7.90–7.96(brs, 4H), 12.00(s, 1H).

Example 27

4-{2-[5-(4,7-Difluorobenzofuran-2-yl)pyrrolyl]}benzoic acid

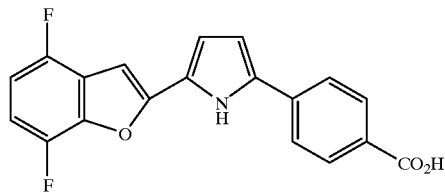

The title compound was prepared in a similar manner to that of Example 1 (D).

$^1$H-NMR (DMSO-$d_6$, 400 MHz) δ; 6.82(dd, 1H, J=2.4, 3.6 Hz), 6.86(dd, 1H, J=2.4, 3.6 Hz), 7.08(dd, 1H, J=3.2, 8.8 Hz), 7.19(dd, 1H, J=3.2, 8.8 Hz), 7.42(d, 1H, J=2.4 Hz), 7.92(d, 2H, J=8.4 Hz), 7.96(d, 2H, J=8.4 Hz), 12.08(s, 1H).

Example 28

4-{2-[5-(5-Chloro-7-isopropenylbenzofuran-2-yl)pyrrolyl]}benzoic acid

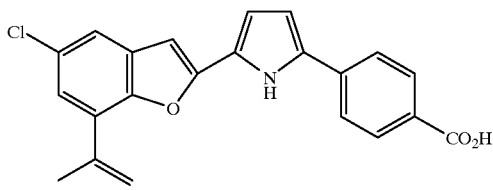

The title compound was prepared in a similar manner to that of Example 1 (D).

$^1$H-NMR (DMSO-$d_6$, 400 MHz) δ; 2.25(s, 3H), 5.48(s, 1H), 5.93(s, 1H), 6.74(m, 1H), 6.84(m, 1H), 7.23(m, 2H), 7.67(m, 1H), 7.88(d, 2H, J=8.4 Hz), 7.94(d, 2H, J=8.4 Hz), 11.96(s, 1H), 12.87(brs, 1H).

Example 29

4-{2-[5-(5-Chloro-7-isopropylbenzofuran-2-yl)pyrrolyl]}benzoic acid

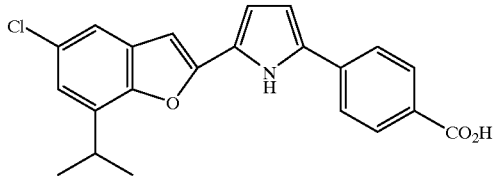

The title compound was prepared in a similar manner to that of Example 1 (D).

$^1$H-NMR (DMSO-$d_6$, 400 MHz) δ; 1.34(d, 6H, J=7.2 Hz), 3.44(quint, 1H, J=7.2 Hz), 6.75(m, 1H), 6.84(m, 1H), 7.12(m, 1H), 7.18(d, 1H, J=0.8 Hz), 7.54(dd, 1H, J=1.2, 2.0 Hz), 7.89(d, 2H, J=8.0 Hz), 7.94(d, 2H.J=8.0 Hz), 11.91(s, 1H), 12.88(brs, 1H).

Example 30

4-{2-[5-(5-Methyl-7-n-propylbenzofuran-2-yl)pyrrolyl]}benzoic acid

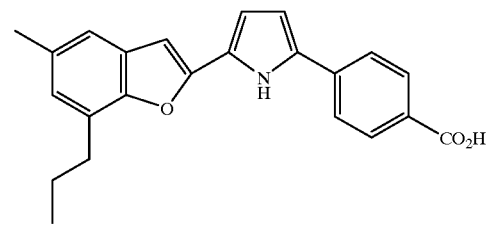

The title compound was prepared in a similar manner to that of Example 1 (D).

$^1$H-NMR (DMSO-$d_6$, 400 MHz) δ; 0.94(t, 3H, J=7.2 Hz), 1.74(sext, 2H, J=7.2 Hz), 2.34(s, 3H), 2.82(t, 2H, J=7.2 Hz), 6.68(m, 1H), 6.83(m, 1H), 6.88(s, 1H), 7.11(s, 1H), 7.22(s, 1H), 7.88(d, 2H, J=8.4 Hz), 7.94(d, 2H, J=8.4 Hz), 11.81(s, 1H), 12.86(brs, 1H).

Example 31

4-{2-[5-(5-Methyl-7-isopropenylbenzofuran-2-yl)pyrrolyl]}benzoic acid

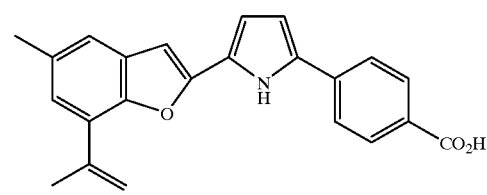

The title compound was prepared in a similar manner to that of Example 1 (D).

$^1$H-NMR (DMSO-$d_6$, 400 MHz) δ; 2.26(s, 3H), 2.38(s, 3H), 5.40(s, 1H), 5.88(s, 1H), 6.68(m, 1H), 6.83(m, 1H), 7.08(s, 1H), 7.15(s, 1H), 7.36(s, 1H), 7.88(d, 2H, J=8.4 Hz), 7.94(d, 2H, J=8.4 Hz), 11.84(s, 1H), 12.83(brs, 1H).

Example 32

4-{2-[5-(5-Methyl-7-isopropylbenzofuran-2-yl)pyrrolyl]}benzoic acid

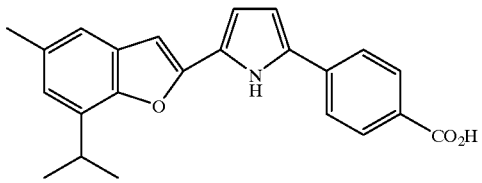

The title compound was prepared in a similar manner to that of Example 1 (D).

$^1$H-NMR (DMSO-d$_6$, 400 MHz) δ; 1.34(d, 6H, J=6.8 Hz), 2.35(s, 3H), 3.40(quint, 1H, J=6.8 Hz), 6.68(dd, 1H, J=2.4, 3.6 Hz), 6.82(dd, 1H, J=2.4, 3.6 Hz), 6.92(s, 1H), 7.10(s, 1H), 7.22(s, 1H), 7.88(d, 2H, J=8.8 Hz), 7.94(d, 2H, J=8.8 Hz), 11.79(s, 1H), 12.82(brs, 1H).

Example 33

4-{2-[5-(5-Methyl-7-ethylbenzofuran-2-yl)pyrrolyl]}benzoic acid

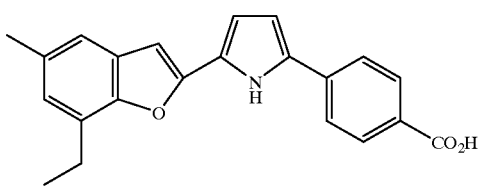

The title compound was prepared in a similar manner to that of Example 1 (D).

$^1$H-NMR (DMSO-d$_6$, 400 MHz) δ; 1.30(t, 3H, J=7.6 Hz), 2.35(s, 3H), 2.87(q, 2H, J=7.6 Hz), 6.69(m, 1H), 6.83(m, 1H), 6.90(s, 1H), 7.11(s, 1H), 7.22(s, 1H), 7.88(d, 2H, J=7.6 Hz), 7.94(d, 2H, J=7.6 Hz), 11.81(s, 1H), 12.84(brs, 1H).

Example 34

4-{2-[5-(4-Methyl-7-isopropylbenzofuran-2-yl)pyrrolyl]}benzoic acid

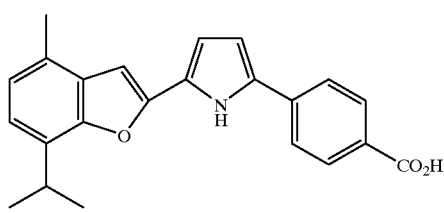

The title compound was prepared in a similar manner to that of Example 1 (D).

$^1$H-NMR (DMSO-d$_6$, 400 MHz) δ; 1.33(d, 6H, J=6.8 Hz), 2.44(s, 3H), 3.41(quint, 1H, J=6.8 Hz), 6.70(m, 1H), 6.84(m, 1H), 6.95(d, 1H, J=7.6 Hz), 7.00(d, 1H, J=7.6 Hz), 7.22(s, 1H), 7.88(d, 2H, J=7.6 Hz), 7.94(d, 2H, J=7.6 Hz), 11.80(s, 1H), 12.84(brs, 1H).

Example 35

4-{2-[5-(5-Methoxy-7-ethylbenzofuran-2-yl)pyrrolyl]}benzoic acid

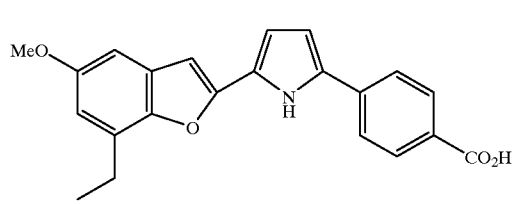

The title compound was prepared in a similar manner to that of Example 1 (D).

$^1$H-NMR (DMSO-d$_6$, 400 MHz) δ; 1.30(t, 3H, J=7.6 Hz), 2.87(q, 1H, J=7.6 Hz), 3.77(s, 3H), 6.69(m, 2H), 6.83(dd, 1H, J=2.4, 3.6 Hz), 6.97(d, 1H, J=2.4 Hz), 7.12(s, 1H), 7.88(d, 2H, J=8.4 Hz), 7.94(d, 2H, J=8.4 Hz), 11.80(s, 1H), 12.83(brs, 1H).

Example 36

4-{2-[5-(5-Methoxy-7-n-propylbenzofuran-2-yl)pyrrolyl]}benzoic acid

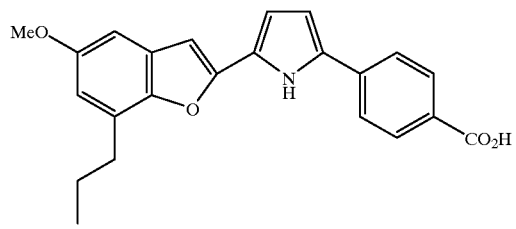

The title compound was prepared in a similar manner to that of Example 1(D).

$^1$H-NMR (DMSO-d$_6$, 400 MHz) δ; 0.94(t, 3H, J=7.2 Hz), 1.74(sext, 2H, J=7.6 Hz), 2.82(t, 2H, J=7.6 Hz), 3.76(s, 3H), 6.66(s, 1H), 6.68(m, 1H), 6.83(m, 1H), 6.98(s, 1H), 7.12(d, 1H, J=1.6 Hz), 7.88(d, 2H, J=8.4 Hz), 7.94(d, 2H, J=8.4 Hz), 11.80(s, 1H), 12.83(brs, 1H).

Example 37

4-{2-[5-(4-Methoxy-7-ethylbenzofuran-2-yl)pyrrolyl]}benzoic acid

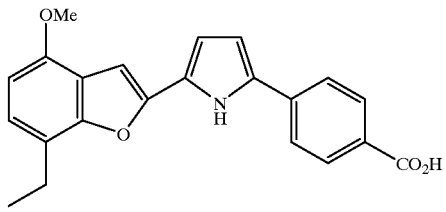

The title compound was prepared in a similar manner to that of Example 1 (D).

$^1$H-NMR (DMSO-d$_6$, 400 MHz) δ; 1.28(t, 3H, J=7.6 Hz), 2.84(q, 2H, J=7.6 Hz), 3.87(s, 3H), 6.68(s, 1H), 6.69(d, 1H, J=8.0 Hz), 6.82(s, 1H), 7.01(d, 1H, J=8.0 Hz), 7.23(s, 1H), 7.87(d, 2H, J=8.0 Hz), 7.94(d, 2H, J=8.0 Hz), 11.73(s, 1H), 12.80(brs, 1H).

Example 38

4-{2-[5-(4-Methoxy-7-n-propylbenzofuran-2-yl)pyrrolyl]}benzoic acid

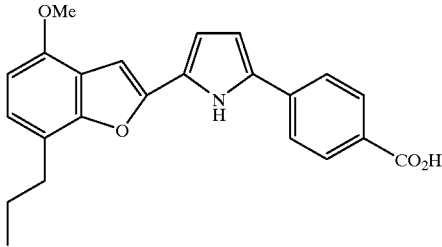

The title compound was prepared in a similar manner to that of Example 1 (D).

$^1$H-NMR (DMSO-d$_6$, 400 MHz) δ; 0.93(t, 3H, J=7.6 Hz), 1.70(m, 2H), 2.79(t, 2H, J=7.6 Hz), 3.88(s, 3H), 6.68(m, 2H), 6.82(m, 1H), 6.99(d, 1H, J=8.0 Hz), 7.23(s, 1H), 7.87(d, 2H, J=8.0 Hz), 7.93(d, 2H, J=8.0 Hz), 11.73(s, 1H), 12.68(brs, 1H).

Example 39

4-{2-[5-(Indano[4,5-b]furan-2-yl)pyrrolyl]}benzoic acid

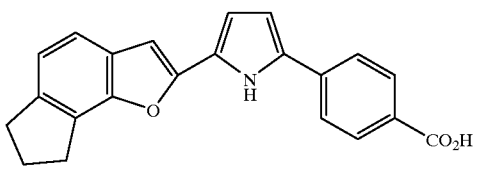

The title compound was prepared in a similar manner to that of Example 1 (D).

$^1$H-NMR (DMSO-d$_6$, 400 MHz) δ; 2.14(quint, 2H, J=7.2 Hz), 2.97(t, 2H, J=7.2 Hz), 3.10(t, 2H, J=7.2 Hz), 6.68(m, 1H), 6.82(m, 1H), 7.12(d, 1H, J=7.6 Hz), 7.17(s, 1H), 7.39(d, 1H, J=7.6 Hz), 7.88(d, 2H, J=7.6 Hz), 7.94(d, 2H, J=7.6 Hz), 11.81(s, 1H), 12.82(brs, 1H).

Example 40

4-{2-[5-(6,7-Dimethylbenzofuran-2-yl)pyrrolyl]}benzoic acid

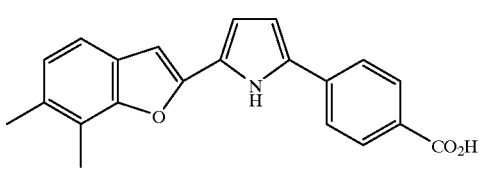

The title compound was prepared in a similar manner to that of Example 1 (D).

$^1$H-NMR (DMSO-d$_6$, 400 MHz) δ; 2.30(s, 3H), 2.42(s, 3H), 6.69–6.72(m, 1H), 6.81–6.84(m, 1H), 7.02(d, 1H, J=8.4 Hz), 7.11(s, 1H), 7.30(d, 1H, J=8.4 Hz), 7.88(d, 2H, J=8.4 Hz), 7.94(d, 2H, J=8.4 Hz), 11.78(s, 1H), 12.80(brs, 1H).

Example 41

4-{2-[5-(7-Phenoxybenzofuran-2-yl)pyrrolyl]}benzoic acid

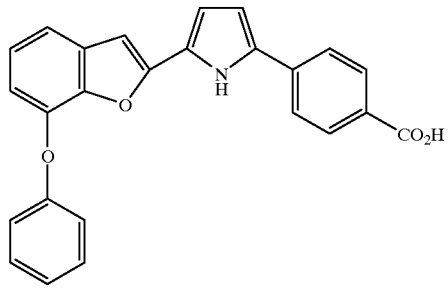

The title compound was prepared in a similar manner to that of Example 1 (D).

$^1$H-NMR (DMSO-d$_6$, 400 MHz) δ; 6.56–6.59(m, 1H), 6.79–6.84(m, 2H), 7.07–7.21(m, 4H), 7.25(s, 1H), 7.37–7.44(m, 3H), 7.87(d, 2H, J=8.4 Hz), 7.93(d, 2H, J=8.4 Hz), 11.91(s, 1H), 12.82(brs, 1H).

Example 42

4-{2-[5-(4-Fluoro-7-chlorobenzofuran-2-yl)pyrrolyl]}benzoic acid

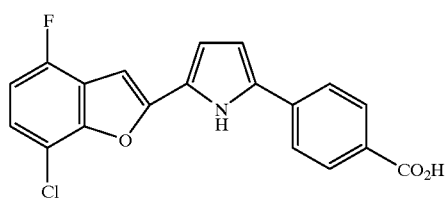

The title compound was prepared in a similar manner to that of Example 1 (D).

$^1$H-NMR (DMSO-d$_6$, 400 MHz) δ; 6.79–6.82(m, 1H), 6.86–6.89(m, 1H), 7.14(t, 1H, J=8.8 Hz), 7.37(dd, 1H, J=4.4, 8.4 Hz), 7.38(s, 1H), 7.90(d, 2H, J=8.4 Hz) 7.96(d, 2H, J=8.4 Hz), 11.97(d, 1H), 12.86(brs, 1H).

Example 43

4-{2-[5-(5-Fluoro-7-chlorobenzofuran-2-yl)pyrrolyl]}benzoic acid

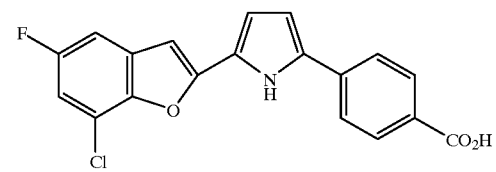

The title compound was prepared in a similar manner to that of Example 1 (D).

$^1$H-NMR (DMSO-d$_6$, 400 MHz) δ; 6.76–6.80(m, 1H), 6.84–6.88(m, 1H), 7.29(s, 1H), 7.34(dd, 1H, J=2.4, 8.4 Hz), 7.51(dd, 1H, J=2.4, 8.4 Hz), 7.90(d, 2H, J=8.4 Hz), 7.96(d, 2H, J=8.4 Hz), 12.00(s, 1H), 12.86(brs, 1H).

Example 44

4-{2-[5-(7-Trifluoromethylbenzofuran-2-yl)pyrrolyl]}benzoic acid

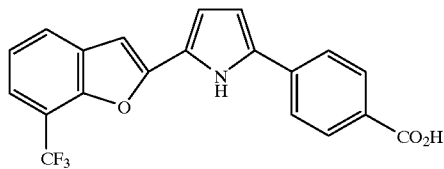

The title compound was prepared in a similar manner to that of Example 1 (D).

$^1$H-NMR (DMSO-$d_6$, 400 MHz) δ; 6.72–6.75(m, 1H), 6.85–6.88(m, 1H), 7.35(s, 1H), 7.40(t, 1H, J=7.6 Hz), 7.56 (d, 1H, J=7.6 Hz), 7.89(d, 2H, J=8.4 Hz), 7.96(d, 2H, J=8.4 Hz), 11.98(s, 1H), 12.83(brs, 1H)

Example 45

4-{2-[5-(5,7-Dichlorobenzofuran-2-yl)pyrrolyl]}benzoic acid

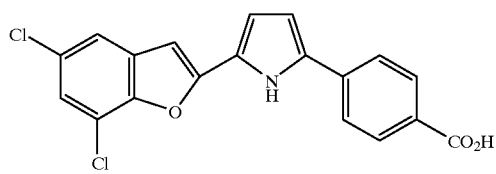

The title compound was prepared in a similar manner to that of Example 1 (D).

$^1$H-NMR (DMSO-$d_6$, 400 MHz) δ; 6.76–6.81(m, 1H), 6.84–6.89(m, 1H), 7.28(s, 1H), 7.46(d, 1H, J=2.0 Hz), 7.76(d, 1H, J=2.0 Hz), 7.89(d, 2H, J=8.4 Hz), 7.95(d, 2H, J=8.4 Hz), 12.00(brs, 1H).

Example 46

4-{2-[5-(4,7-Dichloro-3-methylbenzofuran-2-yl)pyrrolyl]}benzoic acid

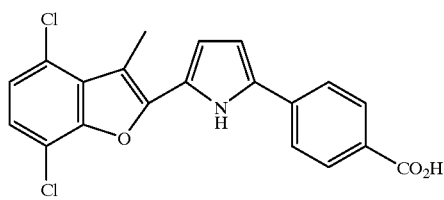

The title compound was prepared in a similar manner to that of Example 1 (D).

$^1$H-NMR (DMSO-$d_6$, 400 MHz) δ; 2.56(s, 3H), 6.69–6.73 (m, 1H), 6.89–6.93(m, 1H), 7.30(d, 1H, J=8.8 Hz), 7.39(d, 1H, J=8.8 Hz), 7.94(s, 4H), 11.97(brs, 1H), 12.82(brs, 1H).

Example 47

4-{2-[5-(3,4,7-Trimethylbenzofuran-2-yl)pyrrolyl]}benzoic acid

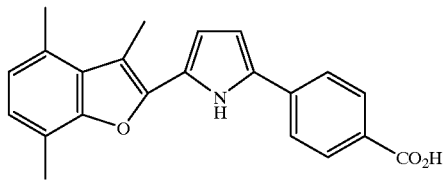

The title compound was prepared in a similar manner to that of Example 1(D).

$^1$H-NMR (DMSO-$d_6$, 400 MHz) δ; 2.50(s, 3H), 2.53(s, 3H), 2.59(s, 3H), 6.57(brs, 1H), 6.82–6.88(m, 2H), 6.94(d, 1H, J=7.2 Hz.), 7.90(s, 4H), 11.70(brs, 1H), 12.80(brs, 1H).

Example 48

4-{2-[5-(7-Isopropylbenzofuran-2-yl)pyrrolyl]}benzoic acid

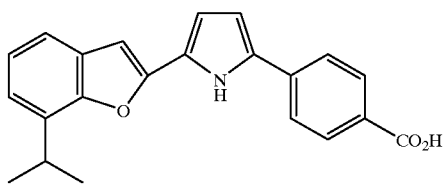

The title compound was prepared in a similar manner to that of Example 1 (D).

$^1$H-NMR (DMSO-$d_6$, 400 MHz) δ; 1.36(d, 6H, J=7.6 Hz), 3.45(quint, 1H, J=7.6 Hz), 6.70–6.73(m, 1H), 6.83–6.86(m, 1H), 7.09–7.16(m, 2H), 7.17(s, 1H), 7.43(d, 1H, J=7.6 Hz), 7.88(d, 2H, J=8.4 Hz), 7.95(d, 2H, J=8.4 Hz), 11.83(s, 1H), 12.82(brs, 1H).

Example 49

4-{2-[5-(4,6-Dimethylbenzofuran-2-yl)pyrrolyl]}benzoic acid

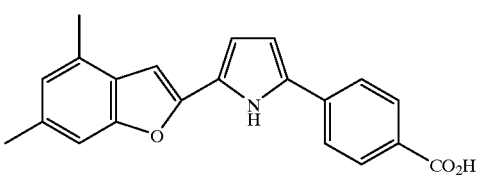

The title compound was prepared in a similar manner to that of Example 1 (D).

$^1$H-NMR (DMSO-$d_6$, 400 MHz) δ; 2.35(s, 3H), 2.43(s, 3H), 6.65–6.68(m, 1H), 6.81–6.84(m, 1H), 6.87(brs, 1H), 7.16–7.21(m, 2H), 7.88(d, 2H, J=8.4 Hz), 7.93(d, 2H, J=8.4 Hz), 11.82(s, 1H), 12.79(brs, 1H).

Example 50

4-{2-[5-(5,7-Dimethylbenzofuran-2-yl)pyrrolyl]}benzoic acid

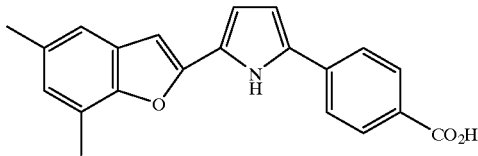

The title compound was prepared in a similar manner to that of Example 1 (D).

$^1$H-NMR (DMSO-$d_6$, 400 MHz) δ; 2.32(s, 3H), 2.45(s, 3H), 6.68–6.71(m, 1H), 6.80–6.83(m, 1H), 6.88(d, 1H, J=1.2 Hz), 7.10(s, 1H), 7.20(d, 1H, J=1.2 Hz), 7.86(d, 2H, J=8.4 Hz), 7.93(d, 2H, J=8.4 Hz), 11.78(s, 1H), 12.80(brs, 1H).

Example 51

4-{2-[5-(4-Methoxy-7-methylbenzofuran-2-yl)pyrrolyl)]}benzoic acid

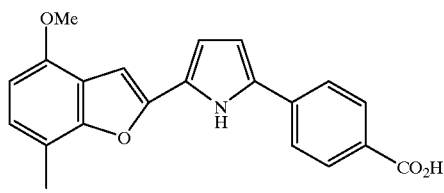

The title compound was prepared in a similar manner to that of Example 1 (D).

$^1$H-NMR (DMSO-$d_6$, 400 MHz) δ; 2.41(s, 3H), 3.86(s, 3H), 6.66–6.70(m, 2H), 6.81–6.85(m, 1H), 6.99(d, 1H, J=7.6 Hz), 7.24(s, 1H), 7.88(d, 2H, J=8.4 Hz), 7.94(d, 2H, J=8.4 Hz), 11.75(s, 1H), 12.80(brs, 1H).

Example 52

4-{2-[5-(7-Ethoxybenzofuran-2-yl)pyrrolyl]}benzoic acid

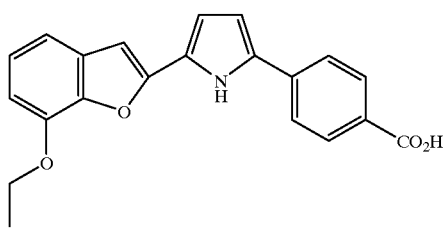

The title compound was prepared in a similar manner to that of Example 1 (D).

$^1$H-NMR (DMSO-$d_6$, 400 MHz) δ; 1.40(t, 3H, J=7.6 Hz), 4.25(q, 2H, J=7.6 Hz), 6.68–6.71(m, 1H), 6.81–6.84(m, 1H), 6.87(d, 1H, J=7.6 Hz), 7.12(t, 1H, J=7.6 Hz), 7.16–7.19(m, 2H), 7.89(d, 2H, J=8.4 Hz), 7.94(d, 2H, J=8.4 Hz), 11.87(s, 1H), 12.78(brs, 1H).

Example 53

4-{2-[5-(7-Chloro-4-methylbenzofuran-2-yl)pyrrolyl]}benzoic acid

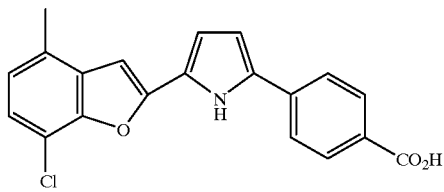

The title compound was prepared in a similar manner to that of Example 1 (D).

$^1$H-NMR (DMSO-$d_6$, 400 MHz) δ; 6.73–6.76(m, 1H), 6.84–6.87(m, 1H), 7.05(d, 1H, J=8.0 Hz), 7.22(d, 1H, J=8.0 Hz), 7.33(s, 1H), 7.90(d, 2H, J=8.4 Hz), 7.95(d, 2H, J=8.4 Hz), 11.93(s, 1H), 12.88(brs, 1H).

Example 54

4-{2-[5-(7-Methoxybenzofuran-2-yl)pyrrolyl]}benzoic acid

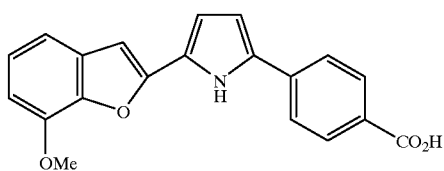

The title compound was prepared in a similar manner to that of Example 1 (D).

$^1$H-NMR (DMSO-$d_6$, 400 MHz) δ; 3.93(s, 3H), 6.68–6.71(m, 1H), 6.81–6.84(m, 1H), 6.88(dd, 1H, J=1.2, 8.0 Hz), 7.14(t, 1H, J=8.0 Hz), 7.18(s, 1H), 7.19(dd, 1H, J=1.2, 8.0 Hz), 7.89(d, 2H, J=8.4 Hz), 7.94(d, 2H, J=8.4 Hz), 11.87(s, 1H), 12.84(brs, 1H).

Example 55

4-{2-[5-(7-Ethylbenzofurn-2-yl)pyrrolyl]}benzoic acid

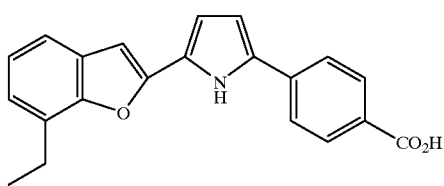

The title compound was prepared in a similar manner to that of Example 1 (D).

$^1$H-NMR (DMSO-$d_6$, 400 MHz) δ; 1.30(t, 3H, J=7.6 Hz), 2.90(q, 2H, J=7.6 Hz), 6.70–6.73(m, 1H), 6.82–6.85(m, 1H), 7.08(dd, 1H, J=0.8, 8.0 Hz), 7.14(t, 1H, J=8.0 Hz), 7.44(dd, 1H, J=0.8, 8.0 Hz), 7.88(d, 2H, J=8.4 Hz), 7.94(d, 2H, J=8.4 Hz), 11.82(s, 1H), 12.83(brs, 1H).

Example 56

4-{2-[5-(7-Phenylbenzofuran-2-yl)pyrrolyl]}benzoic acid

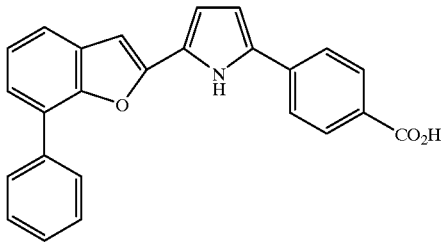

The title compound was prepared in a similar manner to that of Example 1 (D).

$^1$H-NMR (DMSO-d$_6$, 400 MHz) δ; 6.68–6.71(m, 1H), 6.83–6.86(m, 1H), 7.28(s, 1H), 7.32(t, 1H, J=7.6 Hz), 7.40–7.48(m, 2H), 7.56(t, 2H, J=7.6 Hz), 7.63(d, 1H, J=7.6 Hz), 7.88(d, 2H, J=8.4 Hz), 7.92–7.98(m, 4H), 11.90(s, 1H), 12.84(brs, 1H).

Example 57

4-{2-[5-(7-Methylbenzofuran-2-yl)pyrrolyl]}benzoic acid

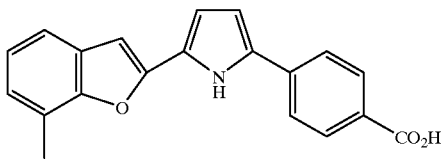

The title compound was prepared in a similar manner to that of Example 1 (D).

$^1$H-NMR (DMSO-d$_6$, 400 MHz) δ; 2.52(s, 3H), 6.71–6.74 (m, 1H), 6.83–6.86(m, 1H), 7.06(d, 1H, J=7.2 Hz), 7.12(t, 1H, J=7.2 Hz), 7.18(s, 1H), 7.43(d, 1H, J=7.2 Hz), 7.89(d, 2H, J=8.4 Hz), 7.95(d, 2H, J=8.4 Hz), 11.83(s, 1H), 12.82 (brs, 1H).

Example 58

4-{2-[5-(4,5-Dimethylbenzofuran-2-yl)pyrrolyl]}benzoic acid

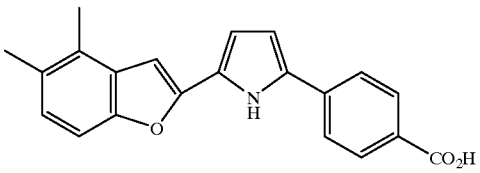

The title compound was prepared in a similar manner to that of Example 1 (D).

$^1$H-NMR (DMSO-d$_6$, 400 MHz) δ; 2.34(s, 3H), 2.46(s, 3H), 6.70(dd, 1H, J=2.4, 3.6 Hz), 6.83(dd.1H, J=2.4, 3.6 Hz), 7.11(s, 1H), 7.22(s, 1H), 7.87–7.95(m, 4H), 11.80(s, 1H), 12.79(s, 1H).

Example 59

4-{2-[5-(4-Methylbenzofuran-2-yl)pyrrolyl]}benzoic acid

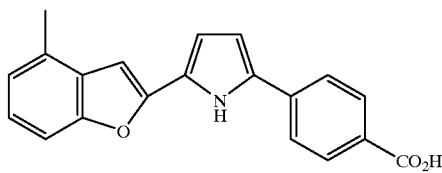

The title compound was prepared in a similar manner to that of Example 1 (D).

$^1$H-NMR (DMSO-d$_6$, 400 MHz) δ; 2.51(s, 3H), 6.72–6.73 (m, 1H), 6.84–6.85(m, 1H), 7.06(d, 1H, J=7.2 Hz), 7.12(dd, 1H, J=5.2, 5.2 Hz), 7.10(s, 1H) 7.44(d, 1H, J=7.6 Hz), 7.89(d, 2H, J=8.4 Hz), 7.95(d, 2H, J=8.4 Hz).

Example 60

4-{2-[5-(4-Chlorobenzofuran-2-yl)pyrrolyl]}benzoic acid

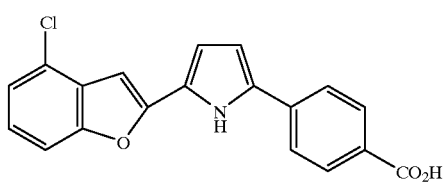

The title compound was prepared in a similar manner to that of Example 1 (D).

$^1$H-NMR (DMSO-d$_6$, 400 MHz) δ; 6.78–6.80(m, 1H), 6.86–6.87(m, 1H), 7.24–7.33(m, 3H), 7.57(d, 1H, J=8.0 Hz), 7.92(d, 2H, J=8.4 Hz), 7.95(d, 2H, J=8.4 Hz), 11.97(s, 1H), 12.87(brs, 1H).

Example 61

4-{2-[5-(5-Chlorobenzofuran-2-yl)pyrrolyl]}benzoic acid

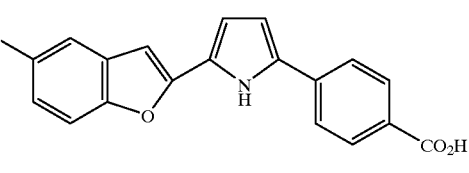

The title compound was prepared in a similar manner to that of Example 1 (D).

$^1$H-NMR (DMSO-d$_6$, 400 MHz) δ; 6.74–6.75(m, 1H), 6.82–6.84(m, 1H), 7.20(s, 1H), 7.25(dd, 1H, J=2.0, 8.4 Hz), 7.58(d, 1H, J=8.8 Hz), 7.73(d, 1H, J=2.0 Hz), 7.87(brd, 2H, J=8.4 Hz), 7.94(brd, 2H, J=8.4 Hz).

Example 62

4-{2-[5-(4,7-Dimethylbenzofuran-2-yl)furyl]}benzoic acid

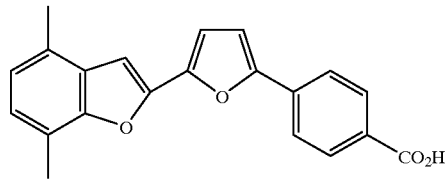

The title compound was prepared in a similar manner to that of Example 1 (D).

¹H-NMR (DMSO-$d_6$, 400 MHz) δ; 2.46(s, 6H), 6.97(d, 1H, J=7.6 Hz), 7.04(d, 1H, J=7.6 Hz), 7.11(d, 1H, J=4.0 Hz), 7.35(d, 1H, J=4.0 Hz), 7.40(s, 1H), 7.95(d, 2H, J=8.4 Hz), 8.01(d, 2H, J=8.4 Hz).

Example 63

4-{2-[5-(4,7-Dimethylbenzofuran-2-yl)thienyl]}benzoic acid

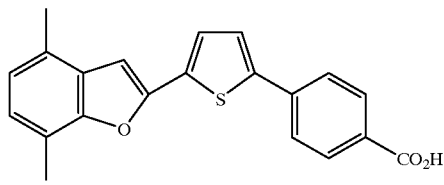

The title compound was prepared in a similar manner to that of Example 1 (D).

¹H-NMR (DMSO-$d_6$, 400 MHz) δ; 2.42(s, 6H), 6.96(d, 1H, J=7.2 Hz), 7.02(d, 1H, J=7.2 Hz), 7.38(s, 1H), 7.68(d, 1H, J=4.0 Hz), 7.76(d, 1H, J=4.0 Hz), 7.85(d, 2H, J=7.6 Hz), 7.98(d, 2H, J=7.6 Hz).

Example 64

4-{2-[5-(4,7-Dichlorobenzofuran-2-yl)furyl]}benzoic acid

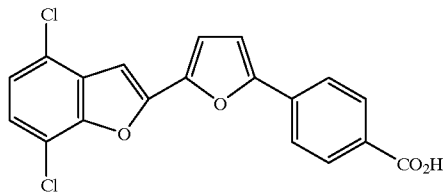

The title compound was prepared in a similar manner to that of Example 1 (D).

¹H-NMR (DMSO-$d_6$, 400 MHz) δ; 7.30(d, 1H, J=3.6 Hz), 7.38–7.42(m, 2H), 7.47(d, 1H, J=8.0 Hz), 7.52(s, 1H), 7.97–8.03(m, 4H).

Example 65

4-{2-[5-(4,7-Dichlorobenzofuran-2-yl)thienyl]}benzoic acid

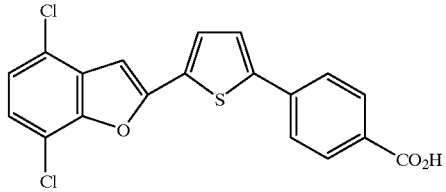

The title compound was prepared in a similar manner to that of Example 1 (D).

¹H-NMR (DMSO-$d_6$, 400 MHz) δ; 7.39(d, 1H, J=8.0 Hz), 7.45(d, 1H, J=8.0 Hz), 7.55(s, 1H), 7.80(d, 1H, J=4.4 Hz), 7.84–7.90(m, 3H), 7.98(d, 2H, J=8.4 Hz).

Example 66

5-{2-[5-(4,7-Dimethylbenzofuran-2-yl)pyrrolyl]}thiophene-2-carboxylic acid

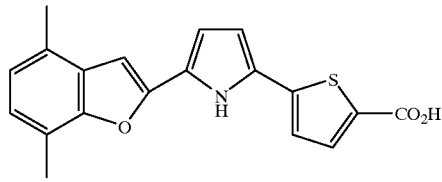

The title compound was prepared in a similar manner to that of Example 1 (D).

¹H-NMR (DMSO-$d_6$, 400 MHz) δ; 2.43(s, 3H), 2.45(s, 3H), 6.62–6.65(m, 1H), 6.66–6.69(m, 1H), 6.92(d, 1H, J=7.6 Hz), 6.96(d, 1H, J=7.6 Hz), 7.19(s, 1H), 7.45(d, 1H, J=3.6 Hz), 7.67(d, 1H, J=3.6 Hz), 11.96(brs, 1H), 12.97(brs, 1H).

Example 67

4-{2-[5-(2,3,4,7-Tetramethylbenzofuran-5-yl)pyrrolyl]}benzoic acid

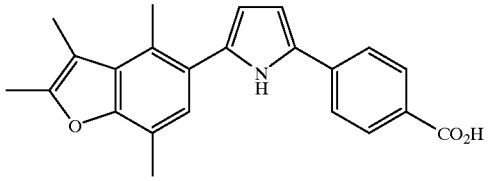

The title compound was prepared in a similar manner to that of Example 1 (D).

¹H-NMR (DMSO-$d_6$, 400 MHz) δ; 2.28(s, 3H), 2.35(s, 3H), 2.37(s, 3H), 2.57(s, 3H), 6.16(brs, 1H), 6.75(brs, 1H), 7.06(s, 1H), 7.80(d, 2H, J=8.4 Hz), 7.86(d, 2H, J=8.4 Hz), 11.36(brs, 1H), 12.69(brs, 1H).

Example 68

4-{2-[5-(2,3-Dimethylbenzofuran-5-yl)pyrrolyl]}benzoic acid

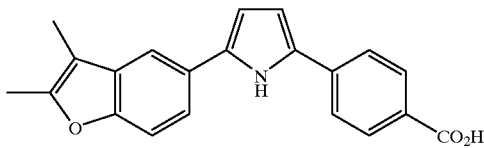

The title compound was prepared in a similar manner to that of Example 1 (D).

$^1$H-NMR (DMSO-$d_6$, 400 MHz) δ; 2.18(s, 3H), 2.35(s, 3H), 6.59(brs, 1H), 6.73(brs, 1H), 7.42(d, 1H, J=8.2 Hz), 7.61(dd, 1H, J=2.0, 8.2 Hz), 7.82–7.94(m, 5H), 11.36(brs, 1H), 12.76(brs, 1H).

Example 69

4-{2-[5-(7-Chlorobenzothiophen-2-yl) pyrrolyl]}benzoic acid

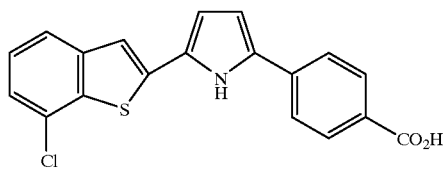

The title compound was prepared in a similar manner to that of Example 1 (D).

$^1$H-NMR (DMSO-$d_6$, 400 MHz) δ; 6.65–6.68(m, 1H), 6.80–6.83(m, 1H), 7.38–7.42(m, 2H), 7.76–7.82(m, 1H), 7.80(s, 1H), 7.89(d, 2H, J=8.4 Hz), 7.94(d, 2H, J=8.4 Hz), 11.87(s, 1H), 12.82(brs, 1H).

Example 70

4-{2-[5-(5,7-Dimethylbenzothiophen-2-yl)pyrrolyl]}benzoic acid

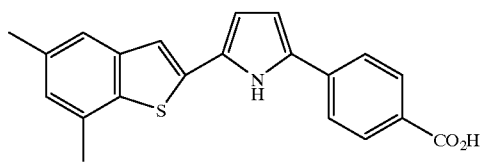

The title compound was prepared in a similar manner to that of Example 1 (D).

$^1$H-NMR (DMSO-$d_6$, 400 MHz) δ; 2.36(s, 3H), 2.42(s, 3H), 6.54–6.56(m, 1H), 6.77–6.79(m, 1H), 6.96(s, 1H), 7.43(s, 1H), 7.71(s, 1H), 7.88(d, 2H, J=8.4 Hz), 7.93(d, 2H, J=8.4 Hz), 11.76(s, 1H), 12.76(brs, 1H).

Example 71

4-{2-[5-(7-n-Propylbenzothiophen-2-yl)pyrrolyl]}benzoic acid

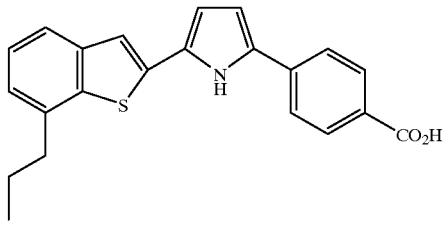

The title compound was prepared in a similar manner to that of Example 1 (D).

$^1$H-NMR (DMSO-$d_6$, 400 MHz) δ; 0.96(t, 3H, J=7.2 Hz), 1.75(sext, 2H, J=7.2 Hz), 2.78(t, 2H, J=7.2 Hz), 6.56–6.59 (m, 1H), 6.78–6.81(m, 1H), 7.13(d, 1H, J=7.2 Hz), 7.30(t, 1H, J=7.2 Hz), 7.63(d, 1H, J=7.2 Hz), 7.78(s, 1H), 7.89(d, 2H, J=8.4 Hz), 7.93(d, 2H, J=8.4 Hz), 11.77(s, 1H), 12.78 (brs, 1H).

Example 72

4-{2-[5-(5-Fluoro-7-methylbenzothiophen-2-yl)pyrrolyl]}benzoic acid

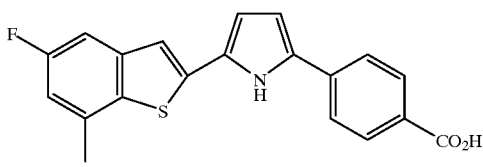

The title compound was prepared in a similar manner to that of Example 1 (D).

$^1$H-NMR (DMSO-$d_6$, 400 MHz) δ; 3.32(s, 3H), 6.59–6.62 (m, 1H), 6.79–6.82(m, 1H), 7.05(dd, 1H, J=2.4, 9.0 Hz), 7.48(dd, 1H, J=2.4, 9.0 Hz), 7.77(s, 1H), 7.89(d, 2H, J=8.4 Hz), 7.94(d, 2H, J=8.4 Hz), 11.85(s, 1H), 12.78(brs, 1H).

Example 73

4-{2-[5-(5-Chloro-7-methylbenzothiophen-2-yl)pyrrolyl]}benzoic acid

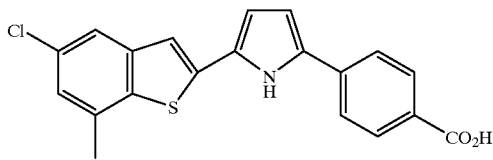

The title compound was prepared in a similar manner to that of Example 1 (D).

$^1$H-NMR (DMSO-$d_6$, 400 MHz) δ; 3.30(s, 3H), 6.60–6.62 (m, 1H), 6.79–6.82(m, 1H), 7.19(d, 1H, J=1.6 Hz), 7.73(d, 1H, J=1.6 Hz), 7.75(s, 1H), 7.88(d, 2H, J=8.4 Hz), 7.94(d, 2H, J=8.4 Hz), 11.86(s, 1H), 12.80(brs, 1H).

Example 74

4-{2-[5-(7-Ethylbenzothiophen-2-yl)pyrrolyl]}benzoic acid

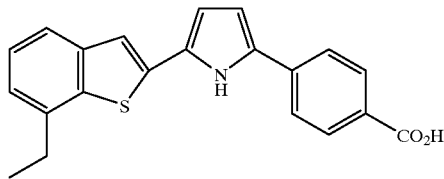

The title compound was prepared in a similar manner to that of Example 1 (D).

$^1$H-NMR (DMSO-d$_6$, 400 MHz) δ; 1.32(t, 3H, J=7.6 Hz), 2.82(q, 2H, J=7.6 Hz), 6.57–6.59(m, 1H), 6.78–6.81(m, 1H), 7.15(d, 1H, J=7.6 Hz), 7.31(t, 1H, J=7.6 Hz), 7.64(d, 1H, J=7.6 Hz), 7.79(s, 1H), 7.89(d, 2H, J=8.4 Hz), 7.94(d, 2H, J=8.4 Hz), 11.78(s, 1H), 12.83(brs, 1H).

Example 75

4-{2-[5-(7-Chloro-4-methylbenzothiophen-2-yl)pyrrolyl]}benzoic acid

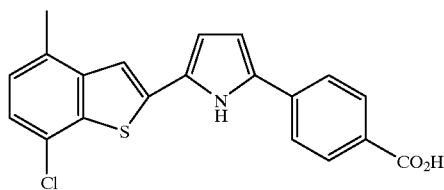

The title compound was prepared in a similar manner to that of Example 1 (D).

$^1$H-NMR (DMSO-d$_6$, 400 MHz) δ; 2.56(s, 3H), 6.65–6.67(m, 1H), 6.80–6.83(m, 1H), 7.20(d, 1H, J=7.6 Hz), 7.29(d, 1H, J=7.6 Hz), 7.89(d, 2H, J=8.4 Hz), 7.93(s, 1H), 7.95(d, 2H, J=8.4 Hz), 11.83(s, 1H), 12.82(brs, 1H).

Example 76

4-{2-[5-(7-Isopropylbenzothiophen-2-yl)pyrrolyl]}benzoic acid

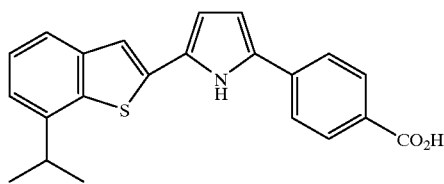

The title compound was prepared in a similar manner to that of Example 1 (D).

$^1$H-NMR (DMSO-d$_6$, 400 MHz) δ; 1.33(d, 6H, J=7.6 Hz), 3.10(quint, 1H, J=7.6 Hz), 6.56–6.59(m, 1H), 6.78–6.81(m, 1H), 7.20(d, 1H, J=7.6 Hz), 7.33(t, 1H, J=7.6 Hz) 7.63(d, 1H, J=7.6 Hz), 7.78(s, 1H), 7.89(d, 2H, J=8.4 Hz), 7.94(d, 2H, J=8.4 Hz), 11.78(s, 1H), 12.82(brs, 1H).

Example 77

4-{2-[5-(4,7-Dimethylbenzothiophen-2-yl)pyrrolyl]}benzoic acid

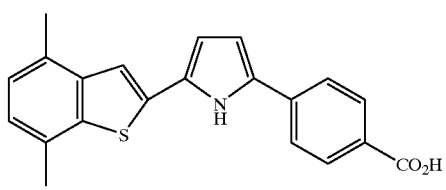

The title compound was prepared in a similar manner to that of Example 1 (D).

$^1$H-NMR (DMSO-d$_6$, 400 MHz) δ; 2.42(s, 3H), 2.54(s, 3H), 6.56–6.59(m, 1H), 6.78–6.81(m, 1H), 7.02(d, 1H, J=6.8 Hz), 7.08(d, 1H, J=6.8 Hz), 7.89(s, 1H), 7.90(d, 2H, J=8.4 Hz), 7.94(d, 2H, J=8.4 Hz), 11.76(s, 1H), 12.83(brs, 1H).

Example 78

4-{2-[5-(4,7-Dichlorobenzothiophen-2-yl)pyrrolyl]}benzoic acid

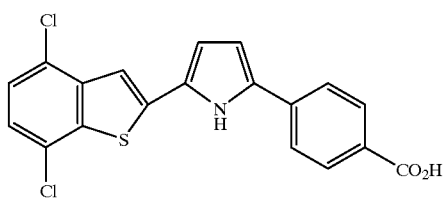

The title compound was prepared in a similar manner to that of Example 1 (D).

$^1$H-NMR (DMSO-d$_6$, 400 MHz) δ; 6.73–6.76(m, 1H), 6.82–6.85(m, 1H), 7.41(d, 1H, J=8.0 Hz), 7.49(d, 1H, J=8.0 Hz), 7.91(d, 2H, J=8.4 Hz), 7.96(d, 2H, J=8.4 Hz), 7.98(s, 1H), 11.98(s, 1H), 12.86(brs, 1H).

Example 79

4-{2-[5-(3,4,7-Trimethylbenzothiophen-2-yl)pyrrolyl]}benzoic acid

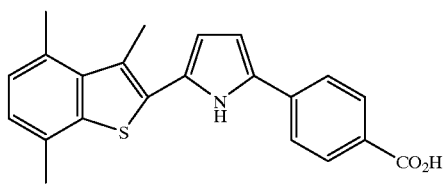

The title compound was prepared in a similar manner to that of Example 1 (D).

$^1$H-NMR (DMSO-d$_6$, 400 MHz) δ; 2.40(s, 3H), 2.66(s, 3H), 2.72(s, 3H), 6.38–6.41(m, 1H), 6.79–6.82(m, 1H), 6.94–7.10(m, 2H), 7.78–7.96(m, 4H), 11.65(s, 1H).

Example 80

4-{2-[5-(8-Methoxymethylnaphthalen-2-yl)-pyrrolyl]}benzoic acid

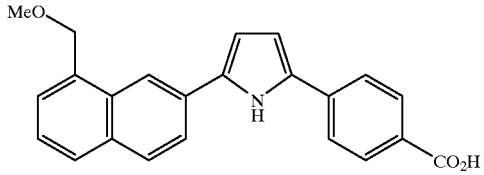

The title compound was prepared in a similar manner to that of Example 1 (D).

$^1$H-NMR (DMSO-$d_6$, 400 MHz) δ; 3.41(s, 3H), 4.97(s, 2H), 6.81(m, 1H), 6.83(m, 1H), 7.40(t, 1H, J=7.6 Hz), 7.50(d, 1H, J=6.8 Hz), 7.81(d, 1H, J=8.0 Hz), 7.90–7.97(m, 6H), 8.34(s, 1H), 11.63(s, 1H), 12.83(brs, 1H).

Example 81

4-{2-[5-(8-Ethoxynaphthalen-2-yl)pyrrolyl]}-benzoic acid

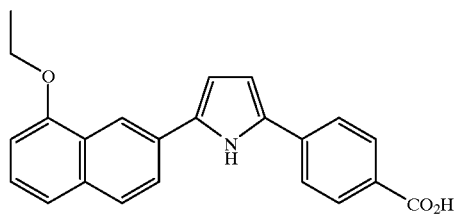

The title compound was prepared in a similar manner to that of Example 1 (D).

$^1$H-NMR (DMSO-$d_6$, 400 MHz) δ; 1.51(t, 3H, J=6.8 Hz), 4.26(q, 2H, J=6.8 Hz), 6.73(m, 1H), 6.83(m, 1H), 6.95(d, 1H, J=7.6 Hz), 7.34(t, 1H, J=8.0 Hz), 7.41(d, 1H, J=8.0 Hz), 7.86(d, 1H, J=8.8 Hz), 7.92–7.95(m, 5H), 8.48(s, 1H), 11.70(s, 1H).

Example 82

4-{2-[5-(8-Isopropoxynaphthalen-2-yl)-pyrrolyl]}benzoic acid

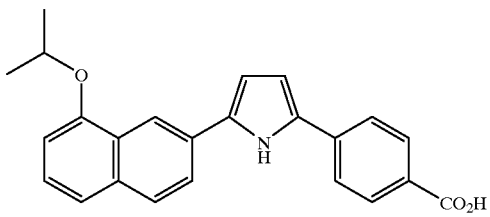

The title compound was prepared in a similar manner to that of Example 1 (D).

$^1$H-NMR (DMSO-$d_6$, 400 MHz) δ; 1.43(d, 6H, J=6.0 Hz), 4.82(quint, 1H, J=6.0 Hz), 6.71(m, 1H), 6.82(m, 1H), 7.33(t, 1H, J=8.0 Hz), 7.39(d, 1H, J=7.6 Hz), 7.85(d, 1H, J=8.8 Hz), 7.93(m, 5H), 8.44(s, 1H), 11.70(s, 1H).

Example 83

4-{2-[5-(8-Methoxynaphthalen-2-yl)-pyrrolyl]}benzoic acid

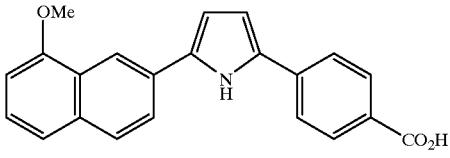

The title compound was prepared in a similar manner to that of Example 1 (D).

$^1$H-NMR (DMSO-$d_6$, 400 MHz) δ; 4.01(s, 3H), 6.76(m, 1H), 6.82(m, 1H), 6.97(d, 1H, J=7.6 Hz), 7.36(t, 1H, J=8.0 Hz), 7.42(d, 1H, J=8.0 Hz), 7.85(d, 1H, J=8.8 Hz), 7.90–7.96(m, 5H), 8.55(s, 1H), 11.69(s, 1H).

Example 84

4-{2-[5-(8-(2-Furyl)naphthalen-2-yl)-pyrrolyl]}benzoic acid

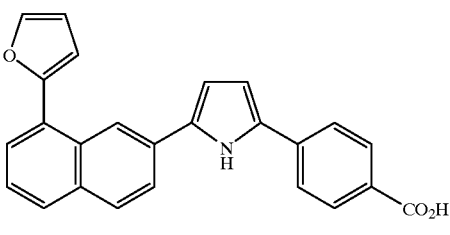

The title compound was prepared in a similar manner to that of Example 1 (D).

$^1$H-NMR (DMSO-$d_6$, 400 MHz) δ; 6.72(dd, 1H, J=2.0, 3.6 Hz), 6.75(dd, 1H, J=1.6, 3.2 Hz), 6.83(dd, 1H, J=2.0, 3.6 Hz), 7.05(d, 1H, J=3.2 Hz), 7.50(t, 1H, J=8.0 Hz), 7.74(dd, 1H, J=1.2, 7.2 Hz), 7.88–7.94(m, 5H), 8.01(s, 2H), 8.62(s, 1H), 11.70(s, 1H).

Example 85

4-{2-[5-(7-Hydroxy-8-isopropenylnaphthalen-2-yl)pyrrolyl]}benzoic acid

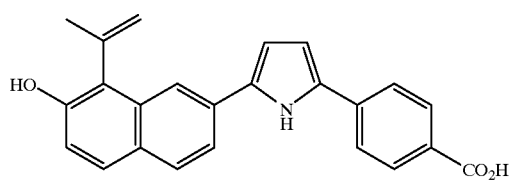

The title compound was prepared in a similar manner to that of Example 1 (D).

$^1$H-NMR (DMSO-$d_6$, 400 MHz) δ; 2.10(s, 3H), 4.89(m, 1H), 5.49(m, 1H), 6.61(dd, 1H, J=2.4, 4.0 Hz), 6.79(dd, 1H, J=2.4, 3.6 Hz), 7.09(dd, 1H, J=2.0, 8.4 Hz), 7.64(d, 1H, J=9.2 Hz), 7.71(d, 1H, J=8.8 Hz), 7.89(d, 2H, J=8.4 Hz), 7.92(d, 2H, J=8.4 Hz), 8.01(s, 1H), 9.40(s, 1H), 11.66(s, 1H).

Example 86

4-{2-[5-(8-(1-Methoxyethyl)naphthalen-2-yl)pyrrolyl]}benzoic acid

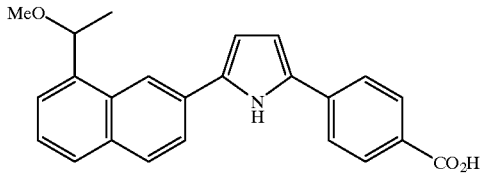

The title compound was prepared in a similar manner to that of Example 1 (D).

$^1$H-NMR (DMSO-$d_6$, 400 MHz) δ; 1.50(d, 3H, J=6.0 Hz), 3.24(s, 3H), 5.32(g, 1H, J=6.4 Hz), 6.82(s, 2H), 7.45(t, 1H, J=7.6 Hz), 7.53(d, 1H, J=6.8 Hz), 7.78(d, 1H, J=7.6 Hz), 7.89–7.97(m, 6H), 8.41(s, 1H), 11.58(s, 1H).

Example 87

4-{2-[5-(8-(2-Thienyl)naphthalen-2-yl)-pyrrolyl]}benzoic acid

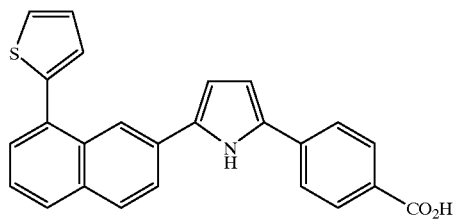

The title compound was prepared in a similar manner to that of Example 1 (D).

$^1$H-NMR (DMSO-$d_6$, 400 MHz) δ; 6.62(m, 1H), 6.81(m, 1H), 7.29(m, 1H), 7.45(m, 1H), 7.49(t, 1H, J=7.6 Hz), 7.57(d, 1H, J=7.2 Hz), 7.73(m, 1H), 7.85–7.94(m, 5H), 8.03(s, 2H), 8.47(s, 1H), 11.66(s, 1H).

Example 88

4-{2-[5-(5-Methoxy-8-isopropenylnaphthalen-2-yl)pyrrolyl]}benzoic acid

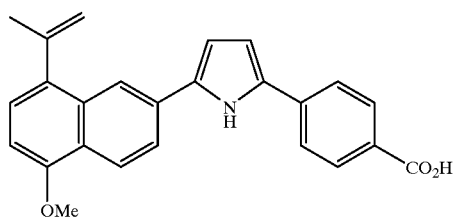

The title compound was prepared in a similar manner to that of Example 1 (D).

$^1$H-NMR (DMSO-$d_6$ 400 MHz) δ; 2.20(s, 3H), 3.96(s, 3H) 1H), 5.42(s, 1H), 6.70(m, 1H), 6.81(m, 1H), 6.87(d, 1H, J=8.0 Hz), 7.24(d, 1H, J=8.0 Hz), 7.88–7.96(m, 5H), 8.19 (m, 2H), 11.66(s, 1H).

Example 89

4-{2-[5-(5-Methoxy-8-isopropenylnaphthalen-2-yl)pyrrolyl]}benzoic acid

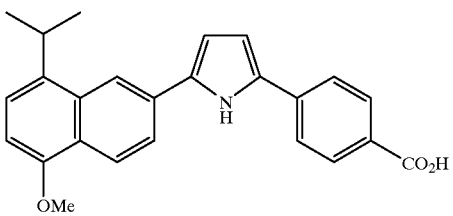

The title compound was prepared in a similar manner to that of Example 1 (D).

$^1$H-NMR (DMSO-$d_6$ 400 MHz) δ; 1.33(d, 6H, J=6.8 Hz), 3.85(quint, 1H, J=6.8 Hz), 3.93(s, 3H), 6.82(s, 2H), 6.86(d, 1H, J=8.0 Hz), 7.32(d, 1H, J=8.0 Hz), 7.86–7.96(m, 5H), 8.16(d, 1H, J=8.4 Hz), 8.41(s, 1H), 11.62(S, 1H).

Example 90

4-{2-[5-(5-Methoxy-8-ethylnaphthalen-2-yl)pyrrolyl]}benzoic acid

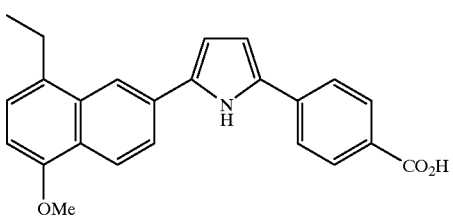

The title compound was prepared in a similar manner to that of Example 1 (D).

$^1$H-NMR (DMSO-$d_6$, 400 MHz) δ; 1.31(t, 3H, J=7.2 Hz), 3.09(q, 2H, J=7.2 Hz), 3.93(s, 3H), 6.80–6.84(m, 3H), 7.25(d, 1H, J=8.0 Hz), 7.88–7.96(m, 5H), 8.15(d, 1H, J=8.8 Hz), 8.33(s, 1H).

Example 91

4-{2-[5-(5-Methoxy-8-methylnaphthalen-2-yl)pyrrolyl]}benzoic acid

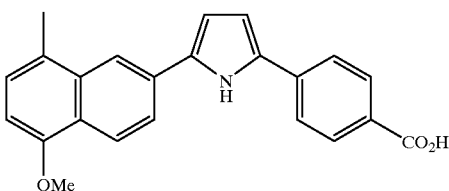

The title compound was prepared in a similar manner to that of Example 1 (D).

$^1$H-NMR (DMSO-$d_6$, 400 MHz) δ; 2.63(s, 3H), 3.92(s, 3H), 6.77–6.82(m, 3H), 7.24(d, 1H, J=8.0 Hz), 7.86–7.95(m, 5H), 8.13(d, 1H, J=8.8 Hz), 8.28(s, 1H), 11.62(s, 1H).

Example 92

4-{2-[5-(7-Chloro-5-methoxybenzofuran-2-yl)pyrrolyl]}benzoic acid

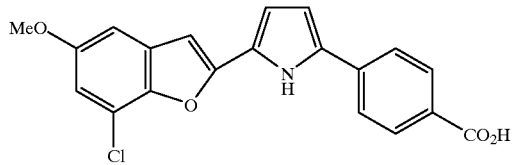

The title compound was prepared in a similar manner to that of Example 1 (D).

$^1$H-NMR (DMSO-$d_6$, 400 MHz) δ; 3.80(s, 3H), 6.72–6.75 (m, 1H), 6.84–6.86(m, 1H), 6.95(d, 1H, J=2.0 Hz), 7.18(d, 1H, J=2.4 Hz), 7.22(s, 1H), 7.89(d, 2H, J=8.4 Hz), 7.95(d, 2H, J=8.4 Hz), 11.94(brs, 1H).

Example 93

4-{2-[5-(7-Chloro-5-methylbenzofuran-2-yl)pyrrolyl]}benzoic acid

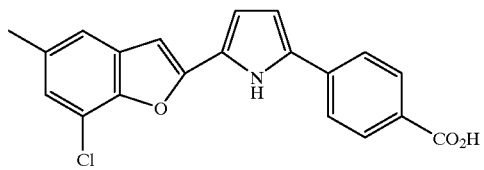

The title compound was prepared in a similar manner to that of Example 1 (D).

$^1$H-NMR (DMSO-$d_6$, 400 MHz) δ; 2.37(s, 3H), 6.71–6.75 (m, 1H), 6.83–6.87(m, 1H), 7.17(d, 1H, J=0.4 Hz), 7.21(s, 1H), 7.40(d, 1H, J=0.4 Hz), 7.89(d, 2H, J=8.4 Hz), 7.95(d, 2H, J=8.8 Hz), 11.93(brs, 1H).

Example 94

4-{2-[5-(7-Chloro-5-ethylbenzofuran-2-yl)-pyrrolyl]}benzoic acid

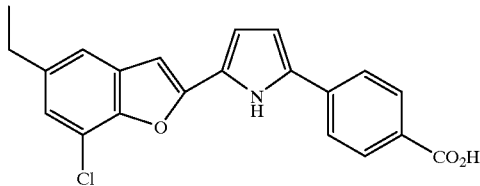

The title compound was prepared in a similar manner to that of Example 1 (D).

$^1$H-NMR (DMSO-$d_6$, 400 MHz) δ; 1.22(d, 3H, J=7.5 Hz), 2.67(q, 2H, J=7.5 Hz), 6.73(dd, 1H, J=2.4, 3.6 Hz), 6.85(dd, 1H, J=2.8, 3.2 Hz), 7.18–7.19(m, 1H), 7.23(s, 1H), 7.43–7.44(m, 1H), 7.89(d, 2H, J=8.4 Hz), 7.95(d, 2H, J=8.8 Hz), 11.93(brs, 1H).

Example 95

4-{2-[5-(7-Chloro-4,5-dimethylbenzofuran-2-yl)pyrrolyl]}benzoic acid

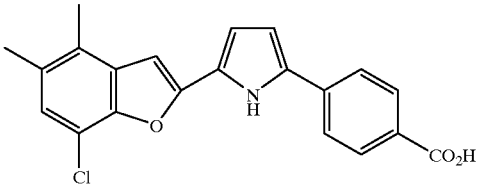

The title compound was prepared in a similar manner to that of Example 1 (D).

$^1$H-NMR (DMSO-$d_6$, 400 MHz) δ; 2.29(s, 3H), 2.36(s, 3H), 6.70–6.74(m, 1H), 6.82–6.86(m, 1H), 7.15(s, 1H), 7.31(s, 1H), 7.89(d, 2H, J=7.6 Hz), 7.95(d, 2H, J=7.6 Hz), 11.91(brs, 1H).

Example 96

4-{2-[5-(5-Ethyl-7-methylbenzofuran-2-yl)-pyrrolyl]}benzoic acid

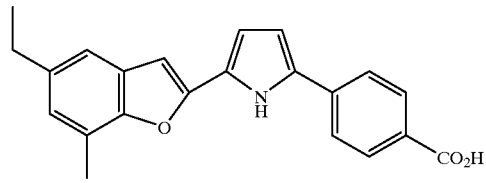

The title compound was prepared in a similar manner to that of Example 1 (D).

$^1$H-NMR (DMSO-$d_6$, 400 MHz) δ; 1.21(t, 3H, J=7.6 Hz), 6.63(q, 2H, J=7.6 Hz), 6.67–6.72(m, 1H), 6.80–6.85(m, 1H), 6.88–6.93(m, 1H), 7.12(s, 1H), 7.22–7.26(m, 1H), 7.88(d, 2H, J=8.4 Hz), 7.94(d, 2H, J=8.4 Hz), 11.80(brs, 1H).

Example 97

4-{2-[5-(7-Chloro-5-isopropenylbenzofuran-2-yl)pyrrolyl]}benzoic acid

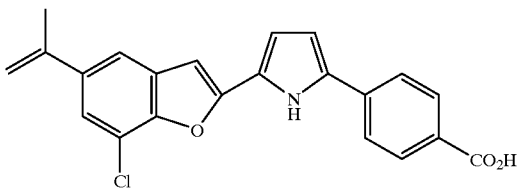

The title compound was prepared in a similar manner to that of Example 1 (D).

$^1$H-NMR (DMSO-$d_6$, 400 MHz) δ; 2.16(s, 3H), 5.13–5.14 (m, 1H), 5.47–5.48(m, 1H), 6.74–6.78(m, 1H), 6.84–6.88 (m, 1H), 7.28(s, 1H), 7.47(d, 1H, J=1.6 Hz), 7.73(d, 1H, J=1.6 Hz), 7.90(d, 2H, J=8.4 Hz), 7.95(d, 2H, J=8.8 Hz), 11.97(brs, 1H).

Example 98

4-{2-[5-(5,7-Dichloro-3-methylbenzofuran-2-yl)pyrrolyl]}benzoic acid

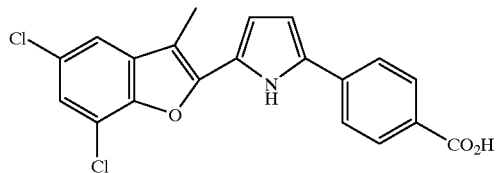

The title compound was prepared in a similar manner to that of Example 1 (D).

$^1$H-NMR (DMSO-$d_6$, 400 MHz) δ; 2.35(s, 3H), 6.66–6.70 (m, 1H), 6.80–6.84(m, 1H), 7.45–7.49(m, 1H), 7.68–7.72 (m, 1H), 7.80–7.90(m, 4H), 11.84(brs, 1H).

Example 99

4-{2-[5-(7-Chloro-4-ethylbenzofuran-2-yl)-pyrrolyl]}benzoic acid

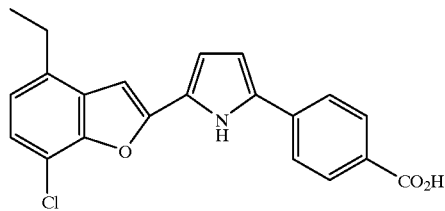

The title compound was prepared in a similar manner to that of Example 1 (D).

$^1$H-NMR (DMSO-$d_6$, 400 MHz) δ; 1.28(t, 3H, J=7.6 Hz), 2.83(q, 2H, J=7.6 Hz), 6.74–6.76(m, 1H), 6.84–6.87(m, 2H), 7.07(d, 1H, J=8.0 Hz), 7.25(d, 1H, J=8.0 Hz), 7.37(s, 1H), 7.90(d, 2H, J=8.4 Hz), 7.95(d, 2H, J=8.4 Hz), 11.91(brs, 1H).

Example 100

4-{2-[5-(4,5,7-Trimethylbenzofuran-2-yl)-pyrrolyl]}benzoic acid

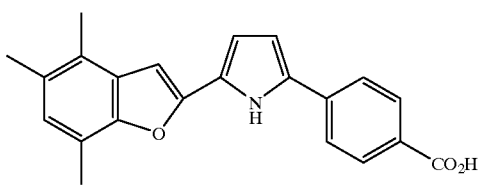

The title compound was prepared in a similar manner to that of Example 1 (D).

$^1$H -NMR (DMSO-$d_6$, 400 MHz) δ; 2.26(s, 3H), 2.35(s, 3H), 2.43(s, 3H), 6.67–6.71(m, 1H), 6.81–6.85(m, 1H), 6.87(s, 1H), 7.21(s, 1H), 7.88(d, 2H, J=8.4 Hz), 7.94(d, 2H, J=8.0 Hz), 11.78(brs, 1H).

Example 101

4-{2-[5-(6-Chloro-7-n-propylbenzofuran-2-yl)pyrrolyl]}benzoic acid

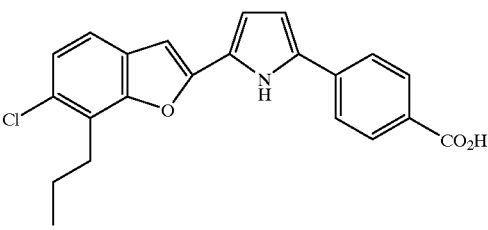

The title compound was prepared in a similar manner to that of Example 1 (D).

$^1$H-NMR (DMSO-$d_6$, 400 MHz) δ; 0.96(t, 3H, J=7.6 Hz), 1.64–1.76(m, 2H), 2.95–3.03(m, 2H), 6.73–6.76(m, 1H), 6.83–6.87(m, 1H), 7.19(s, 1H), 7.26(d, 1H, J=8.8 Hz), 7.47(d, 1H, J=8.8 Hz), 7.89(d, 2H, J=8.0 Hz), 7.96(d, 2H, J=8.4 Hz), 11.87(brs, 1H).

Example 102

4-{2-[5-(4-Chloro-7-n-butylbenzofuran-2-yl)pyrrolyl]}benzoic acid

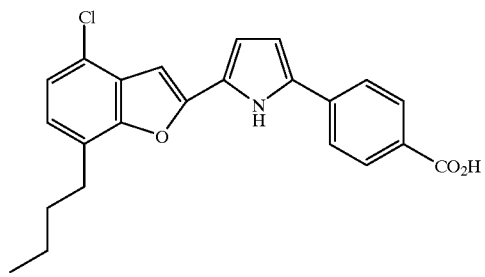

The title compound was prepared in a similar manner to that of Example 1 (D).

$^1$H-NMR (DMSO-$d_6$, 400 MHz) δ; 0.92(t, 3H, J=7.6 Hz), 1.29–1.38(m, 2H), 1.64–1.74(m, 2H), 2.84–2.92(m, 2H), 6.75–6.79(m, 1H), 6.83–6.87(m, 2H), 7.08(d, 1H, J=7.7 Hz), 7.22(d, 1H, J=7.7 Hz), 7.28(s, 1H), 7.88(d, 2H, J=8.8 Hz), 7.96(d, 2H, J=8.8 Hz), 11.90(brs, 1H).

Example 103

4-{2-[5-(3,5-Dichloro-4,7-dimethylbenzofuran-2-yl)pyrrolyl]}benzoic acid

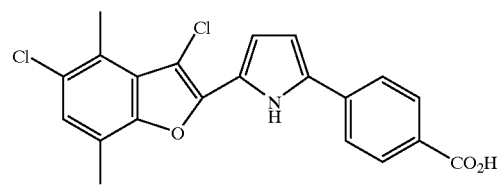

The title compound was prepared in a similar manner to that of Example 1 (D).

$^1$H-NMR (DMSO-$d_6$, 400 MHz) δ; 2.53(s, 3H), 2.69(s, 3H), 6.93(dd, 1H, J=2.4, 4.0 Hz), 7.01(dd, 1H, J=2.4, 4.0 Hz), 7.27(s, 1H), 7.95(s, 4H), 11.94(brs, 1H).

Example 104

4-{2-[5-(3-Chloro-4,7-dimethylbenzofuran-2-yl)pyrrolyl]}benzoic acid

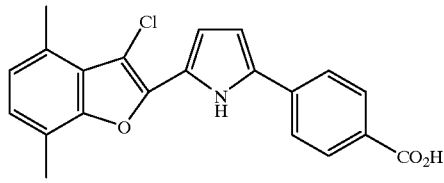

(A) Methyl 4-{2-[5-(3-chloro-4,7-dimethylbenzofuran-2-yl)pyrrolyl]}benzoate

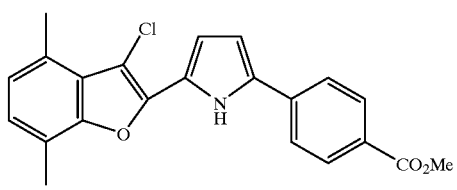

0.30 g of methyl 4-{2-[5-(4,7-dimethyl-benzofuran-2-yl)pyrrolyl]}benzoate was dissolved in 10 ml of N,N-dimethylformamide and 0.13 g of N-chlorosuccinimide was added to the solution. The resulting mixture was stirred at room temperature for 14 hours, followed by the addition of 30 ml of ethyl acetate. The organic layer was washed with brine, dried over anhydrous magnesium sulfate. After the desiccant was filtered off, the resulting mixture was concentrated. The resulting crude product was purified by silica gel column chromatography, and the resulting solid was washed with methanol to give 0.12 g of the title compound as pale yellow crystals.

$^1$H-NMR (CDCl$_3$, 400 MHz) δ; 2.50(s, 3H), 2.71(s, 3H), 3.92(s, 3H), 6.77–6.80(m, 1H), 6.91(d, 1H, J=7.6 Hz), 6.98(d, 1H, J=7.6 Hz), 7.01–7.04(m, 1H), 7.63(d, 2H, J=8.4 Hz), 8.08(d, 2H, J=8.4 Hz), 9.23(brs, 1H).

(B) 4-{2-[5-(3-Chloro-4,7-dimethylbenzofuran-2-yl)pyrrolyl]}benzoic acid

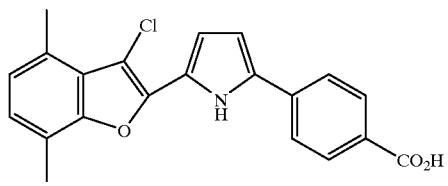

The title compound was prepared in a similar manner to that of Example 1 (D).

$^1$H-NMR (DMSO-d$_6$, 400 MHz) δ; 2.52(s, 3H), 2.65(s, 3H), 6.90–6.93(m, 1H), 6.95–6.99(m, 2H), 7.04–7.08(m, 1H), 7.95(s, 4H), 11.89(brs, 1H).

Example 105

4-{2-[5-(4,7-Diethylbenzofuran-2-yl)pyrrolyl]}benzoic acid

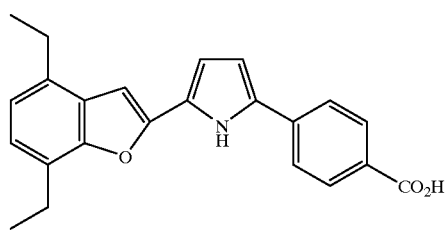

The title compound was prepared in a similar manner to that of Example 1 (D).

$^1$H-NMR (DMSO-d$_6$, 400 MHz) δ; 1.27(t, 3H, J=7.6 Hz), 1.30(t, 3H, J=7.6 Hz), 2.81(q, 2H, J=7.6 Hz), 2.88(q, 2H, J=7.6 Hz), 6.70(dd, 1H, J=2.4, 4.0 Hz), 6.83(dd, 1H, J=2.8, 3.6 Hz), 6.96(d, 1H, J=7.6 Hz), 7.01(d, 1H, J=7.6 Hz), 7.27(s, 1H), 7.88(d, 2H, J=8.4 Hz), 7.94(d, 2H, J=8.8 Hz), 11.78(brs, 1H).

Example 106

4-{2-[5-(5-Chloro-7-fluorobenzofuran-2-yl)pyrrolyl]}benzoic acid

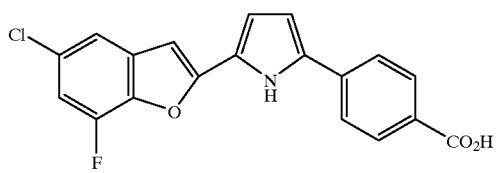

The title compound was prepared in a similar manner to that of Example 1 (D).

$^1$H-NMR (DMSO-d$_6$, 400 MHz) δ; 6.75–6.84(m, 2H), 7.25(s, 1H), 7.33(dd, 1H, J=2.4, 8.8 Hz) 7.60(d, 1H, J=2.4 Hz), 7.85(d, 2H, J=8.4 Hz), 7.94(d, 2H, J=8.4 Hz), 12.00(s, 1H).

Example 107

4-{2-[5-(7-Ethynylbenzofuran-2-yl)pyrrolyl]}benzoic acid

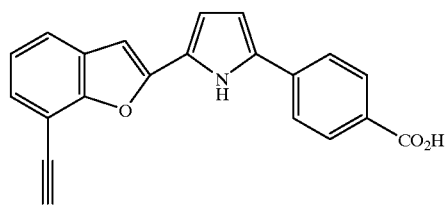

The title compound was prepared in a similar manner to that of Example 1 (D).

$^1$H-NMR (DMSO-d$_6$, 400 MHz) δ; 4.55(s, 1H), 6.73(dd, 1H, J=2.4, 4.0 Hz), 6.85(dd, 1H, J=2.4, 4.0 Hz), 7.23(t, 1H, J=8.0 Hz), 7.26(s, 1H), 7.36(dd, 1H, J=4.2, 8.0 Hz), 7.69(dd, 1H, J=1.2, 8.0 Hz), 7.89(d, 2H, J=8.4 Hz), 7.95(d, 2H, J=8.4 Hz), 11.94(brs, 1H).

Example 108

4-{2-[5-(7-(2-Methoxyethyl)benzofuran-2-yl)pyrrolyl]}benzoic acid

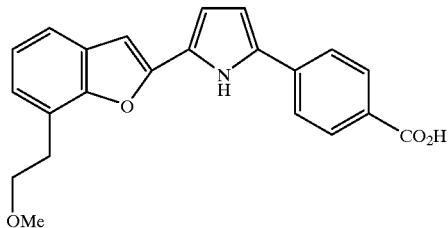

The title compound was prepared in a similar manner to that of Example 1 (D).

$^1$H-NMR (DMSO-d$_6$, 400 MHz) δ; 3.14(t, 2H, J=7.2 Hz), 3.27(s, 3H), 3.70(t, 2H, J=7.2 Hz), 6.73(dd, 1H, J=2.4, 3.6 Hz), 6.84(dd, 1H, J=2.4, 3.6 Hz), 7.11–7.16(m, 2H), 7.18(s, 1H), 7.46(dd, 1H, J=2.0, 6.8 Hz), 7.89(d, 2H, J=8.4 Hz), 7.94(d, 2H, J=8.4 Hz), 11.85(s, 1H), 12.83(brs, 1H).

Example 109

4-{2-[5-(5-Fluoro-7-methylbenzofuran-2-yl)pyrrolyl]}benzoic acid

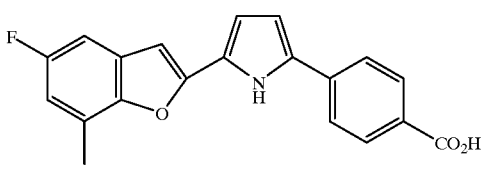

The title compound was prepared in a similar manner to that of Example 1 (D).

$^1$H-NMR (DMSO-d$_6$, 400 MHz) δ; 2.43(s, 3H), 6.75(brs, 1H), 6.85(brs, 1H), 6.93(d, 1H, J=10.0 Hz), 7.19(s, 1H), 7.26(d, 1H, J=6.8 Hz), 7.89(d, 2H, J=8.0 Hz), 7.95(d, 2H, J=8.0 Hz), 11.90(s, 1H).

Example 110

4-{2-[5-(4-Fluoro-7-methylbenzofuran-2-yl)pyrrolyl]}benzoic acid

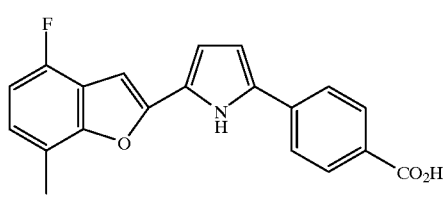

The title compound was prepared in a similar manner to that of Example 1 (D).

$^1$H-NMR (DMSO-d$_6$, 400 MHz) δ; 2.42(s, 3H), 6.72(brs, 1H), 6.84(brs, 1H), 7.06(t, 1H, J=8.0 Hz), 7.19(s, 1H), 7.44(dd, 1H, J=6.0, 8.0 Hz), 7.88(d, 2H, J=8.0 Hz), 7.94(d, 2H, J=8.0 Hz), 11.85(brs, 1H).

Example 111

4-{2-[5-(7-Bromo-4-fluorobenzofuran-2-yl)pyrrolyl]}benzoic acid

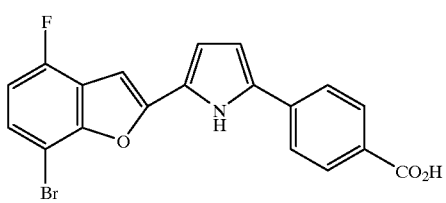

The title compound was prepared in a similar manner to that of Example 1 (D).

$^1$H-NMR (DMSO-d$_6$, 400 MHz) δ; 6.78(dd, 1H, J=2.4, 3.6 Hz), 6.87(dd, 1H, J=2.4, 3.6 Hz), 7.09(t, 1H, J=9.2 Hz), 7.48(dd, 1H, J=4.8, 8.4 Hz), 7.49(s, 1H), 7.93(d, 2H, J=8.8 Hz), 7.96(d, 2H, J=8.8 Hz), 12.20(brs, 1H).

Example 112

2-{2-[5-(4,7-Dimethylbenzofuran-2-yl)pyrrolyl]}pyridine-5-carboxylic acid

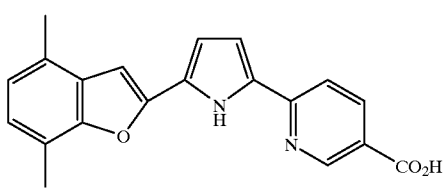

The title compound was prepared in a similar manner to that of Example 1 (D).

$^1$H-NMR (DMSO-d$_6$, 400 MHz) δ; 2.44(s, 3H), 2.46(s, 3H), 6.72–6.76(m, 1H), 6.92(d, 1H, J=8.0 Hz), 6.96(d, 1H, J=8.0 Hz), 7.04–7.09(m, 1H), 7.51(s, 1H), 7.93(d, 1H, J=7.6 Hz), 8.20(dd, 1H, J=2.4, 7.6 Hz), 9.02(d, 1H, J=2.4 Hz), 12.26(brs, 1H).

Example 113

4-{2-[5-(4,6,7-Trimethylbenzofuran-2-yl)pyrrolyl]}benzoic acid

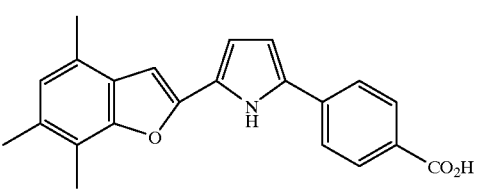

The title compound was prepared in a similar manner to that of Example 1 (D).

$^1$H-NMR (DMSO-d$_6$, 400 MHz) δ; 2.29(s, 3H), 2.38(s, 3H), 2.40(s, 3H), 6.69(brs, 1H), 6.81–6.84(m, 2H), 7.17(s, 1H), 7.86–7.95(m, 4H), 11.76((brs, 1H), 12.82(brs, 1H).

Example 114

6-{2-[5-(4,7-Dimethylbenzofuran-2-yl)pyrrolyl]}-2-naphthoic acid

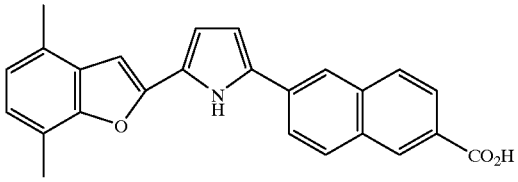

The title compound was prepared in a similar manner to that of Example 1 (D).

$^1$H-NMR (DMSO-d$_6$, 400 MHz) δ; 2.46(s, 3H), 2.47(s, 3H), 6.73(brd, 1H, J=3.6 Hz), 6.90(brd, 1H, J=3.7 Hz), 6.92(d, 1H, J=6.8 Hz), 6.96(d, 1H, J=6.8 Hz), 7.25(s, 1H), 7.93(d, 1H, J=8.4 Hz), 7.97(d, 1H, J=8.4 Hz), 8.01(d, 1H, J=8.4 Hz), 8.10(d, 1H, J=8.8 Hz), 8.35(s, 1H), 8.53(s, 1H), 11.88(brs, 1H).

Example 115

4-{2-[5-(4,7-Dimethylbenzofuran-2-yl)pyrrolyl]}1-naphthoic acid

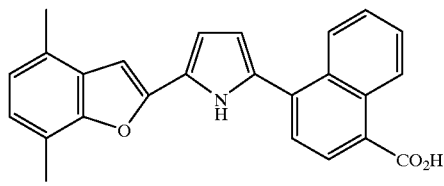

The title compound was prepared in a similar manner to that of Example 1 (D).

$^1$H-NMR (DMSO-d$_6$, 400 MHz) δ; 2.41(s, 3H), 2.47(s, 3H), 6.58(t, 1H, J=3.0 Hz), 6.81(t, 1H, J=3.0 Hz), 6.93(ABq, 2H, J=9.0 Hz), 7.18(s, 1H), 7.58–7.70(m, 2H), 7.72(d, 1H, J=9.0 Hz), 8.17(d, 1H, J=9.0 Hz), 8.40(d, 1H, J=9.0 Hz), 8.77(d, 1H, J=9.0 Hz).

Example 116

2,5-Dimethyl-4-{2-[5-(4,7-dimethylbenzofuran-2-yl)pyrrolyl]}benzoic acid

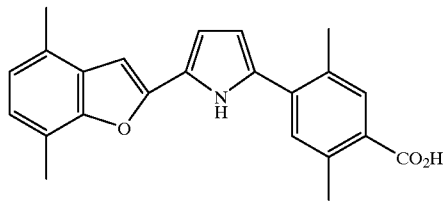

The title compound was prepared in a similar manner to that of Example 1 (D).

$^1$H-NMR (DMSO-d$_6$, 400 MHz) δ; 2.41(s, 3H), 2.42(s, 3H), 2.47(s, 3H), 2.55(s, 3H), 6.48(dd, 1H, J=2.5, 3.0 Hz), 6.71(dd, 1H, J=2.5, 3.0 Hz), 6.92(ABq, 2H, J=7.0 Hz), 7.18(s, 1H), 7.46(brs, 1H), 7.75(brs, 1H).

Example 117

5-{2-[5-(4,7-Dimethylbenzofuran-2-yl)pyrrolyl]}-2-furancarboxylic acid

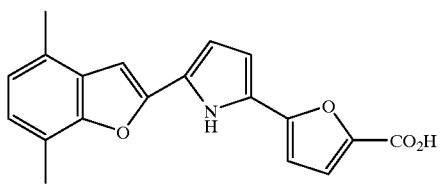

The title compound was prepared in a similar manner to that of Example 1 (D).

$^1$H-NMR (DMSO-d$_6$, 400 MHz) δ; 2.43(s, 3H), 2.45(s, 3H), 6.58(d, 1H, J=3.6 Hz), 6.79(d, 1H, J=3.6 Hz), 6.87–6.96(m, 3H), 7.01–7.08(brs, 1H), 7.18(s, 1H).

Example 118

3-{2-[5-(4,7-Dimethylbenzofuran-2-yl)-pyrrolyl]}benzoic acid

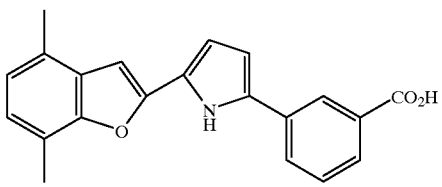

The title compound was prepared in a similar manner to that of Example 1 (D).

$^1$H-NMR (DMSO-d$_6$, 400 MHz) δ; 2.49(s, 3H), 2.57(s, 3H), 6.70(dd, 1H, J=2.5, 3.8 Hz), 6.74(dd, 1H, J=2.5, 3.8 Hz), 6.83(s, 1H), 6.93(d, 1H, J=7.5 Hz), 6.97(d, 1H, J=7.5 Hz), 7.52(t, 1H, J=8.0 Hz), 7.83(d, 1H, J=7.5 Hz), 7.96(d, 1H, J=7.5 Hz), 8.28(s, 1H), 9.03(brs, 1H).

Example 119

3-Bromo-4-{2-[5-(naphtho[1, 2-b]furan-2-yl)pyrrolyl]}benzoic acid

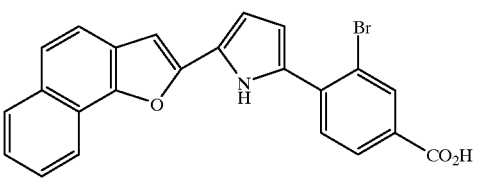

The title compound was prepared in a similar manner to that of Example 1 (D).

$^1$H-NMR (DMSO-d$_6$, 400 MHz) δ; 6.86(m, 2H), 7.31(s, 1H), 7.51(t, 1H, J=7.6 Hz), 7.65(t, 1H, J=7.8 Hz), 7.75(s, 1H), 7.79(d, 1H, J=8.0 Hz), 7.99(dd, 1H, J=1.2, 8.4 Hz), 8.02(d, 1H, J=8.4 Hz), 8.19(s, 1H), 8.32(d, 1H, J=8.0 Hz), 11.98(brs, 1H).

Example 120

3-Bromo-4-{2-[5-(4,7-dichlorobenzofuran-2-yl)pyrrolyl]}benzoic acid

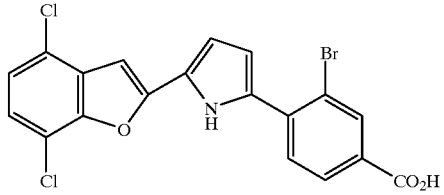

The title compound was prepared in a similar manner to that of Example 1 (D).

$^1$H-NMR (DMSO-$d_6$, 400 MHz) δ; 6.80(d, 1H, J=3.6 Hz), 6.83(d, 1H, J=3.6 Hz), 7.34(dd, 1H, J=1.0, 8.2 Hz), 7.35(s, 1H), 7.37(dd, 1H, J=0.6, 8.6 Hz) 7.70(brd, 1H, J=8.4 Hz), 7.94(brd, 1H, J=8.0 Hz), 8.16(brs, 1H).

Example 121

4-{2-[5-(3,4-Dimethylnaphthalen-1-yl)pyrrolyl]}benzoic acid

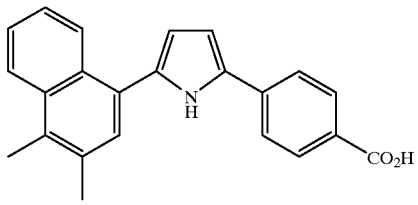

The title compound was prepared in a similar manner to that of Example 1 (D).

$^1$H-NMR (DMSO-$d_6$, 400 MHz) δ; 2.54(s, 3H), 2.65(s, 3H), 6.57(dd, 1H, J=2.8, 2.8 Hz), 6.85(dd, 1H, J=3.2, 3.2 Hz), 7.43(s, 1H), 7.47(dd, 1H, J=7.6, 7.6 Hz), 7.55(dd, 1H, J=7.2, 7.2 Hz), 7.62(d, 1H, J=8.4 Hz), 8.11(d, 4H, J=8.0 Hz), 8.68(brs, 1H).

Example 122

4-{2-[5-(5,8-Dimethylnaphthalen-2-yl)thienyl]}benzoic acid

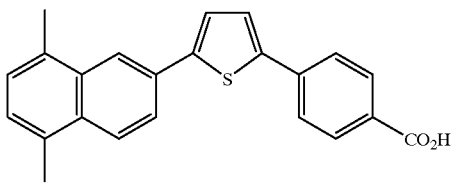

The title compound was prepared in a similar manner to that of Example 1 (D).

$^1$H-NMR (DMSO-$d_6$, 400 MHz) δ; 2.61(s, 3H), 2.67(s, 3H), 7.23(d, 1H, J=7.2 Hz), 7.26(d, 1H, J=7.6 Hz), 7.64(d, 1H, J=4.0 Hz) 7.70(d 2H, J=8.0 Hz) 7.73(d, 1H, J=3.6 Hz), 7.91(d, 3H, J=8.4 Hz), 8.06(d, 1H, J=8.8 Hz) 8.21(s, 1H).

Example 123

4-{2-[5-(5,8-Dimethylnaphthalen-2-yl)furyl]}benzoic acid

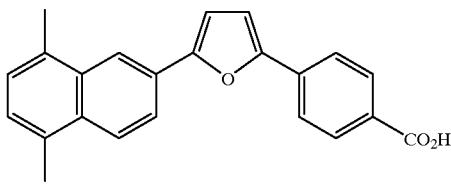

The title compound was prepared in a similar manner to that of Example 1 (D).

$^1$H-NMR (DMSO-$d_6$, 400 MHz) δ; 2.61(s, 3H), 2.70(s, 3H), 7.24(d, 1H, J=6.8 Hz), 7.27(d, 1H, J=7.2 Hz), 7.33(s, 2H), 7.97(d, 2H, J=8.4 Hz), 8.01(d, 3H, J=8.4 Hz), 8.07(d, 1H, J8.8 Hz), 8.39(s, 1H).

Example 124

4-{2-[5-(8-Ethyl-1-methoxynaphthalen-2-yl)pyrrolyl]}benzoic acid

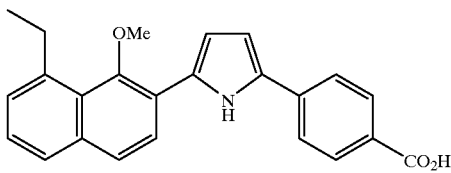

The title compound was prepared in a similar manner to that of Example 1 (D).

$^1$H-NMR (CDCl$_3$, 400 MHz) δ; 1.36(t, 3H, J=7.2 Hz), 3.35(q, 2H, J=7.6 Hz), 3.74(s, 3H), 6.77–6.81(m, 2H), 7.30–7.40(m, 2H), 7.60–7.73(m, 5H), 8.10–8.20(m, 2H), 10.34(brs, 1H).

Example 125

4-{2-[5-(8-Methyl-1-methoxynaphthalen-2-yl)pyrrolyl]}benzoic acid

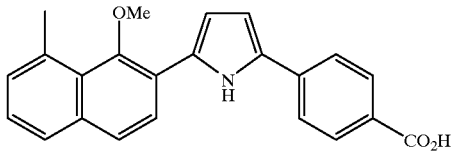

The title compound was prepared in a similar manner to that of Example 1 (D).

$^1$H-NMR (CDCl$_3$, 400 MHz) δ; 2.97(s, 3H), 3.73(s, 3H), 6.76–6.80(m, 2H), 7.28–7.35(m, 2H), 7.61–7.72(m, 5H), 8.14(d, 2H, J=8.4 Hz), 10.33(brs, 1H).

Example 126

4-{2-[5-(5-Acenaphthenyl)pyrrolyl]}benzoic acid

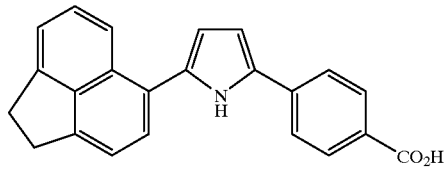

The title compound was prepared in a similar manner to that of Example 1 (D).

$^1$H-NMR (CDCl$_3$, 400 MHz) δ; 3.40–3.48(m, 4H), 6.64–6.66(m, 1H), 6.84–6.86(m, 1H), 7.33–7.36(m, 2H), 7.50–7.64(m, 4H), 8.03(d, 1H, J=8.4 Hz), 8.09–8.12(m, 2H), 8.76(brs, 1H).

Example 127

4-{2-[5-(5,8-Dimethyl-2H-chromen-3-yl)-pyrrolyl]}benzoic acid

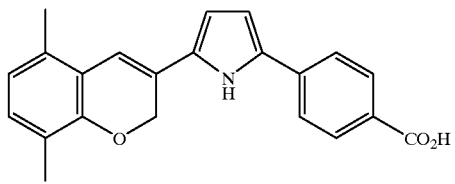

The title compound was prepared in a similar manner to that of Example 1 (D).

$^1$H-NMR (DMSO-d$_6$, 400 MHz) δ; 2.09(s, 3H), 2.34(s, 3H), 4.95(brs, 2H), 6.45–6.47(m, 1H), 6.67(d, 1H, J=7.6 Hz), 6.75–6.77(m, 1H), 6.84(d, 1H, J=7.6 Hz), 7.24(brs, 1H), 7.85–7.94(m, 4H).

Example 128

4-{2-[5-(5-Isopropyl-8-methyl-2H-chromen-3-yl)pyrrolyl]}benzoic acid

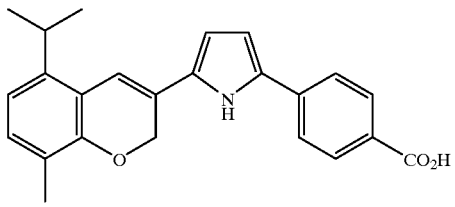

The title compound was prepared in a similar manner to that of Example 1 (D).

$^1$H-NMR (CDCl$_3$, 400 MHz) δ; 1.30(d, 6H, J=6.8 Hz), 3.28(hept, 1H, J=6.8 Hz), 4.99(d, 2H, J=1.2 Hz), 6.39–6.40 (m, 1H), 6.7–6.73(m, 1H), 6.81–6.86(m, 2H), 6.99(d, 1H, J=8.0 Hz), 7.64(d, 2H, J=8.4 Hz), 8.13(d, 2H, J=8.4 Hz), 8.70(brs, 1H).

Example 129

4-{2-[5-(5-Methyl-2H-chromen-3-yl)-pyrrolyl]}benzoic acid

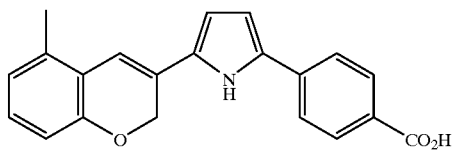

The title compound was prepared in a similar manner to that of Example 1 (D).

$^1$H-NMR (DMSO-d$_6$, 400 MHz) δ; 2.14(s, 3H), 5.04(brs, 2H), 6.43–6.45(m, 1H), 6.75–6.77(m, 1H), 6.81(t, 1H, J=7.6 Hz), 6.95(t, 1H, J=8.0 Hz), 7.09(brs, 1H), 7.86–7.93(m, 4H), 11.39(s, 1H), 12.82(brs, 1H).

Example 130

4-{2-[5-(5-Ethyl-2H-chromen-3-yl)-pyrrolyl]}benzoic acid

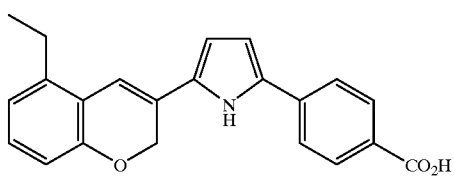

The title compound was prepared in a similar manner to that of Example 1 (D).

$^1$H-NMR (DMSO-d$_6$, 400 MHz) δ; 1.13(t, 3H, J=7.2 Hz), 2.48–2.55(m, 2H), 5.02(brs, 2H), 6.45(brs, 1H), 6.75–7.09 (m, 5H), 7.85–7.93(m, 4H), 11.39(s, 1H), 12.81(s, 1H).

Example 131

4-{2-[5-(5-Methoxy-2H-chromen-3-yl)-pyrrolyl]}benzoic acid

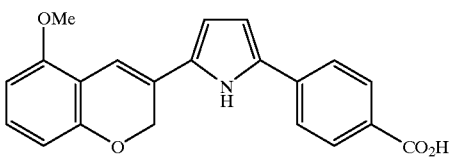

The title compound was prepared in a similar manner to that of Example 1 (D).

$^1$H-NMR (CDCl$_3$, 400 MHz) δ; 3.91(s, 3H), 5.00(brs, 2H), 6.34(brs, 1H), 6.50–6.55(m, 2H), 6.70(s, 1H), 6.95(s, 1H), 7.08(dd, 1H, J=7.2, 7.2 Hz), 7.62(d, 2H, J=7.6 Hz), 8.11(d, 2H, J=8.4 Hz), 8.77(brs, 1H).

Example 132

4-{2-[5-(8-Methoxy-7-methyl-2H-chromen-3-yl)pyrrolyl]}benzoic acid

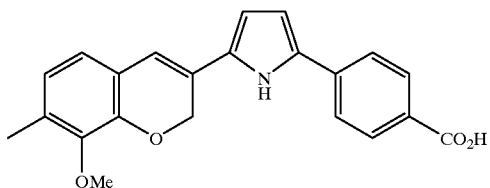

The title compound was prepared in a similar manner to that of Example 1 (D).

$^1$H-NMR (CDCl$_3$, 400 MHz) δ; 2.16(s, 3H), 3.73(s, 3H), 5.01(brs, 2H), 6.44(m, 1H), 6.70–7.77(m, 3H), 7.07(s, 1H), 7.85–7.93(m, 4H), 11.38(brs, 1H), 12.80(brs, 1H).

Example 133

4-{2-[5-(4-Methyl-2H-chromen-6-yl)-pyrrolyl]}benzoic acid

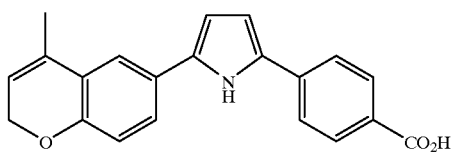

The title compound was prepared in a similar manner to that of Example 1 (D).

$^1$H-NMR (CDCl$_3$, 400 MHz) δ; 2.10(d, 3H, J=1.6 Hz), 4.79(q, 2H, J=1.6 Hz), 5.65(m, 1H), 6.51(dd, 1H, J=2.8, 3.6 Hz), 6.74(dd, 1H, J=2.8, 3.6 Hz), 6.85(d, 1H, J=8.0 Hz), 7.29–7.32(m, 2H), 7.59(d.2H, J=8.8 Hz), 8.10(d, 2H, J=8.4 Hz), 8.60(brs, 1H).

Example 134

4-{2-[5-(5-Bromo-8-methoxy-2H-chromen-3-yl)pyrrolyl]}benzoic acid

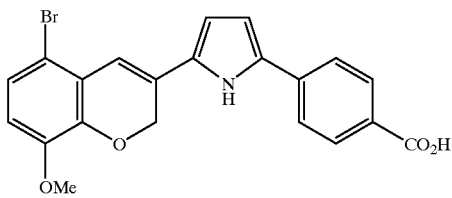

The title compound was prepared in a similar manner to that of Example 1 (D).

$^1$H-NMR (DMSO-d$_6$, 400 MHz) δ; 3.75(s, 3H), 4.97(brs, 2H), 6.53(brs, 1H), 6.79–6.82(m, 2H), 7.14(d, 1H, J=8.8 Hz), 7.22(brs, 1H), 7.91(brs, 4H), 11.65(brs, 1H), 12.83(brs, 1H).

Example 135

4-{2-[5-(8-Methoxy-5-methyl-2H-chromen-3-yl)pyrrolyl]}benzoic acid

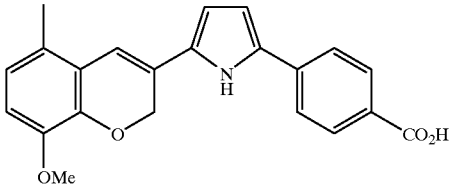

The title compound was prepared in a similar manner to that of Example 1 (D).

$^1$H-NMR (CDCl$_3$, 400 MHz) δ; 2.37(s, 3H), 3.88(s, 3H), 5.05(brs, 2H), 6.40(brs, 1H), 6.71–6.72(m, 4H), 7.64(d, 2H, J=7.6 Hz), 8.12(d, 2H, J=8.0 Hz), 8.68(brs, 1H).

Example 136

4-{2-[5-(5-Propyl-2H-chromen-3-yl)-pyrrolyl]}benzoic acid

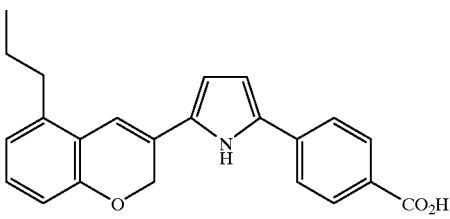

The title compound was prepared in a similar manner to that of Example 1 (D).

$^1$H-NMR (CDCl$_3$, 400 MHz) δ; 0.97(t, 3H, J=7.2 Hz), 1.63(tq, 2H, J=7.2, 7.2 Hz), 2.59(t, 2H, J=7.6 Hz), 5.04(s, 2H), 6.36(dd, 1H, J=2.4, 2.4 Hz), 6.62(brs, 1H), 6.86(dd, 1H, J=7.6,7.6 Hz), 6.94–7.01(m, 2H), 7.61(d, 2H, J=8.4 Hz), 8.11(d, 2H, J=8.4 Hz), 8.63(brs, 1H).

Example 137

4-{2-[5-(5-Chloro-8-methyl-2H-chromen-3-yl)pyrrolyl]}benzoic acid

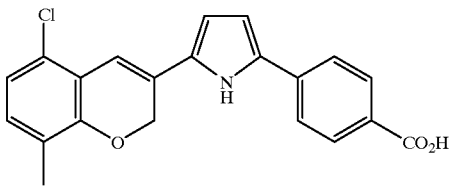

The title compound was prepared in a similar manner to that of Example 1 (D).

$^1$H-NMR (CDCl$_3$, 400 MHz) δ; 2.19(s, 3H), 5.05(d, 2H, J=1.2 Hz), 6.41(dd, 1H, J=3.6, 3.6 Hz), 6.71(dd, 1H, J=3.6, 3.6 Hz), 6.90(brs, 3H), 7.64(d, 2H, J=8.8 Hz), 8.11(d, 1H, J=8.8 Hz), 8.74(brs, 1H).

Example 138

4-{2-[5-(5,7,8-Trimethyl-2H-chromen-3-yl)-pyrrolyl]}benzoic acid

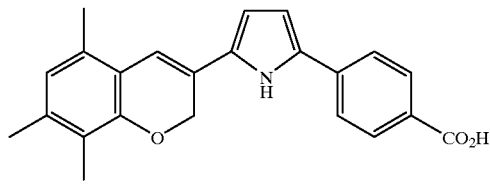

The title compound was prepared in a similar manner to that of Example 1 (D).

¹H-NMR (DMSO-d$_6$, 400 MHz) δ; 2.02(s, 3H), 2.15(s, 3H), 2.31(s, 3H), 4.91(s, 2H), 6.43(brs, 1H), 6.60(s, 1H), 6.75(brs, 1H), 7.23(S, 1H), 7.85–7.93(m, 4H), 11.35(s, 1H), 12.78(brs, 1H).

Example 139

4-{2-[5-(5,7-Dimethyl-2H-chromen-3-yl)-pyrrolyl]}benzoic acid

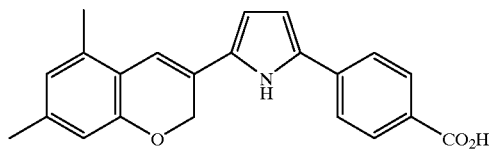

The title compound was prepared in a similar manner to that of Example 1 (D).

¹H-NMR (DMSO-d$_6$, 400 MHz) δ; 2.19(s, 3H), 2.34(s, 3H), 4.90(s, 2H), 6.43(dd, 1H, J=3.2, 3.2 Hz), 6.49(brs, 1H), 6.60(brs, 1H), 6.75(dd, 1H, J=3.2, 3.2 Hz), 7.23(brs, 1H), 7.86(d, 2H, J=8.4 Hz), 7.93(d, 2H, J8.8 Hz).

Example 140

4-{2-[5-(7,8-Dimethyl-2H-chromen-3-yl)-pyrrolyl]}benzoic acid

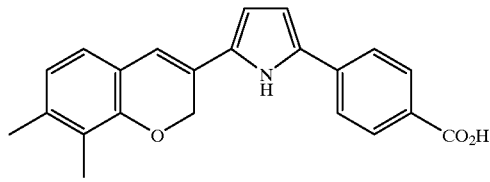

The title compound was prepared in a similar manner to that of Example 1 (D).

¹H-NMR (DMSO-d$_6$, 400 MHz) δ; 2.07(s, 3H), 2.19(s, 3H), 5.00(s, 2H), 6.41–6.43(m, 1H), 6.72–6.76(m, 2H), 6.84(d, 1H, J=7.6 Hz), 7.06(brs, 1H), 7.86(d, 2H, J=8.4 Hz), 7.91(d, 2H, J=8.8 Hz).

Example 141

4-{2-[5-(6-Methyl-2H-chromen-3-yl)-pyrrolyl]}benzoic acid

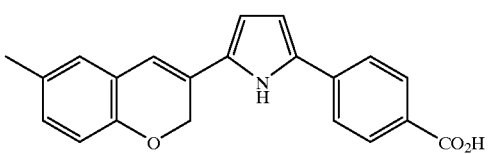

The title compound was prepared in a similar manner to that of Example 1 (D).

¹H-NMR (DMSO-d$_6$, 400 MHz) δ; 2.22(s, 3H), 4.97(s, 2H), 6.44(dd, 1H, J=2.0, 2.0 Hz), 6.70(d, 1H, J=7.6 Hz), 6.76(dd, 1H, J=2.0, 2.0 Hz), 6.87–6.89(m, 2H), 7.06(s, 1H), 7.85–7.93(m, 4H), 11.39(s, 1H), 12.79(brs, 1H)

Example 142

4-{2-[5-(5, 6-Dimethyl-2H-chromen-3-yl)-pyrrolyl]}benzoic acid

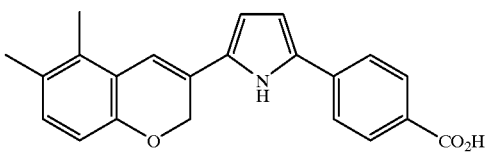

The title compound was prepared in a similar manner to that of Example 1 (D).

¹H-NMR (DMSO-d$_6$, 400 MHz) δ; 2.10(s, 3H), 2.19(s, 3H), 4.99(s, 2H), 6.44(s, 1H), 6.73(s, 1H), 6.77(brs, 2H), 7.04(s, 1H), 7.86–7.93(m, 4H), 11.38(s, 1H), 12.78(brs, 1H).

Example 143

4-{2-[5-(6-Chloro-2H-chromen-3-yl)-pyrrolyl]}benzoic acid

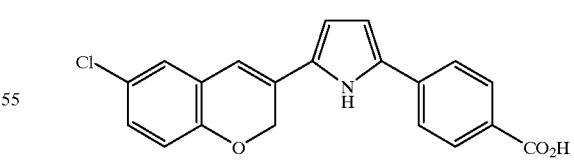

The title compound was prepared in a similar manner to that of Example 1 (D).

¹H-NMR (DMSO-d$_6$, 400 MHz) δ; 5.05(s, 2H), 6.46–6.52 (m, 1H), 6.74–6.79(m, 1H), 6.83(d, 1H, J=8.8 Hz), 7.05–7.10(m, 3H), 7.86(d, 2H, J=8.4 Hz) 7.92(d, 2H, J=8.0 Hz), 11.47(s, 1H), 12.80(brs, 1H).

Example 144

4-{2-[5-(7-Chloro-2H-chromen-3-yl)-pyrrolyl]}benzoic acid

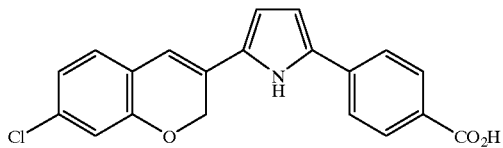

The title compound was prepared in a similar manner to that of Example 1 (D).

$^1$H-NMR (DMSO-$d_6$, 400 MHz) δ; 5.06(s, 2H), 6.47(dd, 1H, J=2.4, 3.2 Hz), 6.77(dd, 1H, J=2.4, 3.2 Hz), 6.91(d, 1H, J=2.0 Hz), 6.96(dd, 1H, J=2.0, 8.0 Hz), 7.10(d, 1H, J=8.0 Hz), 7.10(s, 1H), 7.87(d, 2H, J=8.4 Hz), 7.92(d, 2H, J=8.8 Hz), 11.44(s, 1H), 12.81(brs, 1H).

Example 145

4-{2-[5-(5, 6,7-Trimethyl-2H-chromen-3-yl)pyrrolyl]}benzoic acid

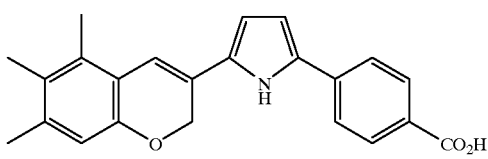

The title compound was prepared in a similar manner to that of Example 1 (D).

$^1$H-NMR (DMSO-$d_6$, 400 MHz) δ; 2.08(s, 2H), 2.18(s, 3H), 2.31(s, 3H), 4.83(s, 2H), 6.43(dd, 1H, J=2.8, 2.8 Hz), 6.53(s, 1H), 6.75(dd, 1H, J=3.2,3.2 Hz), 7.86(d, 2H, J=8.4 Hz), 7.93(d, 2H, J=8.0 Hz), 11.36(s, 1H), 12.78(brs, 1H).

Example 146

4-{2-[5-(5,6,8-Trimethyl-2H-chromen-3-yl)-pyrrolyl]}benzoic acid

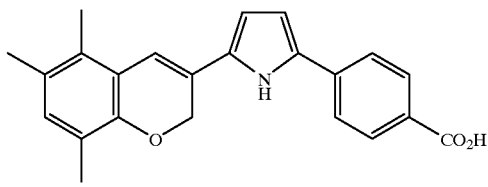

The title compound was prepared in a similar manner to that of Example 1 (D).

$^1$H-NMR (DMSO-$d_6$, 400 MHz) δ; 2.07(s, 3H), 2.14(s, 3H), 2.26(s, 3H), 4.88(s, 2H), 6.46(dd, 1H, J=2.4, 2.4 Hz), 6.75–6.77(m, 2H), 7.33(s, 1H), 7.87(d, 2H, J=8.8 Hz), 7.93(d, 2H, J=8.4 Hz), 11.39(s, 1H), 12.78(brs, 1H).

Example 147

4-{2-[5-(5-Chloro-2H-chromen-3-yl)-pyrrolyl]}benzoic acid

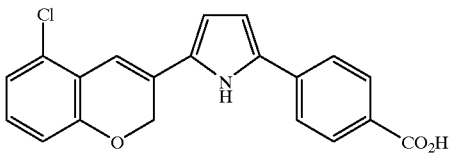

The title compound was prepared in a similar manner to that of Example 1 (D).

$^1$H-NMR (DMSO-$d_6$, 400 MHz) δ; 5.04(brs, 2H), 6.54 (dd, 1H, J=2.8, 2.8 Hz), 6.29(dd, 1H, J=2.8, 2.8 Hz), 6.82(d, 1H, J=8.4 Hz), 7.02–7.10(m, 2H), 7.37(brs, 1H), 7.90–7.95 (m, 4H), 11.63(s, 1H), 12.81(brs, 1H).

Example 148

4-{2-[5-(8-Methyl-2H-chromen-3-yl)-pyrrolyl]}benzoic acid

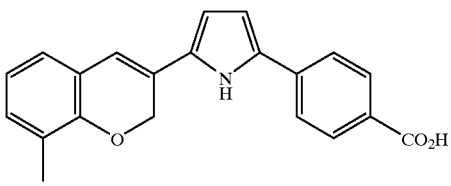

The title compound was prepared in a similar manner to that of Example 1 (D).

$^1$H-NMR (CDCl$_3$, 400 MHz) δ; 2.13(brs, 2H), 5.03(brs, 2H), 6.43–6.45(m, 1H), 6.75–6.77(m, 1H), 6.81(dd, 1H, J=7.2, 7.2 Hz), 6.92–6.96(m, 2H), 7.08(brs, 1H), 7.85–7.93 (m, 4H).

Example 149

4-{2-[5-(8-Trifluoromethyl-2H-chromen-3-yl)pyrrolyl]}benzoic acid

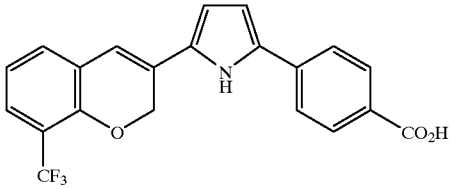

The title compound was prepared in a similar manner to that of Example 1 (D).

$^1$H-NMR (DMSO-$d_6$, 400 MHz) δ; 5.17(s, 2H), 6.53(brs, 1H), 6.79(brs, 1H), 7.07(dd, 1H, J=7.6, 7.6 Hz), 7.16(s, 1H), 7.36–7.38(m, 2H), 7.86–7.94(m, 4H), 11.49(s, 1H), 12.80 (brs, 1H).

Example 150

4-{2-[5-(3-Fluoro-4,7-dimethylbenzofuran-2-yl)pyrrolyl]}benzoic acid

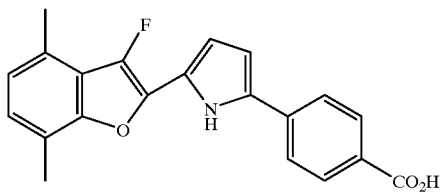

(A) Methyl 4-{2-[5-(3-fluoro-4,7-dimethylbenzofuran-2-yl)pyrrolyl]}benzoate

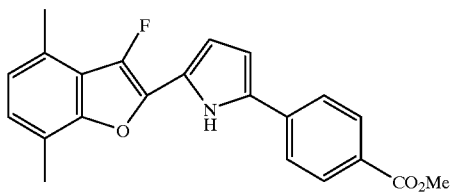

0.20 g of methyl 4-{2-[5-(4,7-dimethylbenzofuran-2-yl)pyrrolyl]}benzoate was dissolved in 5 ml of anhydrous tetrahydrofuran and 0.20 g of N-fluoro-3,5-dichloropyridinium triflate was added to the solution. The resulting mixture was stirred at room temperature for 30 minutes and poured into a chilled saturated aqueous solution of sodium bicarbonate, followed by the addition of 50 ml of ethyl acetate. The organic layer was washed with brine, dried over anhydrous magnesium sulfate. After the desiccant was filtered off, the filtrate was concentrated. The resulting crude product was purified by silica gel column chromatography to give 0.05 g of the title compound as pale yellow crystals.

$^1$H-NMR (CDCl$_3$, 400 MHz) δ; 2.48(s, 3H), 2.60(s, 3H), 3.94(s, 3H), 6.75–6.79(m, 2H), 6.92(d, 1H, J=7.6 Hz), 6.99(d, 1H, J=7.6 Hz), 7.62(d, 2H, J=8.4 Hz), 8.07(d, 2H, J=8.4 Hz), 8.92(brs, 1H).

(B) 4-{2-[5-(3-Fluoro-4,7-dimethylbenzofuran-2-yl)pyrrolyl]}benzoic acid

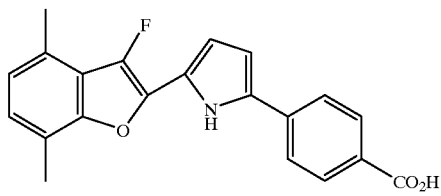

The title compound was prepared in a similar manner to that of Example 1 (D).

$^1$H-NMR (DMSO-d$_6$, 400 MHz) δ; 2.45(s, 3H), 2.53(s, 3H), 6.63–6.66(m, 1H), 6.89–6.92(m, 1H), 6.98(d, 1H, J=7.2 Hz), 7.06(d, 1H, J=7.2 Hz), 7.93(s, 4H), 11.87(s, 1H), 12.83(brs, 1H).

Example 151

4-{2-[5-(3-Bromo-4,7-dimethylbenzofuran-2-yl)pyrrolyl]}benzoic acid

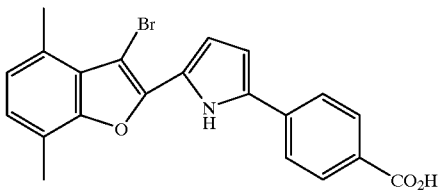

(A) Methyl 4-{2-[5-(3-bromo-4,7-dimethylbenzofuran-2-yl)pyrrolyl]}benzoate

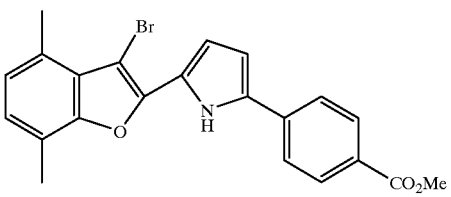

The title compound was prepared in a similar manner to that employed in the preparation of the 3-chloride except that N-bromosuccinimide was used instead of the N-chlorosuccinimide.

$^1$H-NMR (CDCl$_3$, 400 MHz) δ; 2.50(s, 3H), 2.73(s, 3H), 3.93(s, 3H), 6.77–6.80(m, 1H), 6.91(d, 1H, J=7.6 Hz), 6.98(d, 1H, J=7.6 Hz), 7.11–7.14(m, 1H), 7.63(d, 2H, J=8.4 Hz), 8.08(d, 2H, J=8.4 Hz), 9.38(brs, 1H).

(B) 4-{2-[5-(3-Bromo-4,7-dimethylbenzofuran-2-yl)pyrrolyl]}benzoic acid

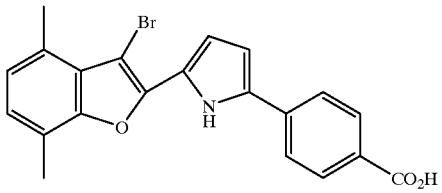

The title compound was prepared in a similar manner to that of Example 1 (D).

$^1$H-NMR (DMSO-d$_6$, 400 MHz) δ; 2.50(s, 3H), 2.67(s, 3H), 6.88–6.91(m, 1H), 6.96(d, 1H, J=7.2 Hz) 7.03–7.07(m, 2H), 7.92(s, 4H), 11.86(s, 1H), 12.83(brs, 1H).

Example 152

4-{2-[5-(6,7-Dichlorobenzofuran-2-yl)pyrrolyl]}benzoic acid

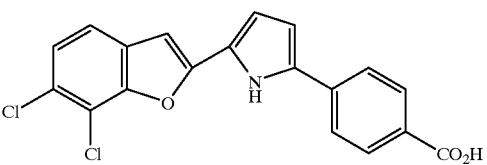

The title compound was prepared in a similar manner to that of Example 1 (D).

¹H-NMR (DMSO-d₆, 400 MHz) δ; 6.76–6.79(m, 1H), 6.85–6.88(m, 1H), 7.30(s, 1H), 7.47(d, 1H, J=8.4 Hz), 7.64(d, 1H, J=8.4 Hz), 7.89(d, 2H, J=8.4 Hz), 7.96(d, 2H, J=8.4 Hz), 11.98(s, 1H), 12.85(brs, 1H).

Example 153

4-{2-[5-(3-Chloro-5,7-dimethylbenzofuran-2-yl)pyrrolyl]}benzoic acid

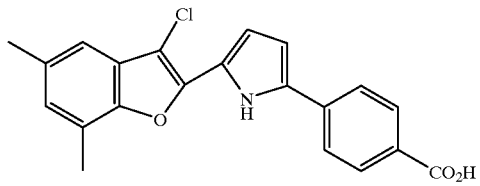

The title compound was prepared in a similar manner to that of Example 1 (D).

¹H-NMR (DMSO-d₆, 400 MHz) δ; 2.37(s, 3H), 2.51(s, 3H), 6.90–6.97(m, 2H), 7.02(brs, 1H), 7.16(brs, 1H), 7.94(s, 4H), 11.91(s, 1H), 12.85(brs, 1H).

Example 154

4-{2-[5-(3-Chloro-7-propylbenzofuran-2-yl)pyrrolyl]}benzoic acid

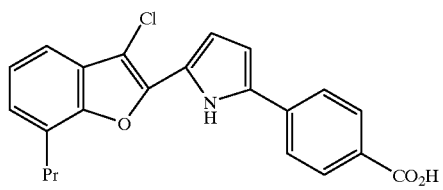

The title compound was prepared in a similar manner to that of Example 1 (D).

¹H-NMR (DMSO-d₆, 400 MHz) δ; 0.95(t, 3H, J=7.6 Hz), 1.70–1.82(m, 2H), 2.94(t, 2H, J=7.6 Hz), 6.91–6.94(m, 1H), 6.96–6.99(m, 1H), 7.22(dd, 1H, J=1.2, 7.6 Hz), 7.29(t, 1H, J=7.6 Hz), 7.38(dd, 1H, J=1.2, 7.6 Hz), 7.93(s, 4H), 11.90(s, 1H), 12.89(brs, 1H).

Example 155

4-{2-[5-(3-Fluoro-5,7-dimethylbenzofuran-2-yl)pyrrolyl]}benzoic acid

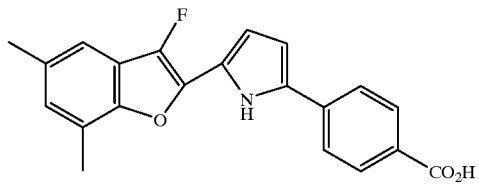

The title compound was prepared in a similar manner to that of Example 1 (D).

¹H-NMR (DMSO-d₆, 400 MHz) δ; 2.35(s, 3H), 2.46(s, 3H), 6.61–6.64(m, 1H), 6.85–6.88(m, 1H), 7.00(brs, 1H), 7.22(brs, 1H), 7.89(s, 4H), 11.86(s, 1H) 12.83(brs, 1H).

Example 156

4-{2-[5-(5-Fluoro-3,7-dimethylbenzofuran-2-yl)pyrrolyl]}benzoic acid

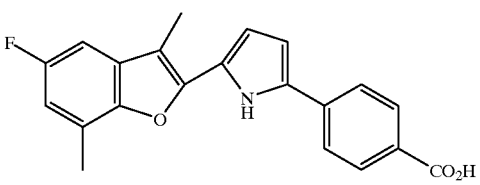

The title compound was prepared in a similar manner to that of Example 1 (D).

¹H-NMR (DMSO-d₆, 400 MHz) δ; 2.33(s, 3H), 2.53(s, 3H), 6.64–6.67(m, 1H), 6.87–6.90(m, 1H), 6.95(dd, 1H, J=2.0, 10.4 Hz), 7.22(dd, 1H, J=2.0, 10.4 Hz), 7.93(s, 4H), 11.73(s, 1H), 12.84(brs, 1H).

Example 157

4-{2-[5-(5-Fluoro-4,7-dimethylbenzofuran-2-yl)pyrrolyl]}benzoic acid

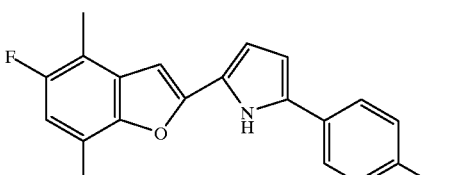

The title compound was prepared in a similar manner to that of Example 1 (D).

¹H-NMR (DMSO-d₆, 400 MHz) δ; 2.34(s, 3H), 2.46(s, 3H), 6.71–6.74(m, 1H), 6.83–6.86(m, 1H), 6.90(d, 1H, J=10.8 Hz), 7.26(s, 1H), 7.89(d, 2H, J=8.4 Hz), 7.95(d, 2H, J=8.4 Hz), 11.84(s, 1H), 12.83(brs, 1H).

Example 158

4-{2-[5-(5-Fluoro-3,4,7-trimethylbenzofuran-2-yl)pyrrolyl]}benzoic acid

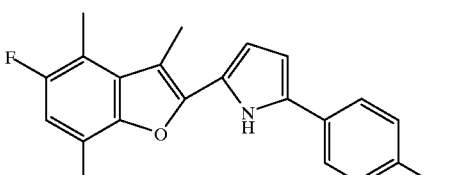

The title compound was prepared in a similar manner to that of Example 1 (D).

¹H-NMR (DMSO-d₆, 400 MHz) δ; 2.48(s, 6H), 2.50(s, 3H), 6.59–6.62(m, 1H), 6.85–6.88(m, 1H), 6.92(d, 1H, J=10.8 Hz), 7.92(s, 4H), 11.72(s, 1H), 12.80(brs, 1H).

Example 159

4-{2-[5-(3,5-Difluoro-4,7-dimethylbenzofuran-2-yl)pyrrolyl]}benzoic acid

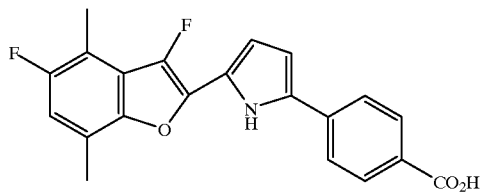

The title compound was prepared in a similar manner to that of Example 1 (D).

$^1$H-NMR (DMSO-$d_6$, 400 MHz) δ; 2.42(s, 3H), 2.48(s, 3H), 6.65–6.68(m, 1H), 6.89–6.92(m, 1H), 7.03(d, 1H, J=10.8 Hz), 7.93(s, 4H), 11.91(s, 1H), 12.85(brs, 1H).

Example 160

4-{2-[5-(3-Chloro-5-fluoro-4,7-dimethylbenzofuran-2-yl)pyrrolyl]}benzoic acid

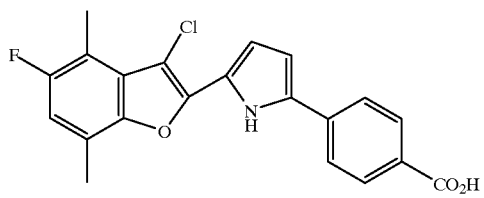

The title compound was prepared in a similar manner to that of Example 1 (D).

$^1$H-NMR (DMSO-$d_6$, 400 MHz) δ; 2.48(s, 3H), 2.52(s, 3H), 6.91–6.94(m, 1H), 6.98–7.01(m, 1H), 7.04(d, 1H, J=10.8 Hz), 7.95(s, 4H), 11.92(s, 1H), 12.86(brs, 1H).

Example 161

4-{2-[5-(7-Ethoxy-5-fluoro-4-methylbenzofuran-2-yl)pyrrolyl]}benzoic acid

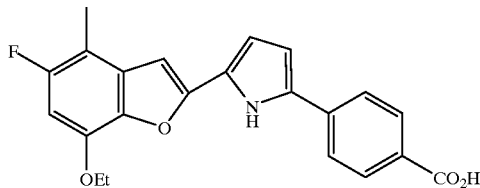

The title compound was prepared in a similar manner to that of Example 1 (D).

$^1$H-NMR (DMSO-$d_6$, 400 MHz) δ; 1.38(t, 3H, J=7.6 Hz), 2.29(s, 3H), 4.20(q, 2H, J=7.6 Hz), 6.69–6.72(m, 1H), 6.77(d, 1H, J=10.8 Hz), 6.81–6.84(m, 1H), 7.26(s, 1H), 7.89(d, 2H, J=8.4 Hz), 7.94(d, 2H, J=8.4 Hz), 11.88(s, 1H), 12.80(brs, 1H).

Example 162

4-{2-[5-(7-Ethyl-5-fluoro-4-methylbenzofuran-2-yl)pyrrolyl]}benzoic acid

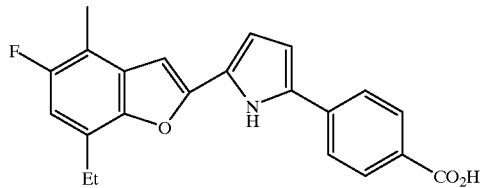

The title compound was prepared in a similar manner to that of Example 1(D).

$^1$H-NMR (DMSO-$d_6$, 400 MHz) δ; 1.27(t, 3H, J=7.6 Hz), 2.34(s, 3H), 2.85(q, 2H, J=7.6 Hz), 6.71–6.74(m, 1H), 6.83–6.86(m, 1H), 6.91(d, 1H, J=10.8 Hz), 7.88(d, 2H, J=8.4 Hz), 7.95(d, 2H, J=8.4 Hz), 11.83(s, 1H), 12.86(brs, 1H).

Example 163

4-{2-[5-(7-Ethyl-3,5-difluoro-4-methylbenzofuran-2-yl)pyrrolyl]}benzoic acid

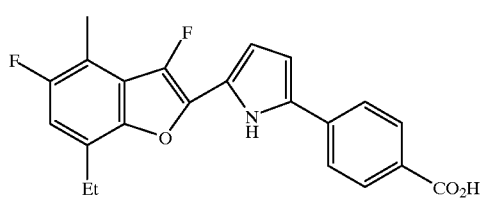

The title compound was prepared in a similar manner to that of Example 1 (D).

$^1$H-NMR (DMSO-$d_6$, 400 MHz) δ; 1.28(t, 3H, J=7.6 Hz), 2.43(s, 3H), 2.90(q, 2H, J=7.6 Hz), 6.65–6.68(m, 1H), 6.86–6.89(m, 1H), 7.04(d, 1H, J=11.2 Hz), 7.85–7.96(m, 4H), 11.87(s, 1H), 12.85(brs, 1H).

Example 164

4-{2-[5-(7-Chloro-4-fluorobenzothiophen-2-yl)pyrrolyl]}benzoic acid

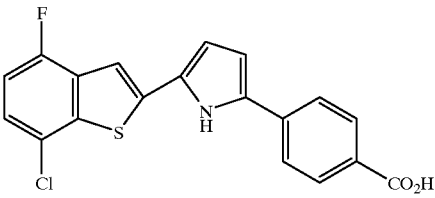

The title compound was prepared in a similar manner to that of Example 1 (D).

$^1$H-NMR (DMSO-$d_6$, 400 MHz) δ; 6.71–6.74(m, 1H), 6.81–6.84(m, 1H), 7.27(t, 1H, J=8.8 Hz), 7.42(dd, 1H, J=4.4, 8.8 Hz), 7.90(d, 2H, J=8.4 Hz), 7.95(d, 2H, J=8.4 Hz), 11.40(s, 1H), 12.81(brs, 1H).

Example 165

4-{2-[5-(3,5-Dichloro-7-methylbenzothiophen-2-yl)pyrrolyl]}benzoic acid

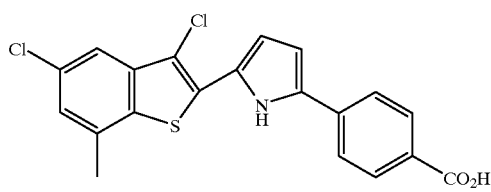

The title compound was prepared in a similar manner to that of Example 1 (D).

¹H-NMR (DMSO-d$_6$, 400 MHz) δ; 2.52(s, 3H), 6.87–6.94 (m, 2H), 7.38(brs, 1H), 7.61(brs, 1H), 7.90(s, 4H), 11.81(s, 1H), 12.85(brs, 1H).

Example 166

4-{2-[5-(3-Chloro-5-fluoro-7-methylbenzothiophen-2-yl)pyrrolyl]}benzoic acid

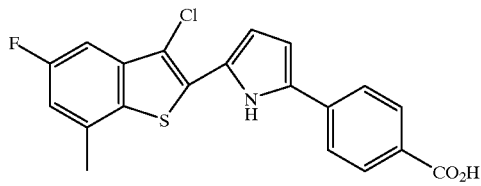

The title compound was prepared in a similar manner to that of Example 1 (D).

¹H-NMR (DMSO-d$_6$, 400 MHz) δ; 2.53(s, 3H), 6.88–6.94 (m, 4H), 7.24(dd, 1H, J=2.4, 9.6 Hz), 7.40(dd, 1H, J=2.4, 9.6 Hz), 7.93(s, 4H), 11.80(s, 1H), 12.87(brs, 1H).

Example 167

4-{2-[5-(7-Fluoro-4-trifluoromethylbenzofuran-2-yl)pyrrolyl]}benzoic acid

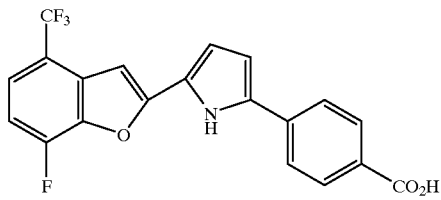

The title compound was prepared in a similar manner to that of Example 1 (D).

¹H-NMR (DMSO-d$_6$, 400 MHz) δ; 6.87–6.92(m, 2H), 7.35(dd, 1H, J=10.0, 10.4 Hz), 7.53(brs, 1H), 7.62(dd, 1H, J=3.6, 8.8 Hz), 7.93(d, 2H, J=8.8 Hz), 7.96(d, 2H, J=8.8 Hz).

Example 168

4-{2-[5-(3-Chloro-5-fluoro-7-methylbenzofuran-2-yl)pyrrolyl]}benzoic acid

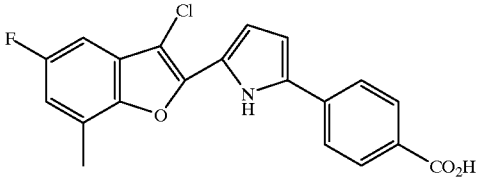

The title compound was prepared in a similar manner to that of Example 1 (D).

¹H-NMR (DMSO-d$_6$, 400 MHz) δ; 2.57(s, 3H), 6.91–6.94 (m, 1H), 6.96–7.02(m, 1H), 7.09(dd, 1H, J=2.7, 11.0 Hz), 7.17(dd, 1H, J=2.3, 8.0 Hz), 7.95(brs, 4H), 12.0(s, 1H).

Example 169

4-{2-[5-(3-Chloro-7-ethyl-5-fluorobenzofuran-2-yl)pyrrolyl]}benzoic acid

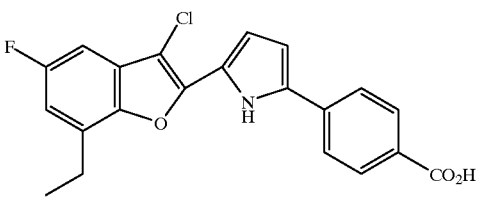

The title compound was prepared in a similar manner to that of Example 1 (D).

¹H-NMR (DMSO-d$_6$, 400 MHz) δ; 1.30(t, 3H, J=8.0 Hz), 3.00(q, 2H, J=7.2 Hz) 6.90–6.93(m, 1H), 6.98–7.00(m, 1H), 7.12(dd, 1H, J=2.9, 10.4 Hz), 7.18(dd, 1H, J=2.4, 8.8 Hz), 7.93-(d, 2H, J=8.0 Hz), 7.96(d, 2H, J=8.0 Hz), 11.96(brs, 1H).

Example 170

4-(2-[5-(3-Chloro-5-fluoro-7-propylbenzofuran-2-yl)pyrrolyl]}benzoic acid

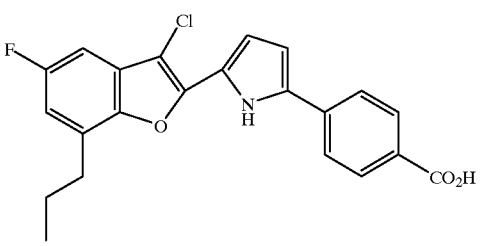

The title compound was prepared in a similar manner to that of Example 1 (D).

¹H-NMR (DMSO-d$_6$, 400 MHz) δ; 0.96(t, 3H, J=6.8 Hz), 1.72–1.80(m, 2H), 2.96(t, 2H, J=7.2 Hz), 6.90–6.93(m, 1H), 6.98–7.01(m, 1H), 7.10(dd, 1H, J=2.0, 10.4 Hz), 7.18(dd, 1H, J=2.0, 7.6 Hz), 7.92(d, 2H, J=8.4 Hz), 7.96(d, 2H, J=8.4 Hz), 11.88(brs, 1H).

Example 171

4-{2-[5-(3-Chloro-5-fluoro-7-propylbenzofuran-2-yl)-3-chloropyrrolyl}]benzoic acid

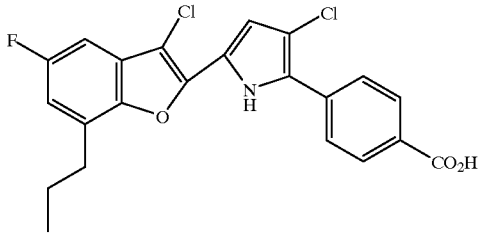

The title compound was prepared in a similar manner to that of Example 1(D)

$^1$H-NMR (DMSO-$d_6$, 400 MHz) δ; 0.94(t, 3H, J=7.0 Hz), 1.73–1.80(m, 2H), 2.90–2.98(m, 2H), 7.01(d, 1H, J=2.8 Hz), 7.13(dd, 1H, J=2.6, 10.4 Hz), 7.22(dd, 1H, J=2 4, 8.0 Hz), 7.88(d, 2H, J=8.4 Hz), 8.05(d, 2H, J=8.4 Hz).

Example 172

4-{2-[5-(3-Bromo-5-fluoro-7-methylbenzofuran-2-yl)pyrrolyl]}benzoic acid

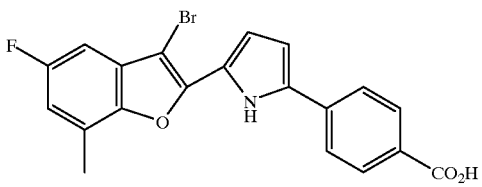

The title compound was prepared in a similar manner to that of Example 1 (D)

$^1$H-NMR (DMSO-$d_6$, 400 MHz) δ; 2.58(s, 3H), 6.92–6.94 (m, 1H), 7.06–7.16(m, 3H), 7.95(brs, 4H), 12.00(s, 1H).

Example 173

4-{2-[5-(7-Ethyl-5-fluoro-3-methylbenzofuran-2-yl) pyrrolyl]}benzoic acid

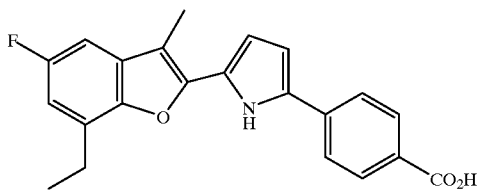

The title compound was prepared in a similar manner to that of Example 1 (D).

$^1$H-NMR (DMSO-$d_6$, 400 MHz) δ; 1.31(t, 3H, J=7.6 Hz), 2.33(s, 3H), 2.97(q, 2H, J=7.6 Hz), 6.64–6.66(m, 1H), 6.86–6.89(m, 1H), 6.97(dd, 1H, J=2.4, 10.0 Hz), 7.22(dd, 1H, J=2.4, 8.8 Hz), 7.91(d, 2H, J=8.4 Hz), 7.93(d, 2H, J=8.4 Hz), 11.73(s, 1H), 12.82(brs, 1H).

Example 174

4-{2-[5-(3,5-Difluoro-7-ethylbenzofuran-2-yl) pyrrolyl]}benzoic acid

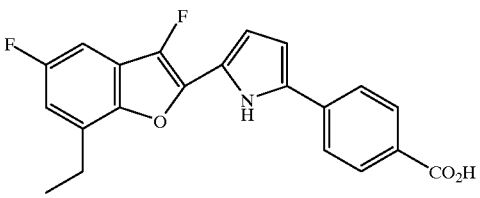

The title compound was prepared in a similar manner to that of Example 1 (D).

$^1$H-NMR (DMSO-$d_6$, 400 MHz); 1.32(t, 3H, J=7.6 Hz), 2.96(q, 2H, J=7.6 Hz), 6.68–6.71(m, 1H), 6.91(dd, 1H, J=2.4, 3.6 Hz), 7.10(dd, 1H, J=2.4, 10.4 Hz), 7.30(dd, 1H, J=2.4, 8.0 Hz), 7.94(brs, 4H), 11.95(s, 1H), 12.86(brs, 1H).

Example 175

4-{2-[5-(4-Ethyl-5-fluoro-7-methylbenzofuran-2-yl) pyrrolyl]}benzoic acid

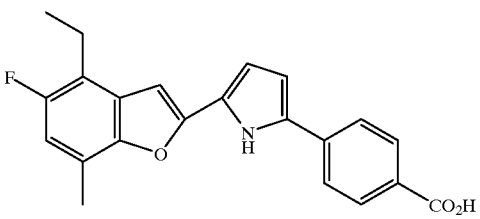

The title compound was prepared in a similar manner to that of Example 1 (D).

$^1$H-NMR (DMSO-$d_6$, 400 MHz) δ; 1.23(t, 3H, J=7.6 Hz), 2.46(s, 3H), 2.79(q, 4H, J=7.6 Hz), 6.72–6.75(m, 1H), 6.84–6.86(m, 1H), 6.90(d, 1H, J=10.8 Hz), 7.30(s, 1H), 7.89(d, 2H, J=8.4 Hz), 7.95(d, 2H, J=8.4 Hz), 11.84(brs, 1H).

Example 176

4-{2-[5-(4,7-Diethyl-3,5-difluorobenzofuran-2-yl) pyrrolyl]}benzoic acid

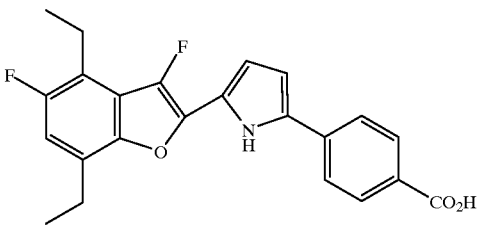

The title compound was prepared in a similar manner to that of Example 1 (D).

$^1$H-NMR (DMSO-$d_6$, 400 MHz) δ; 1.23(t, 3H, J=7.2 Hz), 1.30(t, 3H, J=7.2 Hz), 2.82–2.88(m, 2H), 2.92(q, 2H, J=7.2 Hz), 6.67–6.70(m, 1H), 6.90–6.92(m, 1H), 7.05(d, 1H, J=11.2 Hz), 7.94(s, 4H), 11.90(brs, 1H).

Example 177

4-{2-[5-(3-Bromo-4,7-diethyl-5-fluorobenzofuran-2-yl)pyrrolyl]}benzoic acid

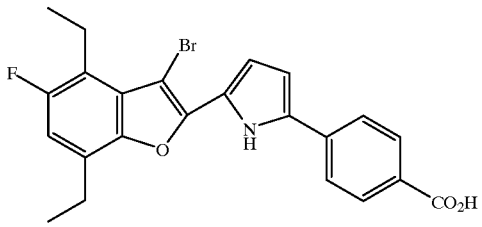

The title compound was prepared in a similar manner to that of Example 1 (D).

$^1$H-NMR (DMSO-$d_6$, 400 MHz) δ; 1.22(t, 3H, J=7.6 Hz), 1.30(t, 3H, J=7.6 Hz), 2.97(q, 2H, J=7.6 Hz), 3.03–3.10(m, 2H), 6.90–6.92(m, 1H), 7.07(d, 1H, J=11.2 Hz), 7.09–7.12 (m, 1H), 7.93(d, 2H, J=8.4 Hz), 7.96(d, 2H, J=8.4 Hz), 11.90(brs, 1H).

Example 178

4-{2-[5-(3,5-Dichloro-7-methylbenzofuran-2-yl)pyrrolyl]}benzoic acid

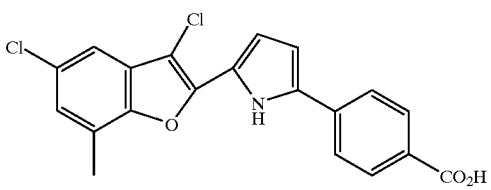

The title compound was prepared in a similar manner to that of Example 1 (D).

$^1$H-NMR (DMSO-$d_6$, 400 MHz) δ; 2.58(s, 3H), 6.92–6.95 (m, 1H), 7.00–7.02(m, 1H), 7.27–7.29(m, 1H), 7.40–7.42 (m, 1H), 7.96(s, 4H), 12.00(s, 1H).

Example 179

4-{2-[5-(3,5-Dichloro-7-ethylbenzofuran-2-yl)pyrrolyl]}benzoic acid

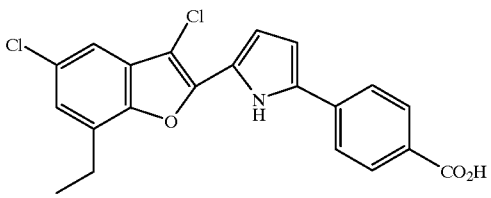

The title compound was prepared in a similar manner to that of Example 1 (D).

$^1$H-NMR (DMSO-$d_6$, 400 MHz) δ; 1.33(t, 3H, J=7.7 Hz), 3.00(q, 2H, J=7.7 Hz), 6.94(dd, 1H, J=2.8, 4.0 Hz), 7.01(dd, 1H, J=2.0, 3.6 Hz), 7.29(d, 1H, J=2.0 Hz), 7.42(d, 1H, J=1.6 Hz), 7.96(s, 4H), 11.99(brs, 1H).

Example 180

4-{2-[5-(3-Fluoro-4,5,7-trimethylbenzofuran-2-yl)pyrrolyl]}benzoic acid

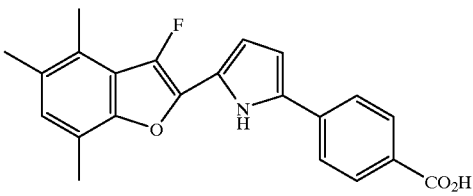

The title compound was prepared in a similar manner to that of Example 1 (D).

$^1$H-NMR (DMSO-$d_6$, 400 MHz) δ; 2.26(s, 3H), 2.43(s, 3H), 2.45(s, 3H), 6.61–6.65(m, 1H), 6.88–6.90(m, 1H), 6.97–7.00(m, 1H), 7.93(s, 4H), 11.84(brs, 1H).

Example 181

4-{2-[5-(3-Chloro-4,5,7-trimethylbenzofuran-2-yl)pyrrolyl]}benzoic acid

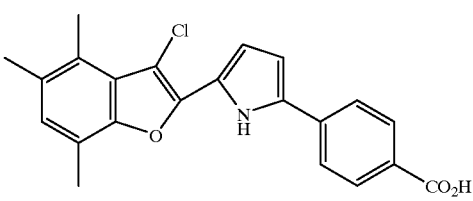

The title compound was prepared in a similar manner to that of Example 1 (D).

$^1$H-NMR (DMSO-$d_6$, 400 MHz) δ; 2.27(s, 3H), 2.50(s, 3H), 2.57(s, 3H), 6.89–6.92(m, 1H), 6.94–6.97(m, 1H), 6.98–7.00(m, 1H), 7.94(s, 4H), 11.85(brs, 1H).

Example 182

4-{2-[5-(3-Bromo-4,5,7-trimethylbenzofuran-2-yl)pyrrolyl]}benzoic acid

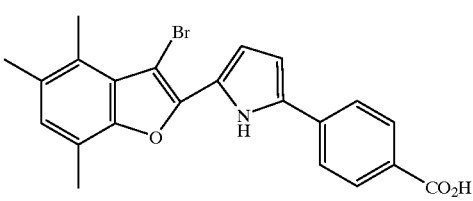

The title compound was prepared in a similar manner to that of Example 1 (D).

$^1$H-NMR (DMSO-$d_6$, 400 MHz) δ; 2.27(s, 3H), 2.50(s, 3H), 2.61(s, 3H), 6.88–6.91(m, 1H), 6.98 –7.00(m, 1H), 7.04–7.07(m, 1H), 7.94(s, 4H), 11.85(brs, 1H).

Example 183

4-{2-[5-(5-Fluoro-4-methylbenzofuran-2-yl)pyrrolyl]}benzoic acid

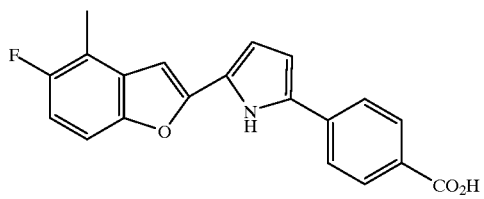

The title compound was prepared in a similar manner to that of Example 1 (D).

¹H-NMR (DMSO-d$_6$, 400 MHz) δ; 2.40(s, 3H), 6.72–6.75 (m, 1H), 6.83–6.86(m, 1H), 7.04(dd, 1H, J=9.2, 9.6 Hz), 7.29(s, 1H), 7.39(dd, 1H, J=3.6, 8.4 Hz), 7.90(d, 2H, J=8.4 Hz), 7.95(d, 2H, J=8.4 Hz), 11.93(brs, 1H).

Example 184

4-{2-[5-(5-Chloro-4,7-dimethylbenzofuran-2-yl)pyrrolyl]}benzoic acid

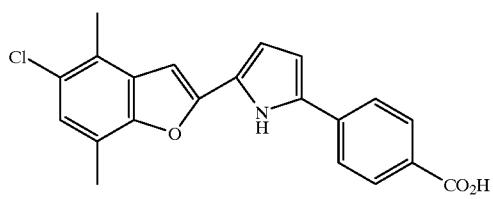

The title compound was prepared in a similar manner to that of Example 1 (D).

¹H-NMR (DMSO-d$_6$, 400 MHz) δ; 3.24(s, 3H), 3.39(s, 3H), 6.73–6.75(m, 1H), 6.84–6.86(m, 1H), 7.12(s, 1H), 7.27(s, 1H), 7.88–7.90(d, 2H, J=8.8 Hz), 7.94–7.96(d, 2H, J=8.8 Hz), 11.59(brs, 1H).

Example 185

4-{2-[5-(5-Chloro-3-fluoro-4,7-dimethylbenzofuran-2-yl)pyrrolyl]}benzoic acid

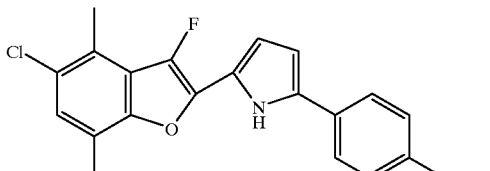

The title compound was prepared in a similar manner to that of Example 1 (D).

¹H-NMR (DMSO-d$_6$, 400 MHz) δ; 2.49(s, 3H), 2.54(s, 3H), 6.68–6.69(m, 1H), 6.91–6.92(m, 1H), 7.26(s, 1H), 7.94(s, 4H), 11.59(brs, 1H).

Example 186

4-{2-[5-(3-Bromo-5-chloro-4,7-dimethylbenzofuran-2-yl)pyrrolyl]}benzoic acid

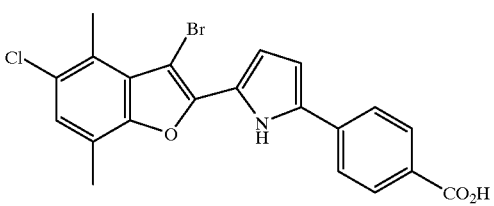

The title compound was prepared in a similar manner to that of Example 1 (D).

¹H-NMR (DMSO-d$_6$, 400 MHz) δ; 2.53(s, 3H), 2.73(s, 3H), 6.91–6.92(m, 1H), 7.10–7.11(m, 1H), 7.27(s, 1H), 7.95(s, 4H), 11.59(brs, 1H).

Example 187

4-{2-[5-(5-Chloro-3,4,7-trimethylbenzofuran-2-yl)pyrrolyl]}benzoic acid

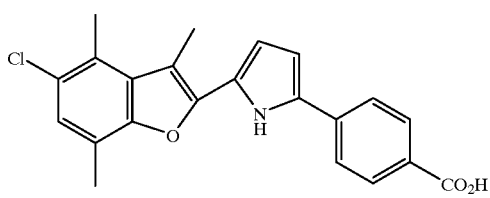

The title compound was prepared in a similar manner to that of Example 1 (D).

¹H-NMR (DMSO-d$_6$, 400 MHz) δ; 2.52(s, 3H), 2.62(s, 3H), 3.29(s, 3H), 6.61–6.62(m, 1H), 6.86–6.88(m, 1H), 7.15(s, 1H), 7.89–7.91(d, 2H, J=8.8 Hz), 7.92–7.94(d, 2H, J=8.8 Hz), 11.56(brs, 1H).

Example 188

4-{2-[5-(5-Chloro-4-methylbenzofuran-2-yl)pyrrolyl]}benzoic acid

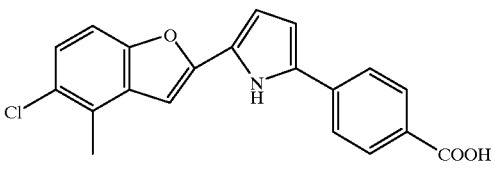

The title compound was prepared in a similar manner to that of Example 1 (D).

¹H-NMR (DMSO-d$_6$, 400 MHz) δ; 2.48(s, 3H), 6.75–6.76 (m, 1H), 6.84–6.86(m, 1H), 7.12(d, 1H, J=1.2 Hz), 7.17(s, 1H), 7.54(d, 1H, J=1.6 Hz), 7.88–7.96(m, 4H), 11.90(s, 1H), 12.80(brs, 1H).

Example 189

4-{2-[5-(7-Chloro-5-fluoro-4-propylbenzofuran-2-yl)pyrrolyl]}benzoic acid

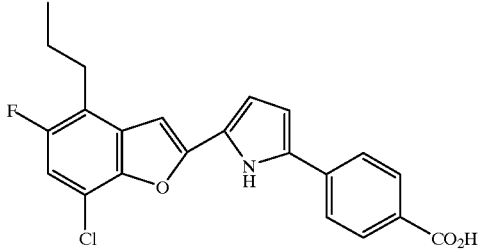

The title compound was prepared in a similar manner to that of Example 1 (D).

$^1$H-NMR (DMSO-$d_6$, 400 MHz) δ; 0.94(t, 3H, J=7.2 Hz), 1.66(q, 2H, J=7.2 Hz), 2.78(t, 2H, J=7.2 Hz), 6.74–6.77(m, 1H), 6.82–6.85(m, 1H), 7.29(d, 1H, J=10.0 Hz), 7.41(s, 1H), 7.87(d, 2H, J=8.4 Hz), 7.95(d, 2H, J=8.4 Hz), 11.91(brs, 1H).

Example 190

4-{2-[5-(5-Fluoro-6-methylbenzofuran-2-yl)pyrrolyl]}benzoic acid

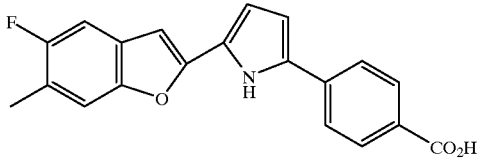

The title compound was prepared in a similar manner to that of Example 1 (D).

$^1$H-NMR (DMSO-$d_6$, 400 MHz) δ; 2.31(s, 3H), 6.68–6.72(m, 1H), 6.82–6.85(m, 1H), 7.15(s, 1H), 7.40(d, 1H, J=10.0 Hz), 7.47(d, 1H, J=6.4 Hz), 7.88(d, 2H, J=8.4 Hz), 7.94(d, 2H, J=8.4 Hz), 11.90(brs, 1H).

Example 191

4-{2-[5-(5,7-Difluorobenzofuran-2-yl)-pyrrolyl]}benzoic acid

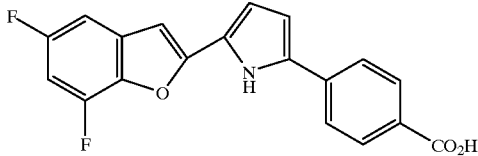

The title compound was prepared in a similar manner to that of Example 1 (D).

$^1$H-NMR (DMSO-$d_6$, 400 MHz) δ; 6.78–6.81(m, 1H), 6.85–6.88(m, 1H), 7.18–7.25(m, 1H), 7.29(d, 1H, J=3.2 Hz), 7.37(dd, 1H, J=2.4, 8.4 Hz), 7.89(d, 2H, J=8.4 Hz), 7.95(d, 2H, J=8.8 Hz), 12.02(brs, 1H).

Example 192

4-{2-[5-(4-Ethyl-5-fluorobenzofuran-2-yl)-pyrrolyl]}benzoic acid

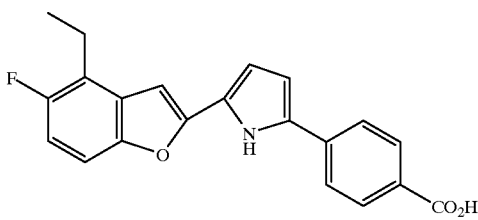

The title compound was prepared in a similar manner to that of Example 1 (D).

$^1$H-NMR (DMSO-$d_6$, 400 MHz) δ; 1.25(t, 3H, J=7.6 Hz), 2.80–2.88(m, 2H), 6.72–6.75(m, 1H), 6.83–6.86(m, 1H), 7.00–7.06(m, 1H), 7.33(s, 1H), 7.38–7.42(m, 1H), 7.89(d, 2H, J=8.8 Hz), 7.95(d, 2H, J=8.8 Hz), 11.91(brs, 1H).

Example 193

4-{2-[5-(5-Chloro-7-ethyl-3-fluorobenzofuran-2-yl)pyrrolyl]}benzoic acid

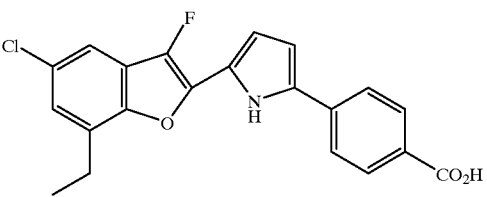

The title compound was prepared in a similar manner to that of Example 1 (D).

$^1$H-NMR (DMSO-$d_6$, 400 MHz) δ; 1.32(t, 3H, J=7.6 Hz), 2.69(q, 2H, J=7.6 Hz), 6.69–6.72(m, 1H), 6.90–6.93(m, 1H), 7.26–7.28(m, 1H), 7.54–7.57(m, 1H), 7.90–7.96(m, 4H), 11.95(brs, 1H).

Example 194

4-{2-[5-(5-Chloro-7-methylmethylenedioxymethylbenzofuran-2-yl)pyrrolyl]}benzoic acid

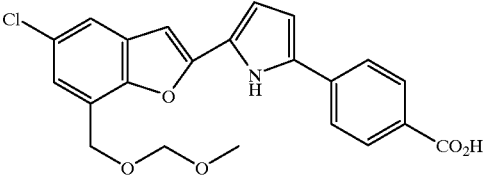

The title compound was prepared in a similar manner to that of Example 1 (D).

$^1$H-NMR (DMSO-$d_6$, 400 MHz) δ; 3.36(s, 3H), 4.74(s, 2H), 4.85(s, 2H), 6.74–6.75(m, 1H), 6.85–6.87(m, 1H), 7.22(s, 1H), 7.25(d, 1H, J=2 Hz), 7.69(d, 1H, J=2 Hz), 7.88(d, 2H, J=8.4 Hz), 7.95(d, 2H, J=8.4 Hz), 11.93(brs, 1H).

Example 195

4-{2-[5-(5-Chloro-7-nitrilebenzofuran-2-yl)-pyrrolyl]}benzoic acid

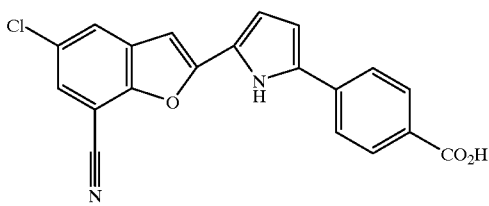

The title compound was prepared in a similar manner to that of Example 1 (D).

$^1$H-NMR (DMSO-$d_6$, 400 MHz) δ; 6.87–6.88(m, 1H), 6.92–6.93(m, 1H), 7.26(s, 1H), 7.64(s, 1H), 7.89(d, 2H, J=8.4 Hz), 7.92(s, 1H), 8.00(d, 2H, J=8.4 Hz), 12.09(brs, 1H).

Example 196

4-{2-[5-(7-Chloro-4-ethyl-5-fluorobenzofuran-2-yl)pyrrolyl]}benzoic acid

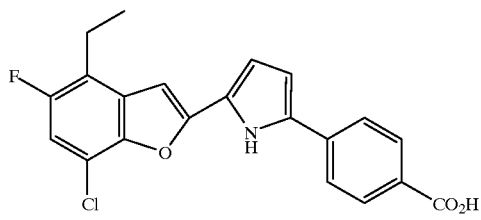

The title compound was prepared in a similar manner to that of Example 1 (D).

$^1$H-NMR (DMSO-$d_6$, 400 MHz) δ; 1.22(t, 3H, J=7.2 Hz), 2.81(q, 2H, J=7.2 Hz), 6.76–6.79(m, 1H), 6.86–6.89(m, 1H), 7.30(d, 1H, J=10.0 Hz), 7.42(s, 1H), 7.90(d, 2H, J=8.4 Hz), 7.96(d, 2H, J=8.4 Hz), 11.96(s, 1H), 12.84(brs, 1H).

Example 197

4-{2-[5-(4-Ethyl-5-fluoro-7-propoxybenzofuran-2-yl)pyrrolyl]}benzoic acid

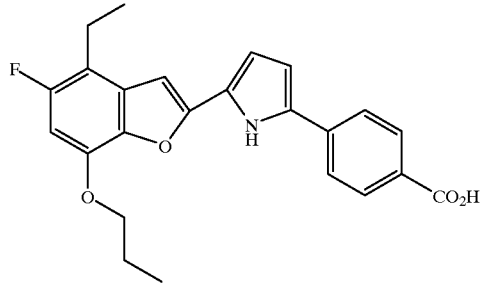

The title compound was prepared in a similar manner to that of Example 1 (D).

$^1$H-NMR (DMSO-$d_6$, 400 MHz) δ; 1.01(t, 3H, J=7.2 Hz), 1.20(t, 3H, J=7.2 Hz), 1.80(hex, 2H, J=7.2 Hz), 2.73(q, 2H, J=7.2 Hz), 4.10(t, 2H, J=7.2 Hz), 6.69–6.72(m, 1H), 6.77(d, 1H, J=12.4 Hz), 6.82–6.85(m, 1H), 7.30(s, 1H), 7.88(d, 2H, J=8.4 Hz), 7.94(d, 2H, J=8.4 Hz), 11.86(s, 1H), 12.82(brs, 1H).

Example 198

4-{2-[5-(4-ethyl-5,7-difluorobenzofuran-2-yl)pyrrolyl]}benzoic acid

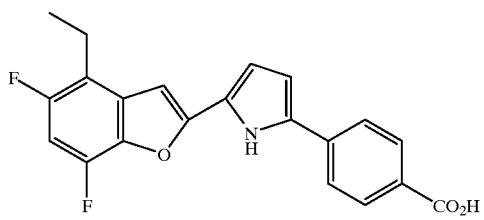

The title compound was prepared in a similar manner to that of Example 1 (D).

$^1$H-NMR (DMSO-$d_6$, 400 MHz) δ; 1.23(t, 3H, J=7.6 Hz), 2.77–2.83(m, 2H), 6.78–6.80(m, 1H), 6.85–6.88(m, 1H), 7.18(t, 1 H, J=10.8 Hz), 7.41(d, 1H, J=2.8 Hz), 7.90(d, 2H, J=8.8 Hz), 7.96(d, 2H, J=8.8 Hz), 11.98(brs, 1H).

What is claimed is:

1. A compound or a pharmacologically acceptable salt thereof or a hydrate of the salt represented by the formula:

(Ia)

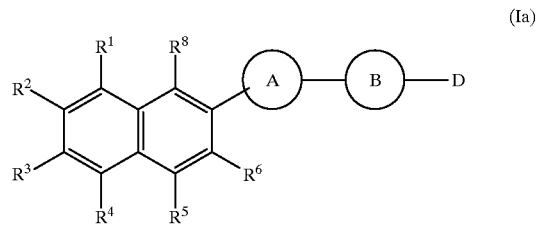

wherein $R^1$, $R^2$, $R^3$, $R^4$, $R^5$, $R^6$ and $R^8$ are the same or different from each other and each represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl, or alternatively two of $R^1$, $R^2$, $R^3$, $R^4$, $R^5$, $R^6$ and $R^8$ adjacent to each other together with the carbon atoms to which they are bonded respectively may form a ring which may contain a heteroatom or be substituted; A represents an optionally substituted aromatic hydrocarbon ring or an optionally substituted unsaturated heterocycle; B represents an optionally substituted phenyl group; and D represents optionally protected carboxyl.

2. A compound or a pharmacologically acceptable salt thereof or a hydrate of the salt represented by the formula:

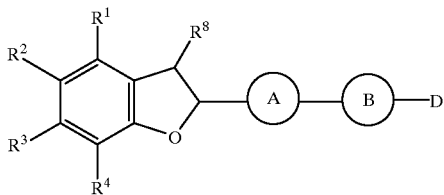

(IIa)

wherein $R^1$, $R^2$, $R^3$, $R^4$ and $R^8$ each represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl, or alternatively two of $R^1$, $R^2$, $R^3$, $R^4$ and $R^8$ adjacent to each other together with the carbon atoms to which they are bonded respectively may form a ring which may contain a heteroatom or be substituted; A represents an optionally substituted aromatic hydrocarbon ring or an optionally substituted unsaturated heterocycle; B represents an optionally substituted phenyl group; and D represents optionally protected carboxyl.

3. A compound or a pharmacologically acceptable salt thereof or a hydrate of the salt represented by the formula:

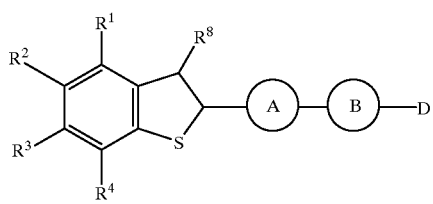

(IIIa)

wherein $R^1$, $R^2$, $R^3$, $R^4$ and $R^8$ each represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl, or alternatively two of $R^1$, $R^2$, $R^3$, $R^4$ and $R^8$ adjacent to each other together with the carbon atoms to which they are bonded respectively may form a ring which may contain a heteroatom or be substituted; A represents an optionally substituted aromatic hydrocarbon ring or an optionally substituted unsaturated heterocycle; B represents an optionally substituted phenyl group; and D represents optionally protected carboxyl.

4. A compound or a pharmacologically acceptable salt thereof or a hydrate of the salt represented by the formula:

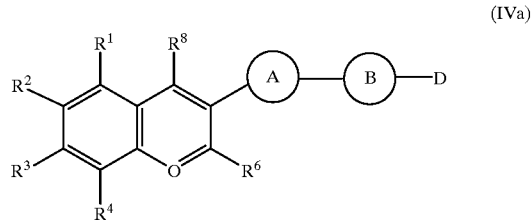

(IVa)

wherein $R^1$, $R^2$, $R^3$, $R^4$ and $R^8$ are the same or different from each other and each represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl, or alternatively two of $R^1$, $R^2$, $R^3$, $R^4$, $R^6$, and $R^8$ adjacent to each other together with the carbon atoms to which they are bonded respectively may form a ring which may contain a heteroatom or be substituted; A represents an optionally substituted aromatic hydrocarbon ring or an optionally substituted unsaturated heterocycle; B represents an optionally substituted phenyl group; and D represents optionally protected carboxyl.

5. The compound of claim 1, 2, 3 or 4, wherein A represents an optionally substituted pyrrole ring and B represents an optionally substituted phenyl group.

6. A pharmaceutical composition comprising a compound of claim 1, 2, 3 or 4 together with a pharmaceutically acceptable carrier.

7. A method of treating a medical condition comprising administering an effective amount of a compound of claim 1, 2, 3 or 4, wherein the medical condition is selected from the group consisting of cornification anomalies, skin diseases, alopeciae, osteoporoses, osteopeniae, bone and joint diseases, leukemiae, graft in organ transplantation rejection, graft versus host diseases in bone marrow or stem cell transplantation, nephropathy, glomerulonephritis, malignant lymphomas, squamous cell carcinomas, solid carcinomas, inflammations and allergic diseases, intractable infections, hyperthyroidism, hypercalcemia, fibroses, atherosclerosis, restenosis, nonmalignant hyperplastic diseases related to lipid metabolism and transport diseases, hyperlipidemia, diabetes, dry eye syndrome, solar skin injury, wounds and diseases against which acceleration of apoptosis induction is efficacious.

* * * * *

UNITED STATES PATENT AND TRADEMARK OFFICE
CERTIFICATE OF CORRECTION

PATENT NO. : 6,358,995 B1
DATED : March 19, 2002
INVENTOR(S) : Tagami et al.

It is certified that error appears in the above-identified patent and that said Letters Patent is hereby corrected as shown below:

Column 116,
Line 3, claim 4 should read:

4. A compound or a pharmacologically acceptable salt thereof or a hydrate of the salt represented by the formula:

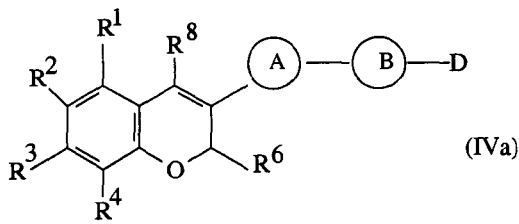

(IVa)

wherein $R^1$, $R^2$, $R^3$, $R^4$ and $R^8$ are the same or different from each other and each represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl, or alternatively two of $R^1$, $R^2$, $R^3$, $R^4$, $R^6$, and $R^8$ adjacent to each other together with the carbon atoms to which they are bonded respectively may form a ring which may contain a heteroatom or be substituted; A represents an optionally substituted aromatic hydrocarbon ring or an optionally substituted unsaturated heterocycle; B represents an optionally substituted phenyl group; and D represents optionally protected carboxyl.

Signed and Sealed this

Twentieth Day of September, 2005

JON W. DUDAS
*Director of the United States Patent and Trademark Office*